US010247737B2

(12) United States Patent
Moreau et al.

(10) Patent No.: US 10,247,737 B2
(45) Date of Patent: Apr. 2, 2019

(54) KITS FOR CLASSIFYING A SUBJECT HAVING OR AT RISK FOR DEVELOPING IDIOPATHIC SCOLIOSIS

(71) Applicant: Chu Sainte-Justine, Montréal (CA)

(72) Inventors: Alain Moreau, Montréal (CA); Marie-Yvonne Akoume Ndong, Montréal (CA)

(73) Assignee: Chu Sainte-Justine (CA)

( * ) Notice: Subject to any disclaimer, the term of this patent is extended or adjusted under 35 U.S.C. 154(b) by 0 days.

(21) Appl. No.: 14/917,757

(22) PCT Filed: Sep. 9, 2014

(86) PCT No.: PCT/CA2014/050853
§ 371 (c)(1),
(2) Date: Mar. 9, 2016

(87) PCT Pub. No.: WO2015/032005
PCT Pub. Date: Mar. 12, 2015

(65) Prior Publication Data
US 2016/0216277 A1    Jul. 28, 2016

Related U.S. Application Data

(60) Provisional application No. 61/879,314, filed on Sep. 18, 2013, provisional application No. 61/875,162, filed on Sep. 9, 2013.

(51) Int. Cl.
| A61K 38/19 | (2006.01) |
| A61F 5/02 | (2006.01) |
| A61K 33/04 | (2006.01) |
| A61K 31/713 | (2006.01) |
| A61K 31/4045 | (2006.01) |
| G01N 33/68 | (2006.01) |
| A61K 45/06 | (2006.01) |
| C12N 15/113 | (2010.01) |
| G01N 33/487 | (2006.01) |

(52) U.S. Cl.
CPC .......... *G01N 33/6893* (2013.01); *A61F 5/02* (2013.01); *A61F 5/026* (2013.01); *A61K 31/4045* (2013.01); *A61K 31/713* (2013.01); *A61K 33/04* (2013.01); *A61K 38/19* (2013.01); *A61K 45/06* (2013.01); *C12N 15/1138* (2013.01); *G01N 33/48728* (2013.01); *C12N 2310/14* (2013.01); *C12N 2320/30* (2013.01); *G01N 2333/47* (2013.01); *G01N 2333/726* (2013.01); *G01N 2800/10* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 6,015,837 A * | 1/2000 | Etlinger ............... A61K 31/135 |
| | | 514/307 |
| 6,025,155 A | 2/2000 | Hadlaczky et al. |
| 6,077,677 A | 6/2000 | Hodgson et al. |
| 6,204,023 B1 | 3/2001 | Robinson et al. |
| 7,967,767 B2 | 6/2011 | Ogilvie |
| 7,989,175 B2 * | 8/2011 | Moreau ............... C12Q 1/527 |
| | | 435/7.21 |
| 9,029,094 B2 | 5/2015 | Moreau et al. |
| 2002/0160970 A1 | 10/2002 | Hadlaczky et al. |
| 2003/0083293 A1 | 5/2003 | Hadlaczky et al. |
| 2009/0137934 A1 | 5/2009 | Seon |
| 2009/0275871 A1 | 11/2009 | Liu |
| 2010/0075333 A1 | 3/2010 | Moreau |
| 2012/0088809 A1 * | 4/2012 | Falco ............... C07D 405/04 |
| | | 514/422 |

FOREIGN PATENT DOCUMENTS

| WO | 03073102 A1 | 9/2003 |
| WO | 2004040236 A2 | 5/2004 |
| WO | 2006068459 A1 | 6/2006 |
| WO | 2008119170 A1 | 10/2008 |
| WO | 2009155159 A2 | 12/2009 |
| WO | 2010040234 A1 | 4/2010 |
| WO | 2010044796 A1 | 4/2010 |
| WO | WO 2012/045176 A1 * | 4/2012 |

(Continued)

OTHER PUBLICATIONS

Akoume et al., "Disrupted Gi-coupled receptor signaling occurs in adolescent idiopathic scoliosis", J. clin. Invest., (2013) (submitted).
Akoume, M.Y. et al., "Cell-based assay protocol for the prognostic prediction of idiopathic scoliosis using cellular dielectric spectroscopy", Journal of Visualized Experiments [URL: http://jove.com/video/50768] (2013) Oct. 2013, vol. 80, e50768, pp. 1-9. No ISSN.
Akoume, M.Y. et al., "Cell-based screening test for idiopathic scoliosis using cellular dialectric spectroscopy", SPINE Jun. 2010, vol. 35, No. 13, pp. E601-608, ISSN: 1528-1159.

(Continued)

*Primary Examiner* — Elizabeth C. Kemmerer
(74) *Attorney, Agent, or Firm* — Lerner, David, Littenberg, Krumholz & Mentlik, LLP

(57) ABSTRACT

A method of classifying a subject having idiopathic scoliosis (IS) or at risk of developing IS comprising: determining the cellular response to Gi stimulation in a cell sample from the subject in the presence of OPN; determining the cellular response to Gi stimulation in a cell sample from the subject in the absence of OPN; and comparing the cellular response obtained in the presence of OPN with the cellular response obtained in the absence of OPN, whereby the comparing step enables the classification of the subject into one IS functional group. Also provided is the use of the foregoing method to classify borderline subjects and kits for applying the methods.

18 Claims, 83 Drawing Sheets

(56) References Cited

FOREIGN PATENT DOCUMENTS

| | | |
|---|---|---|
| WO | 2014201557 A1 | 12/2014 |
| WO | 2014201560 A1 | 12/2014 |
| WO | 2014201561 A1 | 12/2014 |
| WO | 2015032004 A1 | 3/2015 |
| WO | 2015032005 A1 | 3/2015 |

OTHER PUBLICATIONS

Akoume, M.Y. et al., "From melatonin to systemic Gi signaling defect: a hopeful odyssey for adolescent idiopathic scoliosis", Scoliosis vol. 5 (suppl. 1), p. 017, May 20-22, 2010, ISSN: 1748-7161, Canada.

Asher et al., "Adolescent idiopathic scoliosis: natural history and long term treatment effects", Scoliosis, 1:2, published: Mar. 31, 2006, pp. 1-10.

Azeddine et al., "Molecular determinants of melatonin signaling dysfunction in adolescent idiopathic scoliosis", Clinical Orthopaedics and Related Research, No. 462, pp. 45-52, Sep. 2007.

Bunnell, W.P., "Selective screening for scoliosis", Clinical Orthopaedics and Related Research, No. 434, pp. 40-45, May 2005.

Campbell, "Monoclonal Antibody Technology: The production and characterization of Rodent and Human Hybridomas", Elsevier Science Publisher, 2000, Amsterdam, The Netherlands.

Chalmers et al., "Predicting the outcome of brace treatment for scoliosis using conditional fuzzy clustering", IEEE, Sep. 2013, pp. 837-842.

Chowanska et al., "School screening for scoliosis: can surface topography replace examination with scoliometer? Scoliosis", 7(9), 1748-7161 (2012).

Donzeau et al., Methods in Molecular Biology: vol. 378, 2007, pp. 15-31.

Enneking et al., "Pathological changes in scoliosis", The Journal of Bone and Joint Surgery, vol. 51, No. 1, Jan. 1969, pp. 165-184.

Fong et al., "A meta-analysis of the clinical effectiveness of school scoliosis screening", Spine, vol. 35, No. 10, pp. 1061-1071, 2010.

Huang et. al., Analyst, 2008, 133(5): 643-648.

International Search Report for Application No. PCT/CA2014/050852 dated Dec. 4, 2014.

International Search Report for Application No. PCT/CA2014/050853 dated Dec. 5, 2014.

Julien et al., "Towards a comprehensive diagnostic assay for scoliosis", Personnalized Medecine, 2013, 10(1), 97-103.

Kane, W.J., "Scoliosis Prevalence: a call for a statement of terms", Clinical Orthopaedics and Related Research, 126, 43-46, Feb. 28, 1977, Chicago, Illinois.

Kim et al., "Scoliosis imaging: what radiologists should know", Radiographics, 30(7), 1823-1842, Nov.-Dec. 2010.

Kohler et al., "Continuous cultures of fused cells secreting antibody of predefined specificity", Nature, 256: 495-497, Aug. 7, 1975.

Letellier et al., "Estrogen cross-talk with the melatonin signaling pathway in human osteoblasts derived from adolescent idiopathic scoliosis patients", Journal of Pineal Research 45(4): 383-393, Received: Feb. 29, 2008, Accepted: Apr. 29, 2008, Canada.

Letellier, K. et al., "Récent progrès dans l'étiopathogénie de la scoliose idiopathique de l'adolescent et nouveaux concepts moléculaires", Medecine/Science Nov. 2007, vol. 23, pp. 910-916, ISSN: 0767-0974 (English translation of Summary provided).

Medhurst et al., "Pharmacological and immunohistochemical characterization of the APJ receptor and its endogeneous ligand apelin", 2003, Journal of Neurochemistry, 84, pp. 1162-1172.

Miller, N.H., "Cause and natural history of adolescent idiopathic scoliosis", Orthopedic Clinics of North America, vol. 30, No. 3, pp. 343-352, Jul. 1999, Baltimore, Maryland.

Moreau, A. et al., "Melatonin signaling dysfunction in adolescent idiopathic scoliosis", Spine vol. 29, No. 16, pp. 1772-1781, ISSN: 1528-1159, 2004.

Moreau, A. et al., "Pediatric scoliosis predictive blood tests: progress and challenges for clinicians", Scoliosis (2010), vol. 5 (Suppl 1) p. 03, ISSN: 1748-7161.

Nachemson et al., "Effectiveness of treatment with a brace in girls who have adolescent indiopathic scoliosis", The Journal of Bone and Joint Surgery, vol. 77-A, No. 6, Jun. 1995, pp. 815-822.

Nachemson, Alf, "A long term follow-up study of non-treated scoliosis", Acta Orthopaedica Scandina, 39 (4), 466-476 (1968), DOI: 10.3109/17453676808989664, Gothenburg, Sweden.

Nagao, M. et al., "Sympathetic control of bone mass regulated by osteopontin", P.NA.S., vol. 108, No. 43, pp. 17767-17772, Oct. 25, 2011, ISSN: 1091-6490.

Nash et al., "Risks of exposure to X-rays in patients undergoing long-term treatment for scoliosis", J Bone Joint Surg Am, 61 (3), 371-400, Apr. 1979 (providing Abstract only).

Niswender et. al., "A novel assay of Gi/o-linked G protein-coupled receptor coupling to potassium channels provides new insights into the pharmacology of the group III metabotropic glutamate receptors", Molecular Pharmacology, 2008, 73(4), pp. 1213-1224.

Peters et. al., "Evaluation of cellular dielectric spectroscoy, a Whole-Cell, Label-Free Technology for Drug Discovery on Gi-Coupled GPCRs", Published online on Feb. 16, 2007, Journal of Biomolecular Screening 12(3): 312-319.

Richards et al., "Standardization of criteria for adolescent idiopathic scoliosis brace studies: SRS Committee on Bracing and Nonoperative Management", Spine (Phila Pa 1976), Sep. 15, 2005; 30(18):2068-2075.

Riobo et. al., "Activation of heterotrimeric G proteins by smoothened", Aug. 15, 2006, Proc Natl Acad Sci USA, 103(33):12607-12612.

Saugstad et. al., "Metabotropic glutamate receptors activate G-Protein-Coupled inwardly rectifying potassium channels in Xenopus Oocytes", Oct. 1, 1996. The Journal of Neuroscience 16(19):5979-5985.

Solly et. al., Assay Drug Dev. Technol., 2004, 2(4): 363-372.

U.S. Appl. No. 61/875,162, filed Sep. 9, 2013.

U.S. Appl. No. 61/879,314, filed Sep. 18, 2013.

Upadhyay et al., "New prognostic factors to predict the final outcome of brace treatment in adolescent idiopathic scoliosis", Spine, 20(5), Mar. 1, 1995 (Mar. 1, 1995), pp. 537-545 (providing Abstract only).

Verdonk et al., "Cellular dielectric spectroscopy: a label-free comprehensive platform for functional evaluation of endogenous receptors", Assay Drug Development Technologies, vol. 4, No. 5, 609-619 (2006).

Wong et al., "Idiopathic scoliosis in Singapore schoolchildren: a prevalence study 15 years into the screening program", Spine (Phila Pa 1976). vol. 30, No. 10, pp. 1188-1196 (2005).

Wong, Guoruey, "Étude de la mécanotransduction dans la scoliose idiopathique de l'adolescence (SIA)", Département de Sciences Biomédicales Faculté de Médecine, Dec. 2011, 172 pages.

Xu et al., "Potential genetic markers predicting the outcome of brace treatment in patients with adolescent idiopathic scoliosis" Eur Spine J (2011) 20:1757-1764.

Supplementary European Search Report for Application No. EP14842898 dated Apr. 24, 2017.

Schack et al., Considerable variation in the concentration of osteopontin in human milk, bovine milk, and infant formulas, Journal of Dairy Science, Nov. 2009, pp. 5378-5385, vol. 92, No. 11. (Submitted with Abstract only.).

Elbakry, Mohamed, Déterminants moléculaires de la scoliose idiopathique de l'adolescent, Université de Montréal Faculté de médecine, May 2013, pp. 1-255, Retrieved from the Internet: URL: https://papyrus.bib.umontreal.ca/xmlui/bitstream/handle/1866/11338/Elbakry_Mohamed_2013_these.pdf?sequence=2 [retrieved on Apr. 10, 2017]. (Submitted with English translation of Abstract only).

U.S. Office Action for U.S. Appl. No. 14/917,786, dated May 12, 2017.

U.S. Office Action for U.S. Appl. No. 14/917,786, dated Aug. 8, 2017.

Lonstein et al., The Milwaukee brace for the treatment of adolescent idiopathic scoliosis. A review of one thousand and twenty patients, The Jouirnal of Bone and Joint Surgery. American Volume, Aug. 1994, vol. 76, Issue 8, pp. 1207-1221.

European Office Action in EP14842237.1 dated Dec. 21, 2017.

European Office Action in EP14842898.0 dated Feb. 8, 2018.

(56) References Cited

OTHER PUBLICATIONS

U.S. Office Action in U.S. Appl. No. 14/917,757 dated Mar. 28, 2018.
Crouch M F et al: "Gialpha and Gibeta are part of a signalling complex in Balb/c3T3 cells: Phosphorylation of Gibeta in growth factor-activated fibroblasts", Cellular Signalling, Elsevier Science Ltd, GB, vol. 5, No. 1, Jan. 1, 1993 (Jan. 1, 1993), pp. 41-52.
Evans G A et al: "Functional classification and orthopaedic management of spinal muscular atrophy", Journal of Bone and Joint Surgery, British Volume, Livingstone, London, GB, [On1line] Vol. 63B, No. 4, Jan. 1, 1981 (Jan. 1, 1981), pp. 516-522.
Kon S et al: "Mapping of functional epitopes of osteopontin by monoclonal antibodies raised against defined internal sequences", Journal of Cellular Biochemistry, Wiley-Liss Inc, US, vol. 84, No. 2, Oct. 15, 2001 (Oct. 15, 2001), pp. 420-432.
Supplementary European Search Report for Application No. 14842237.1 dated Feb. 24, 2017.

* cited by examiner

FIGURE 3

| Patients | Viability (%) | Cell concentration (×10⁶/mL) | Comments |
|---|---|---|---|
| 343 | 88,7 | 11,64 | |
| 344 | 90,5 | 13,6 | |
| 345 | 94,4 | 8,54 | |
| 346 | 94,3 | 25,79 | |
| 347 | 94,2 | 27,36 | |
| 348 | 94,6 | 8,52 | |
| 349 | 91,2 | 0,82 | Insufficient number of cells |
| 350 | 90,3 | 8,92 | |
| 352 | 92,6 | 8,28 | |
| 353 | 91,3 | 12,75 | |
| 354 | 86,9 | 7,62 | |
| 355 | 91,2 | 7,51 | |
| 356 | 90,3 | 9,36 | |
| 358 | 95,1 | 16,94 | |
| 359 | 92,3 | 13,89 | |
| 360 | 89,4 | 7,67 | |
| 361 | 93,5 | 7,84 | |
| 365 | 86,5 | 2,2 | Insufficient number of cells |
| 368 | 92,6 | 15,69 | |
| 369 | 93,4 | 10,9 | |
| 370 | 92,5 | 19,93 | |
| 371 | 88,8 | 10,68 | |
| 374 | 93,9 | 16,86 | |
| 376 | 92,9 | 15,67 | |
| 377 | 93,1 | 9,99 | |
| 378 | 93,6 | 13,57 | |
| 379 | 92,6 | 19,86 | |
| 380 | 91,1 | 8,46 | |
| 381 | 93,9 | 14,82 | |
| 382 | 92,1 | 23,06 | |
| 383 | 92,9 | 11,82 | |
| 384 | 89,1 | 7,73 | |

Figure 8

| Adenosine receptors | | |
|---|---|---|
| Subtype | Coupling | Reference |
| A1 | Gi | Fredholm et al., 2001 |
| A3 | Gi | |

| Adrenoreceptors | | |
|---|---|---|
| Subtype | Coupling | Reference |
| Alpha2 | Gi | |

| Angiotensin receptors | | |
|---|---|---|
| Subtype | Coupling | Reference |
| At1 | Gi / Gq | Gasparo et al., 2000 in Pharmacol. Rev. 52 (3) |
| At2 | Gi | |

| Apelin receptors | | |
|---|---|---|
| Subtype | Coupling | Reference |
| APJ | Gi | Iturrios et al., 2007 In: Arch Mal Coeur Vaiss.100 (8) |

| Bradykinin receptors | | |
|---|---|---|
| Subtype | Coupling | Reference |
| B2 | Gi / Gq | Leeb-Lundberg et al., 2005 in Pharmacol. Rev. 54 (1) |

Figure 8(continued)

| Cannabinoid receptors | | |
|---|---|---|
| Subtype | Coupling | References |
| CB2 | Gi | Pacher et al., 2006<br>In Pharmacol. Rev. 58 (3) |
| Calcium-sensing receptors | | |
| Subtype | Coupling | References |
| CaS | Gi /Gq | Chang et al.,1998<br>In: J Bone Miner Res., 13, |
| GPRC$_6$ | | |
| Chemokine receptors | | |
| Subtype | Coupling | Reference |
| CCR | Gi / Gq | Murphy et al., 2000<br>In Pharmacol. Rev. 52 (1): |
| CXCR | | |

| Dopamine receptors | | |
|---|---|---|
| Subtype | Coupling | References |
| D2 | Gi | |
| D3 | Gi | |
| D4 | Gi | |
| Frizzled receptors | | |
| Subtype | Coupling | References |
| FZD2 | Gi /Gq | *Ma and Wang* 2007<br>*In: J Biol Chem*, 282 |
| SMO | Gi | *Riobo* et a., 2006<br>In: *Proc Natl Acad Sci.* 103 |

Figure 8(continued)

| Free fatty acid receptors | | |
|---|---|---|
| Subtype | Coupling | References |
| FFA2 | Gi / Gq | Le Poul et al., 2003 |
| FFA3 | | In: J Biol Chem, 278, |

| Galanin receptors | | |
|---|---|---|
| Subtype | Coupling | References |
| GAL1 | Gi | Lang et al., 2007 |
| GAL2 | | In: Pharmacology and |
| GAL3 | | therapeutic 115 (2) |

| GABAB receptors | | |
|---|---|---|
| Subtype | Coupling | References |
| GABA | Gi | Barnard et 1998 |
| | | In:Pharmacol. Rev.50 (2) |

| Histamine receptors | | |
|---|---|---|
| Subtype | Coupling | Reference |
| H3 | Gi | Hill et al., 1997 |
| H4 | | In pharmacol. Rev. 49 (3) |

| Serotonin receptors | | |
|---|---|---|
| Subtype | Coupling | Reference |
| 5HT1 | Gi | *Hoyer et 1994* |
| 5HT5 | Gi | *In Pharmacol. Rev.* 46 *(2)* |

Figure 8(continued)

| Leukotriene receptors | | |
|---|---|---|
| Subtype | Coupling | Reference |
| LTB | Gi / Gq | Nabe et al., 1994<br>Prostaglandins Leukot. Essent. Fatty Acids |
| OXE | Gi | |
| Lysophospholipid receptors | | |
| Subtype | Coupling | Reference |
| LPA | Gi / Gq | |
| SP | Gi | |

| Neuropeptide W/neuropeptide B receptors | | |
|---|---|---|
| Subtype | Coupling | References |
| NPBW1 | Gi | Fujii et al., 2002<br>In: J. Biol. Chem. 277 |
| NPBW2 | Gi | Brezillon et al., 2003<br>In: J. Biol. Chem. 278 |

Figure 8(continued)

| Metabotropic glutamate receptors | | |
|---|---|---|
| Subtype | Coupling | Reference |
| mGLu2 | Gi | Tanabe et al., 1992<br>In: Neuron 8 |
| mGLu3 | Gi | Kingston et al.,1998<br>In: Neuropharmacology 37 |
| mGLu4 | Gi/Gq | *Tanabe 1993*<br>*In: J Neurosci.*, 13; Brabet et al., 1998 In: Neuropharmacology 37 |
| mGLU6 | Gi | Laurie et al., 1997<br>In: Neuropharmacology 36 |
| mGLu7 | Gi/Gq | Kingston et al.,1998<br>In: Neuropharmacology 37;<br>Abe *et al.*, 1992<br>In: J Biol. Chem. 267 |
| mGLu8 | Gi | Wu *et al.*, 1998<br>In: Brain Res. Mol. Brain Res., 53, |

Figure 8(continued)

| Neuropeptide Y receptors | | |
|---|---|---|
| Subtype | Coupling | References |
| Y1 | Gi/Gq | Krause et al., 1992 In: Mol. Pharmacol. 41; Herzog et al., 1992 In: Proc. Natl. Acad. Sci. 89 |
| Y2 | Gi/Gq | Shigeri and Fujimoto 1994 In:J. Biol. Chem. 269; Lynch et al., 1994 In: J. Biol. Chem. 269 |
| Y4 | Gi/Gq | Bard et al., 1995 In:J. Biol. Chem. 270 |
| Y5 | Gi | Gerald et al., 1996 In: Nature, 382 |
| Neuropeptide FF/ AF receptors | | |
| Subtype | Coupling | References |
| NPFF1 | Gi | Hinuma et al., 2000 In: Nat Cell Biol 2 |
| NPFF2 | Gi | Elshourbagy et al., 2000 In: J. Biol. Chem. 275 |
| Nicotinic acid receptor family | | |
| GPR81 | Gi | Wise et al., 2003 In: J. Biol. Chem. 278 |
| GPR109A | Gi | Soga et al., 23003 Biochem Biophys Res Commun, 303 |
| GPR109B | Gi | Jung et al., 2007. In: J. Med Chem. 50 |

Figure 8(continued)

| Opioid receptors | | |
|---|---|---|
| Subtype | Coupling | References |
| δ | Gi | Sharma et al., 1977<br>In:Proc Natl Acad Sci 74 |
| κ | Gi | Lawrence and Bidlack 1993<br>J Pharmacol Exp Ther, 266, |
| μ | Gi | Yu et al., 1990<br>J Neurochem, 55 |
| Orexin receptors | | |
| Subtype | Coupling | References |
| $OX_1$ | Gi / Gq | Holmqvist et al., 2005<br>In: J Biol Chem, 280 |
| P2Y receptors | | |
| Subtype | Coupling | References |
| P2Y12 | Gi | Hollopeter et al., 2001 Nature, 409 |
| P2Y13 | Gi | Marteau et al., 2003. In: Mol Pharmacol, 64, |
| P2Y14 | Gi | Scrivens and Dickenson 2005<br>Br J Pharmacol, 146 |

| Prostanoid receptors | | |
|---|---|---|
| Subtype | Coupling | References |
| DP2 | Gi | *Sawyer* et al., 2002<br>In: *Br J Pharmacol*, 137 |

| Somatostatin receptors | | |
|---|---|---|
| Subtype | Coupling | References |
| SST1 | Gi | Rivier et al., 2001.,J Med Chem, 44, |
| SST2 | | Nunn et al., 2003, Eur J Pharmacol, 465 |
| SST3 | | Poitout et al., 2001J Med Chem, 44 |
| SST4 | | Liu et al., 1998, J Med Chem, 41 |

Figure 9

Ligands of Receptors Coupled to Gi Protein

Adenosine A1 receptor

| Agonists | References | Antagonists | References |
|---|---|---|---|
| (R,S)-PHPNECA | Volpini et al., 2002 J Med Chem, 45 | AS100; AS70; | Varani, K., et al., 2005 Biochem Pharmacol, 70 |
| (R)-PIA | Rivkeeset al., 1999, J. Biol. Chem., 274 | caffeine | Deckert, ET AL.,1993 Neurosci Lett, 150 |
| (S)-PIA | Jockers, et al., 1994 ,J Biol Chem, 269, | CGS 15943 | Ongini, ET AL., 1999, Naunyn Schmiedebergs Arch. Pharmacol., 359, |
| CCPA | Obiefuna et al 2005 J Pharmacol Exp Ther, 315, | CPT | Dalpiaz, ET AL., 1998, Biochem Pharmacol, 56 |
| CGS 21680 | Gao et al., 2004 Biochem Pharmacol, 68 | DPCPX, Flavanone | Rivkees, ET AL., 1999, J. Biol. Chem., 274 |
| 2-chloroadenosine | Rivkeeset al., 1999 J. Biol. Chem., 274 | FR194921 galangin | Karton, et AL., 1996 J Med Chem, 39 |
| | | | Maemoto, et al., 2004 J Pharmacol Sci, 96, |
| | | | Karton, et AL., 1996 J Med Chem, 39 |
| CV-510 | Peterman and Sanoski, () Cardiol Rev, 13 | IBMX | Jockerset al.,1994, J Biol Chem, 269 |
| cyclopentyladenosine | Rivkeeset al., 1999 J. Biol. Chem., 274 | L-97-1 | Obiefuna, et al., 2005, J Pharmacol Exp Ther, 315 |
| | | morin | Karton, et AL., 1996 J Med Chem, 39 |
| 2-hexynyl-NECA | Volpini et al., 2002 J Med Chem, 45 | MRE 2029F20 | Varani, et al., 2005, Biochem Pharmacol, 70 |
| | | MRS1041, sakuranetin | Karton, et AL., 1996 J Med Chem, 39 |
| LUF5831 | Heitman, et al., 2006 Br J Pharmacol, 147 | SCH 58261 | Ongini, et al., 1999, Naunyn Schmiedebergs Arch. Pharmacol., 359 |
| NECA | Rivkeeset al., 1999 J. Biol. Chem., 274 | Theophylline XAC | Jockers, et al., 1994, J Biol Chem, 269 |
| PENECA | Volpini et al., 2002 J Med Chem, 45 | ZM 241385 | Ongini, et al., 1999, Naunyn Schmiedebergs Arch. Pharmacol., 359 |

Figure 9 (continued)

| Adenosine A3 receptor | | | |
|---|---|---|---|
| Agonists | References | Antagonists | References |
| (R,S)-PHPNECA | Volpini et al., 2002 J Med Chem, 45 | (R)-niguldipine | van Rhee et al., 1996 J Med Chem, 39 |
| (R)-PIA | Olah et al., 1994 J Biol Chem, 269 | (R,S)-nicardipin | |
| (S)-PIA | | BW-A1433 | Salvatoreet al.,1993 Proc. Natl. Acad. Sci. 90 |
| AB-MECA | Arani et al., 2000 Mol Pharmacol, 57 | CGS 15943 | Varani et al., 2000 Mol Pharmacol, 57 |
| [125I]AB-MECA | | DPCPX | Olah et al., 1994 J Biol Chem, 269 |
| [3H]AB-MECA | Olah et al., 1994 J Biol Chem, 269 | Flavone, Flavanone, galagnin | Karton et al., 1996 J Med Chem, 39 |
| [3H]APNEA | Zhou et al., 1992 Proc. Natl. Acad. Sci. 89 | I-ABOPX | Salvatoreet al.,1993 Proc. Natl. Acad. Sci. 90 |
| CCPA | Klotz et al.,1998 Naunyn Schmiedebergs Arch. Pharmacol., 357 | MRE 3008F20, [3H]MRE 3008F20 | Varani et al., 2000 Mol Pharmacol, 57 |
| CGS 21680 | | | Karton et al.,1996, J Med Chem, 39 |
| Cl-IB-MECA | Jacobson et al., 1997 Neuropharmacology, 36 | MRE 3010F20, RS1041, | Jacobson et al., 1997 Neuropharmacology, 36 |
| cyclopentyladenosine | Salvatoreet al.,1993 Proc. Natl. Acad. Sci. 90 | MRS1042 MRS1067, MRS1088, MRS1093, MRS1097, MRS1177 | van Rhee et al., 1996, J Med Chem, 39 |
| 2-hexynyl-NECA | Volpini et al., 2002 J Med Chem, 45 | MRS1186, MRS1191 MRS1191, MRS1220 MRS1476, MRS1486 | Kim et al.,1996 J Med Chem, 39, |
| I-ABA | Salvatoreet al.,1993 Proc. Natl. Acad. Sci. 90 | MRS1505, MRS1523 MRS1523, MRS928 | |

Figure 9 (continued)

| Adenosine A3 receptor | | | |
|---|---|---|---|
| Agonists | References | Antagonists | References |
| IAB-MECA, IB-MECA | Klotz et al.,1998 Naunyn Schmiedebergs Arch. Pharmacol., 357 | sakuranetin | Karton et al.,1996, J Med Chem, 39 |
| MPC-MECA | Varani et al., 2000 Mol Pharmacol, 57 | theophylline | Klotz et al.,1998 Naunyn Schmiedebergs Arch. Pharmacol., 357 |
| NECA | Jacobson et al., 1997 Neuropharmacology, 36 | visnagin | Karton et al.,1996, J Med Chem, 39 |
| [$^3$H]NECA | Feoktistov et al., 2001 Biochem Pharmacol, 62 | VUF8504 | van et al.,1998 J. Med. Chem., 41 |
| PENECA | Volpini et al., 2002 J Med Chem, 45 | VUF8507 | |
| | | XAC | Olah et al., 1994 J Biol Chem, 269 |

Figure 9 (continued)

Adrenoreceptor Alpha2A

| Agonists | References | Antagonists | References |
|---|---|---|---|
| adrenaline | | ARC-239 | Uhlén et al., 1994 J Pharmacol Exp Ther, 271 |
| apomorphine | | BRL 44408 | |
| brimonidine | | bromocriptine | Millan et al., 2002 J Pharmacol Exp Ther, 303 |
| clonidine | Asper et al., 1998 Biochem Pharmacol., 55 | cabergoline | |
| dexmedetomidine | | chlorpromazine | Devedjian et al., 1994 Eur J Pharmacol., 252, |
| guanfacine | | lisuride | Millan et al., 2002 J Pharmacol Exp Ther, 303 |
| noradrenaline | | [³H]MK-912 | Uhlén et al., 1994 J Pharmacol Exp Ther, 271 |
| oxymetazoline | | phentolamine | Devedjian et al., 1994 Eur J Pharmacol., 252 |
| pergolide | Millan et al., 2002 J Pharmacol Exp Ther, 303 | piribedil | Millan et al., 2002 J Pharmacol Exp Ther, 303 |
| xylazine | Asper et al., 1998 Biochem Pharmacol., 55 | prazosin | Devedjian et al., 1994 Eur J Pharmacol., 252 |
| | | rauwolscine | Uhlén et al., 1994 J Pharmacol Exp Ther, 27 |
| | | [³H]rauwolscine | Bylund et al., 1992 Mol Pharmacol., 42 |
| | | RX821002 | Uhlén et al., 1994 J Pharmacol Exp Ther, 271 |
| | | spiroxatrine | |
| | | terguride | Millan et al., 2002 J Pharmacol Exp Ther, 303 |
| | | WB 4101 | |
| | | yohimbine | Uhlén et al., 1994 J Pharmacol Exp Ther, 271 |

Figure 9 (continued)

Adrenoreceptor Alpha2B

| Agonists | References | Antagonists | References |
|---|---|---|---|
| adrenaline | | apomorphine | Millan, et al., 2002 *J Pharmacol Exp Ther*, 303 |
| brimonidine | | ARC-239 | Bylund, et al., 1992 *Mol Pharmacol.*, 42 |
| clonidine | | BRL 44408 | Uhlén et al., 1994 *J Pharmacol Exp Ther*, 271 |
| dexmedetomidine | Jasper et al., 1998 *Biochem Pharmacol.*, 55 | bromocriptine | |
| guanfacine | | cabergoline | Millan, et al., 2002 *J Pharmacol Exp Ther*, 303 |
| noradrenaline | | chlorpromazine | Millan, et al., 2002 *J Pharmacol Exp Ther*, 303 |
| oxymetazoline | | lisuride | Millan, et al., 2002 *J Pharmacol Exp Ther*, 303 |
| pergolide | Millan, et al., 2002 *J Pharmacol Exp Ther*, 303 | [³H]MK-912 | Uhlén et al., 1994 *J Pharmacol Exp Ther*, 271 |
| xylazine | Jasper et al., 1998 *Biochem Pharmacol.*, 55 | phentolamine | Bylund, et al., 1992 *Mol Pharmacol.*, 42, |
| | | prazosin | |
| | | rauwolscine | Uhlén et al., 1994 *J Pharmacol Exp Ther*, 271 |
| | | roxindole | |
| | | RX821002 | Millan, et al., 2002 *J Pharmacol Exp Ther*, 30 |
| | | spiroxatrine | Uhlén et al., 1994 *J Pharmacol Exp Ther*, 271 |
| | | terguride | Millan, et al., 2002 *J Pharmacol Exp Ther*, 30 |
| | | WB 4101 | |
| | | yohimbine | Bylund, et al., 1992 *Mol Pharmacol.*, 42, |

Figure 9 (continued)

Adrenoreceptor Alpha2C

| Agonists | References | Antagonists | References |
|---|---|---|---|
| adrenaline | | apomorphine | Millan et al., 2002 *J Pharmacol Exp Ther*, 303 |
| brimonidine | | ARC-239 | Bylund et al., 1992, *Mol Pharmacol.*, 42, |
| clonidine | | BRL 44408 | Uhlén et al., 1994, *J Pharmacol Exp Ther*, 271 |
| dexmedetomidine | Jasper et al., 1998 *Biochem Pharmacol.*, 55 | bromocriptine | Millan, et al., 2002 *J Pharmacol Exp Ther*, 303 |
| guanfacine | | cabergoline | |
| noradrenaline | | chlorpromazine | Bylund et al., 1992, *Mol Pharmacol.*, 42, |
| Oxymetazoline | | lisuride | Millan, et al., 2002 *J Pharmacol Exp Ther*, 303 |
| Pergolide | Millan, et al., 2002 *J Pharmacol Exp Ther*, 303 | [$^3$H]MK-912 | Uhlén et al., 1994, *J Pharmacol Exp Ther*, 271 |
| xylazine | Jasper et al., 1998 *Biochem Pharmacol.*, 55 | phentolamine | Bylund et al., 1992, *Mol Pharmacol.*, 42, |
| | | Piribedil, prazosin | Millan, et al., 2002 *J Pharmacol Exp Ther*, 303 |
| | | rauwolscine | |
| | | roxindole | Uhlén et al., 1994, *J Pharmacol Exp Ther*, 271 |
| | | RX821002 | Millan, et al., 2002 *J Pharmacol Exp Ther*, 303 |
| | | spiroxatrine | Uhlén et al., 1994, *J Pharmacol Exp Ther*, 271 |
| | | Terguride, WB 4101 | Millan, et al., 2002 *J Pharmacol Exp Ther*, 303 |
| | | yohimbine | Uhlén et al., 1994, *J Pharmacol Exp Ther*, 271 |

Figure 9 (continued)

Angiotensin AT2 receptors

| Agonists | References | Antagonists | References |
|---|---|---|---|
| ang I | Whitebread et al., 1989 Biochem. Biophys. Res. Commun., 163 | PD123177 | Chiu et al., 1989 Biochem. Biophys. Res. Commun., 165 |
| ang II | Speth and Kim 1990 Biochem. Biophys. Res. Commun., 169 | PD123319 | West et al., 1991 J. Cardiovasc. Pharmacol., 17 |
| [p-aminoPhe6] ang II | | | |
| ang III | Whitebread et al., 1989 Biochem. Biophys. Res. Commun., 163 | Saralasin | Chiu et al., 1989 Biochem. Biophys. Res. Commun., 165 |
| CGP42112 | | | |

Apelin receptor

| Agonists | References | Antagonists | References |
|---|---|---|---|
| [$^3$H](Pyr$^1$)[Met(O)11]-apelin-13 | Medhurst et al., 2003 J Neurochem., 84, | ALX40-4C | Zhou et al., 2003 Virology., 307 |
| [$^{125}$I](Pyr$^1$)[Nle$^{75}$,Tyr$^{77}$]-apelin-13 | Hosoya et al., 2000 J Biol Chem., 275 | | |
| [$^{125}$I](Pyr$^1$)apelin-13 | Katugampola et al., 2001 Br J Pharmacol., 132 | | |
| [$^{125}$I][Nle$^{75}$,Tyr$^{77}$]apelin-36 | Medhurst et al., 2003 J Neurochem., 84, | | |
| apelin-13 | Medhurst et al., 2003 J Neurochem., 84, | | |
| apelin-36 | | | |
| Pyr$^1$-apelin-13 | | | |

Figure 9 (continued)

Cannabinoid CB2 receptors

| Agonists | References | Antagonists | References |
|---|---|---|---|
| Δ⁹-THC | Felder et al., 1995 *Mol. Pharmacol.*, 48 | | |
| arachidonoyl ethanolamide | | | |
| 2-arachidonoylglycerol | Mechoulam et al., 1995 *Biochem. Pharmacol.*, 50 | | |
| CP55940 | | AM630 | |
| [³H]CP55940 | Felder et al., 1995 *Mol. Pharmacol.*, 48 | | |
| HU-210 | Hanus et al., 1999 *Proc. Natl. Acad. Sci.* 96 | | Ross et al., 1999 *Br. J. Pharmacol.*, 126 |
| HU-308 | Huffman et al., 1999, *Bioorg. Med. Chem.*, 7 | | |
| JWH-133 | | | |
| L-759,633 | Ross et al., 1999 *Br. J. Pharmacol.*, 126 | SR144528 | |
| WIN55212-2 | Felder et al., 1995 *Mol. Pharmacol.*, 48 | | |
| [³H]WIN55212-2 | Munro et al., 1993 *Nature*, 365 | | |

Figure 9 (continued)

Calcium-sensing CaS receptors

| Agonists | References | Antagonists | References |
|---|---|---|---|
| Ca²⁺ | | 1-arylmethylpyrrolidin-2-yl ethanol amines | Gavai et al., 2005 *Bioorg Med Chem Lett*, 15 |
| Mg²⁺ | Riccardi et al., 1995 *Proc Natl Acad Sci* 92 | 2-benzylpyrridine-substituted aryloxypropanols | Yang et al., 2005 *Bioorg Med Chem Lett*, 15 |
| Neomycin and other aminoglycosides | | Calhex 231 | Petrel et al., 2003 *J Biol Chem.*, 278 |
| spermine | Quinn et al., 1997 *Am J Physiol*, 273 | 2-methyl-3-phenethyl-3H-pyrimidin-4-ones | Shcherbakova et al., 2005 *Bioorg Med Chem Lett*, 15 |
| | | N(1)-Arylsulfonyl-N(2)-(1-(1-naphthyl)ethyl)-1,2-diaminocyclohexane | Kessler et al., 2004, *Chembiochem.*, 5 |
| | | NPS 2143 | Nemeth et al., 2001 *J Pharmacol Exp Ther.*, 299 |

Figure 9 (continued)

| Chemokine CCR1 receptors | | | |
|---|---|---|---|
| Agonists | references | Antagonists | References |
| BP-CCL3 | Zoffmann et al., 2001, J Med Chem, 44 | BX 471 | Liang et al., 2000, J Biol Chem, 275 |
| CCL14 | Chou et al., 2002, Br J Pharmacol, 137 | | |
| CCL15 | Coulin et al., 1997, Eur J Biochem, 248 | | |
| [$^{125}$I]CCL2 | Sarau et al., 1997, J Pharmacol Exp Ther, 283 | vMIP-II | Kledal et al., 1997, Science, 277 |
| CCL23 | | | |
| CCL3 | Chou et al., 2002, Br J Pharmacol, 137 | | |
| CCL4 | | | |
| CCL5 | Combadiere et al., 1995, J Biol Chem, 270 | | |
| CCL7 | Chou et al., 2002, Br J Pharmacol, 137 | | |
| [$^{125}$I]CCL8 | Gong et al., 1997, J Biol Chem, 272 | | |
| Flu-CCL3 | Zoffmann et al., 2001, J Med Chem, 44 | | |
| MIP-1δ | Chou et al., 2002, Br J Pharmacol, 137 | | |

Figure 9 (continued)

| Dopamine D2 receptor | | | |
|---|---|---|---|
| Agonists | References | Antagonists | References |
| 6,7-ADTN | | (+)-butaclamol | |
| apomorphine | | chlorpromazine | |
| bromocriptine | Lajiness etal., 1993, *J. Pharmacol. Exp. Ther.*, 267 | clozapine | |
| Dopamine | | domperidone | |
| lisuride | Sautel et al., 1995, *Neuroreport*, 6 | fluphenazine | Eorge et al., 1985, *Endocrinology*, 117 |
| (-)-N-propylnorapo-morphine | | haloperidol | |
| 7-OHDPAT | Eorge et al., 1985, *Endocrinology*, 117 | nemonapride | |
| pergolide | | spiperone | |
| PD128907 | | S-sulpiride | |
| quinelorane | | | |
| quinpirole | | | |

Figure 9 (continued)

Dopamine D3 receptor

| Agonists | References | Antagonists | References |
|---|---|---|---|
| apomorphine | | U99194A | Waters et al., 1993 *J. Neural Transm. Gen. Sect.*, 94 |
| BP 897 | | | |
| bromocriptine | | nafadotride | Sautel et al., 1995 *J. Pharmacol. Exp. Ther.*, 275 |
| Dopamine | Sautel et al., 1995 *Neuroreport*, 6 | | |
| 7-OHDPAT | | | |
| PD128907 | Chio et al., 1994 *J. Biol. Chem.*, 269 | | |
| pramipexole | | | |
| quinelorane | | | |
| quinpirole | | | |

Figure 9 (continued)

| Dopamine D4 receptor | | | |
|---|---|---|---|
| Agonists | References | Antagonists | References |
| (-)-apomorphine | | CP293019 | Sanner et al., 1998 *Bioorg. Med. Chem.*, 8 |
| bromocriptine | Chio et al., 1994 *J. Biol. Chem.*, 269, | L745870 | Bristow et al., 1997 *Trends Pharmacol. Sci.*, 18 |
| di-propyl-ADTN | | NGD941 | Tallman et al., 1997 *J. Pharmacol. Exp. Ther.*, 282 |
| dopamine | | U101387 | Merchant et al., 1996 *J. Pharmacol. Exp. Ther.*, 279 |
| lisuride | Newman-Tancredi et al., 1997 *J. Pharmacol. Exp. Ther.*, 282 | YM50001 | Hidaka et al., 1996 *Neuroreport*, 7 |
| pergoline | | clozapine | |
| peribedil | | | |
| quinelorane | | | |
| quinpirole | | | |

Figure 9 (continued)

| Frizzled FZD2 receptor | |
|---|---|
| Agonists | references |
| WNT-5A | Ma and Wang, 2007
*J Biol Chem*, 282 |

| Frizzled SMO receptor | |
|---|---|
| Agonists | references |
| Oxysterols | Corcoran and Scott 2006
*Proc Natl Acad Sci U S A*, 103 |

| Free fatty acid FFA2 receptor | |
|---|---|
| Agonists | References |
| acetate | Nilsson et al., 2003
*Biochem Biophys Res Commun*, 303 |
| butyrate | Le Poul et al., 2003
*J Biol Chem*, 278 |
| isobutyrate | Le Poul et al., 2003
*J Biol Chem*, 278 |
| pentanoate | Brown et al., 2003
*J Biol Chem*, 278 |
| propionate | Le Poul et al., 2003
*J Biol Chem*, 278 |

| Free fatty acid FFA3 receptor | |
|---|---|
| Agonists | References |
| acetate | Brown et al., 2003
*J Biol Chem*, 278 |
| butyrate | |
| isobutyrate | Xiong et al., 2004
*Proc Natl Acad Sci*. 101 |
| pentanoate | |
| propionate | |

NB: Currently no antagonists are known for FZD2, SMO, FFA2 or FFA3

Figure 9 (continued)

GABAB receptor

| Agonists | References | Antagonists | References |
|---|---|---|---|
| (-)-baclofen | | CGP 35348 | Froestl et al., 1995 *J. Med. Chem.*, 38, |
| | | CGP 54626A | |
| APPA | | CGP 56999A | |
| | Kaupmann et al., 1997 *Nature*, 386 | CGP 62349 | |
| CGP 47656 | | CGP 64213 | Kaupmann et al., 1997 *Nature*, 386 |
| | | [$^{125}$I]-CGP 64213 | |
| GABA | | CGP 71872 | |
| | | [$^{125}$I]-CGP 71872 | |
| | | 2-OH-saclofen | |
| | | aclofen | |
| | | SCH 50911 | Bolser et al., 1995 *J Pharmacol Exp Ther.*, 274 |

Figure 9 (continued)

Histamine H3 receptor

| Agonists | References | Antagonists | References |
|---|---|---|---|
| (R)-α-methylhistamine | Lovenberg et al., 2000 *J Pharmacol Exp Ther*, 293 | 4-(3-piperdin-1-yl-propoxy)benzonitrile | Liu et al., 2001 *Mol Pharmacol*, 59 |
| (S)-α-methylhistamine | Wulff et al., 2002 *Eur J Pharmacol*, 453 | 1-[4-(3-piperidin-1-yl)propoxy)benzyl]piperidine | Apodaca et al., 2003 *J Med Chem*, 46 |
| N-[³H]α-methylhistamine | Chen et al., 2003 *Eur J Pharmacol*, 467 | A-304121, A-317920, ABT-239 | Esbenshade et al., 2004 *Biochem Pharmacol*, 68 |
| N-α-methylhistamine | Liu et al., 2001 *Mol Pharmacol*, 59 | Burimamide, | Liu et al., 2001 *Mol Pharmacol*, 59 |
| dimaprit | Wulff et al., 2002 *Eur J Pharmacol*, 453 | | |
| GR 175737, Perceptin©, proxyfan | Chen et al., 2003 *Eur J Pharmacol*, 467 | ciproxifan | Rouleau et al., 2004 *J Neurochem*, 90 |
| histamine | | Clobenpropit, clozapine | Lovenberg et al., 2000 *J Pharmacol Exp Ther*, 293 |
| Imbutamine, iodoproxyfan | Kitbunnadaj et al., 2003 *J Med Chem*, 46 | FUB 349, FUB 465, GT 2394 | Ligneau et al., 2000 *Br J Pharmacol*, 131 |
| imetit | Rouleau et al., 2004 *J Neurochem*, 90 | Impentamine, iodophenpropit | Wieland et al., 2001 *J Pharmacol Exp Ther*, 299 |
| immepip | Liu et al., 2001 *Mol Pharmacol*, 59 | [³I]iodoproxyfan, proxyfan | Ligneau et al., 2000 *Br J Pharmacol*, 131 |
| Impentamine, methimepip | Kitbunnadaj et al., 2003 *J Med Chem*, 46 | JB 98064 thioperamide | Wulff et al., 2002 *Eur J Pharmacol*, 453 |
| impromidine | Liu et al., 2001 *Mol Pharmacol*, 59 | VUF 4904 | Wieland et al., 2001 *J Pharmacol Exp Ther*, 299 |
| VUF 5207 | Wieland et al., 2001 *J Pharmacol Exp Ther*, 299 | | |

Figure 9 (continued)

Histamine H4 receptor

| Agonists | References | Agonists | References |
|---|---|---|---|
| 2-(3-bromophenyl)histamine | Lim et al., 2005 J Pharmacol Exp Ther, 314 | burimamide | Liu et al., 2001 J Pharmacol Exp Ther, 299 |
| (R)-α-methylhistamine | Liu et al., 2001 J Pharmacol Exp Ther, 299 | 5-chloroindole-2-piperazinecarboximide | Terzioglu et al., 2004 Bioorg Med Chem Lett, 14 |
| (S)-α-methylhistamine | Morse et al., 2001 J Pharmacol Exp Ther, 296 | ciproxifan | Esbenshade et al., 2004 Biochem Pharmacol, 68, |
| N-α-methylhistamine | | clobenpropit | |
| CCL16 | Nakayama et al., 2004 J Immunol, 173, | clozapine | Liu et al., 2001 J Pharmacol Exp Ther, 299 |
| dimaprit | Liu et al., 2001 Mol Pharmacol, 59 | iodophenpropit | Zhu et al., 2001 Mol Pharmacol, 59 |
| Histamine, imetit | Liu et al., 2001 J Pharmacol Exp Ther, 299 | JNJ 7777120 | Thurmond et al., 2004 J Pharmacol Exp Ther, 309 |
| HTMT | Zhu et al., 2001 Mol Pharmacol, 59 | [³H]pyrilamine | Nguyen et al., 2001 Mol Pharmacol, 59 |
| immepip | | thioperamide | Liu et al., 2001 J Pharmacol Exp Ther, 299 |
| improgan | | | |
| impromidine | Lim et al 2005 J, Pharmacol Exp Ther, 314 | | |
| methimepip | Kitbunnadaj et al., 2005 J Med Chem, 48, | | |
| methylhistamine | Lim et al 2005 J, Pharmacol Exp Ther, 314 | | |
| VUF 8430 | Lim et al., 2006 J Med Chem, 49 | | |

Figure 9 (continued)

| Leukotriene BLT1 receptor | | | |
|---|---|---|---|
| Agonists | References | Antagonists | References |
| 20-COOH-LTB$_4$ | Devchand et al., 1996 *Nature*, 384 | U75302 | Devchand et al., 1996 *Nature*, 384 |
| 12R-HETE | | | |
| 12-keto-LTB$_4$ | | | |
| 20-OH-LTB$_4$ | | | |
| LTB$_4$ | | | |

Figure 9 (continued)

Melatonin MT1 receptor

| Agonists | References | Antagonists | References |
|---|---|---|---|
| 2-[125I]MLT | Audinot et al., 2003 *Naunyn Schmiedebergs Arch Pharmacol*, 367 | 4P-PDOT | Audinot et al., 2003 *Naunyn Schmiedebergs Arch Pharmacol*, 367 |
| agomelatine | | | |
| 6-Cl-MLT | | | |
| GR 128107 | Teh and Sugden 1999, *Br J Pharmacol*, 126 | K185 | Faust et al., 2000 *J Med Chem*, 43 |
| GR 196429 | Browning et al., 2000 *Br. J. Pharmacol.*, 129 | | |
| 5-HEAT | Nonno et al., 2000 *J Pineal Res*, 29, 23 | luzindole | |
| 2-I-MLT | Audinot et al., 2003 *Naunyn Schmiedebergs Arch Pharmacol*, 367 | | |
| IIK7 | Faust et al., 2000 *J Med Chem*, 43 | S20928 | Audinot et al., 2003 *Naunyn Schmiedebergs Arch Pharmacol*, 367 |
| LY 156735 | Mulchahey et al., 2004 *Life Sci*, 75 | | |
| [3H]MLT | Browning et al., 2000 *Br. J. Pharmacol.*, 129 | S22153 | |
| 6-OH-MLT | | | |
| S24014 | | | |
| S24773 | Audinot et al., 2003 *Naunyn Schmiedebergs Arch Pharmacol*, 367 | S26131 | |
| S26284 | | | |
| TAK375 | Kato et al., 2005 *Neuropharmacology*, 48 | | |

Figure 9 (continued)

Metabotropic glutamate mGlu2 receptor

| Agonists | References | Antagonists | References |
|---|---|---|---|
| (1S,3R)-ACPD | Johnson et al., 1999 *Neuropharmacology.*, 38 | eGlu | Schweitzer et al., 2000 *Neuropharmacology.*, 39 |
| (2R,3R)-APDC | | LY341495 | |
| (S)-4C3HPG | Cartmell et al., 1998 *Br J Pharmacol.*, 123 | [³H]LY341495 | Johnson et al., 1999 *Neuropharmacology.*, 38 |
| DCG-IV | | (+)-MCPG | Cartmell et al., 1998 *Br J Pharmacol.*, 123 |
| L-CCG-I | Johnson et al., 1999 *Neuropharmacology.*, 38 | MGS0039 | Chaki et al., 2004 *Neuropharmacology*, 46 |
| L-glutamate | | MSOP | Cartmell et al., 1998 *Br J Pharmacol.*, 123 |
| LY354740 | | | |
| [³H]LY357740 | Schweitzer et al., 2000 *Neuropharmacology.*, 39 | | |
| LY379268 | Monn et al., 1999 *J Med Chem.*, 42 | | |
| MGS0028 | Nakazato et al., 2000 *J Med Chem*, 43 | | |

Figure 9 (continued)

Metabotropic glutamate mGlu3 receptor

| Agonists | References | Antagonists | References |
|---|---|---|---|
| (1S,3R)-ACPD | Johnson et al., 1999 *Neuropharmacology.*, 38 | eGlu | Schweitzer et al., 2000 *Neuropharmacology.*, 39 |
| (2R,4R)-APDC | | | |
| DCG-IV | Cartmell et al., 1998 *Br J Pharmacol.*, 123 | LY341495 | Johnson et al., 1999 *Neuropharmacology.*, 38 |
| L-CCG-I | Johnson et al., 1999 *Neuropharmacology.*, 38 | | |
| L-glutamate | | [³H]LY341495 | |
| [³H]LY341495 | Schweitzer et al., 2000 *Neuropharmacology.*, 39, | (+)-MCPG | Cartmell et al., 1998 *Br J Pharmacol.*, 123 |
| LY354740 | | | |
| LY379268 | Monn et al., 1999 *J Med Chem.*, 42, | MGS0039 | Chaki et al., 2004 *Neuropharmacology.*, 46 |
| NAAG | Schweitzer et al., 2000 *Neuropharmacology.*, 39 | | |

Figure 9 (continued)

Metabotropic glutamate mGlu4 receptor

| Agonists | references | Agonists | References |
|---|---|---|---|
| (R,S)-4-PPG | Gasparini et al., 1999 *J. Pharmacol. Exp. Ther.*, 289 | | |
| (S)-3,4-DCPG | Thomas et al., 2001 *Neuropharmacology*, 40 | CPPG | Han and Hampson 1999 *J Biol Chem.*, 274 |
| ACPT-I | Acher et al., 1997 *J Med Chem*, 40, | | |
| [³H]AP4 | Han and Hampson 1999 *J Biol Chem.*, 274, | LY341495 | Kingston et al., 1995 *Neuropharmacology.*, 34 |
| FP0429 | Muto et al., 2007 *Proc Natl Acad Sci U S A*, 104 | | |
| L-AP4 | Acher et al., 1997 *J Med Chem*, 40 | MAP4 | Han and Hampson 1999 *J Biol Chem.*, 274 |
| L-CCG-I | Hayashi et al., 1992 *Br J Pharmacol.*, 107 | | |
| L-glutamate | Han and Hampson 1999 *J Biol Chem.*, 274 | MPPG | |
| L-SOP | | | |

Figure 9 (continued)

Metabotropic glutamate mGlu6 receptor

| Agonists | References | Antagonists | References |
|---|---|---|---|
| (1S,3R)-ACPD | Tuckmantel et al., 1997 Bioorg Med Chem Lett., 7 | DCG-IV | Brabet et al., 1998 Neuropharmacology., 37 |
| (1S,3R)-ACPD | Laurie et al., 1997 Neuropharmacology, 36 | | |
| (2S,1S,2S)-L-CCG-I | | | |
| (R,S)-4-PPG | Thomas et al., 2001 Neuropharmacology., 40 | [³H]LY341495 | Wright et al., 2000 Naunyn Schmiedebergs Arch Pharmacol., 362 |
| (S)-3,4-DCPG | | | |
| ACPT-I | Uckmantel et al., 1997 Bioorg Med Chem Lett., 7, | MAP4 | Pin and Acher 2002 Curr Drug Targets CNS Neurol Disord., 1 |
| 1-benzyl-APDC | | | |
| L-AP4 | Laurie et al., 1997 Neuropharmacology, 36 | MPPG | Ma et al., 1997 Bioorg Med Chem Lett., 7, |
| L-glutamate | | | |
| L-SOP | Monn et al., 1999 J Med Chem., 42 | α-MSOP | Pin and Acher 2002 Curr Drug Targets CNS Neurol Disord., 1 |
| LY354740 | | | |
| LY379268 | | | |

Figure 9 (continued)

Metabotropic glutamate mGlu7 receptor

| Agonists | References | Antagonists | References |
|---|---|---|---|
| (1S,3R)-ACPD | Wright et al., 2000 *Naunyn Schmiedebergs Arch Pharmacol.*, 362 | DCG-IV | |
| | | LY341495 | |
| (R,S)-4-PPG | Gasparini et al., 1999 *J. Pharmacol. Exp. Ther.*, 289 | [³H]LY341495 | |
| L-AP4 | | MAP4 | |
| L-CCG-I | | MCCG | Wright et al., 2000 *Naunyn Schmiedebergs Arch Pharmacol.*, 362 |
| L-glutamate | Wright et al., 2000 *Naunyn Schmiedebergs Arch Pharmacol.*, 362 | (+)-MCPG | |
| | | MPPG | |
| L-SOP | | MSOP | |
| PPG | | MSOPPE | |

Figure 9 (continued)

Metabotropic glutamate mGlu8 receptor

| Agonists | References | Antagonists | References |
|---|---|---|---|
| (1S,3R)-1-ACPD | Wu et al., 1998 Brain Res. Mol. Brain Res., 53, | CPPG | Peltekova et al., 2000 Brain Res Mol Brain Res, 76 |
| (R,S)-4-PPG | Thomas et al., 2001 Neuropharmacology., 40 | | |
| (S)-3,4-DCPG | | | |
| ACPT-I | de Colle et al., 2000 Eur J Pharmacol, 394 | DCG-IV | Malherbe et al., 1999 Brain Res. Mol. Brain Res., 67 |
| [³H]AP4 | Malherbe et al., 1999 Brain Res. Mol. Brain Res., 67 | LY341495 | Kingston et al., 1998 Neuropharmacology., 37 |
| D-AP4 | Wu et al., 1998 Brain Res. Mol. Brain Res., 53 | | |
| L-AP4 | | MAP4 | Peltekova et al., 2000 Brain Res Mol Brain Res, 76 |
| L-AP4 | | | |
| L-CCG-I | | | |
| L-CCG-I | Malherbe et al., 1999 Brain Res. Mol. Brain Res., 67 | | |
| L-glutamate | | α-MSOP | Pin and Acher 2002 Curr Drug Targets CNS Neurol Disord., 1 |
| L-SOP | | | |
| LY354740 | | | |

Figure 9 (continued)

| Neuropeptide W/neuropeptide B receptors |||||
|---|---|---|---|---|
| NPBW1 || | NPBW2 ||
| Agonists | References | Agonists | References | Antagonists |
| [$^{125}$I][Tyr$^{11}$]des-Br-NPB-23 | | NPB-23 | Brezillon et al., 2003 J Biol Chem., 278 | |
| Br-NPB-29 | Fujii et al., 2002 J Biol Chem., 277 | NPB-29 | | |
| des-Br-NPB-23 | | | | |
| des-Br-NPB-29 | | [$^{125}$I]NPW | Shimomura et al., 2002 J Biol Chem., 277 | |
| NPW-23 | | NPW-23 | Brezillon et al., 2003 J Biol Chem., 278 | |
| [$^{125}$I]NPW-23 | Shimomura et al., 2002 J Biol Chem., 277 | NPW-30 | | |
| NPW-30 | | | | |

NB: No antagonists are currently available neither for NPBW1 nor for NPBW2

Figure 9 (continued)

Neuropeptide Y1 receptors

| Agonists | References | Agonists | References |
|---|---|---|---|
| [$^{125}$I]NPY | Krause et al., 1992 *Mol Pharmacol*, 41 | 1229U91 | Gehlert et al., 1997 *Peptides*, 18 |
| [$^3$H]NPY | Weng et al., 1995 *Mol Pharmacol*, 48 | BIBO3304 | Dumont and Quirion 2000 *Br J Pharmacol*, 129 |
| [Leu$^{31}$,Pro$^{34}$]-NPY | Krause et al., 1992 *Mol Pharmacol*, 41 | BIBP3226 | Gehlert et al., 1997 *Peptides*, 18 |
| [Ala$^{31}$,Aib$^{32}$]-NPY | Cabrele et al., 2002 *Biochemistry*, 41 | GR231118 | Dumont and Quirion 2000 *Br J Pharmacol*, 129 |
| NPY | Krause et al., 1992 *Mol Pharmacol*, 41 | | |
| NPY$_{2-36}$ | Gehlert, et al., 1997 *Peptides*, 18 | [$^{125}$I]GR231118 | |
| PP (rat) | | | |
| [$^{125}$I]PYY | Larhammer et al., 1992 *J Biol Chem*, 267 | SR120819A | Sjödin et al., 2006 *Biochem J*, 393 |
| PYY | Dumont and Quirion 2000 *Br J Pharmacol*, 129 | | |

Figure 9 (continued)

Neuropeptide Y2 receptors

| Agonists | References | Antagonists | References |
|---|---|---|---|
| N-α-Ac-PYY$_{25-36}$ | Goumain, et al., 2001 *Mol Pharmacol*, 60 | BIE0246 | Goumainet al., 2001 *Mol Pharmacol*, 60 |
| C2-NPY | Gerald et al., 1995 *J Biol Chem*, 270 | | |
| [$^{125}$I]NPY | Rose et al., 1995 *J Biol Chem*, 270 | | |
| [D-Trp$^{32}$]-NPY | Gehlert et al., 1996 *Mol Pharmacol*, 49 | | |
| NPY (human) | Gerald et al., 1995 *J Biol Chem*, 270 | | |
| [Leu$^{31}$,Pro$^{34}$]-NPY | | | |
| [Ala$^{31}$,Aib$^{32}$]-NPY | Cabrele, et al., 2002 *Biochemistry*, 41 | | |
| NPY$_{13-36}$ (human) | | | |
| NPY$_{16-36}$ (porcine) | | | |
| NPY$_{3-36}$ (porcine) | | | |
| [$^{125}$I]PYY | | | |
| PYY (human) | Gerald et al., 1995 *J Biol Chem*, 270 | | |
| [Leu$^{31}$,Pro$^{34}$]-PYY (human) | | | |
| [Pro$^{34}$]-PYY (human) | | | |
| PYY (porcine) | | | |
| PYY$_{13-36}$ (porcine) | | | |

Figure 9 (continued)

| Neuropeptide Y4 receptors | | Antagonists | References |
|---|---|---|---|
| Agonists | References | | |
| GR231118 | Tough et al., 2006, *J Pharmacol Exp Ther*, 319 | 1229U91 | Gehlertet al., 1997 *Peptides*, 18 |
| NPY, [Leu³¹,Pro³⁴]-NPY | Gregor et al., 1996, *FEBS Lett*, 381 | | |
| [Ala³¹,Aib³²]-NPY | Cabrele et al., 2002 *Biochemistry*, 41 | | |
| NPY₁₃₋₃₆ | Lundell et al., 1995 *J Biol Chem*, 270 | | |
| NPY₂₋₃₆ | | | |
| PP | Walker et al., 1997 *Peptides*, 18 | | |
| [Ile³¹,Gln³⁴]-PP | | | |
| PP₂₀₋₃₆ | Gregor et al., 1996, *FEBS Lett*, 381 | | |
| PYY | Dumont and Quirion 2000 *Br J Pharmacol*, 129 | | |
| [Leu³¹,Pro³⁴]-PYY | Gehlert et al., 1997 *Peptides*, 18 | | |
| [Leu³¹,Pro³⁴]-PYY | Tough et al., 2006 *J Pharmacol Exp Ther*, 319 | | |
| [Pro³⁴]-PYY | Lundell et al., 1995 *J Biol Chem*, 270, | | |
| [¹²⁵I]PYY | Walker et al., 1997 *Peptides*, 18 | | |
| PYY₃₋₃₆ (human) | | | |

Figure 9 (continued)

Neuropeptide Y5 receptors

| Agonists | References | Antagonists | References |
|---|---|---|---|
| [125I][PP$_{1-17}$,Ala$^{31}$,Aib$^{32}$]-NPY | | CGP 71683A | Dumont et al., 2003<br>Br J Pharmacol, 139 |
| GR231118 | Dumont et al., 2003<br>Br J Pharmacol, 139 | | |
| [Ala$^{31}$,Aib$^{32}$]-NPY | | FMS586 | Kakui et al., 2006<br>J Pharmacol Exp Ther, 317 |
| [D-Trp$^{32}$]-NPY | Hu et al., 1996<br>J Biol Chem, 271 | | |
| [PP$_{1-17}$,Ala$^{31}$,Aib$^{32}$]-NPY | | JCF 109 | Dumont et al., 2003<br>Br J Pharmacol, 139 |
| NPY | Cabrele et al., 2002<br>Biochemistry, 41 | | |
| [Ala$^{31}$,Aib$^{32}$]-NPY | | L-152,804 | |
| [Leu$^{31}$,Pro$^{34}$]-NPY | Hu et al., 1996<br>J Biol Chem, 271 | | |
| NPY$_{2-36}$ | | | |
| PP | | L-152,804 | Kanatani et al., 2000<br>Biochem Biophys Res Commun, 272 |
| PYY | | | |
| PYY$_{3-36}$ | | | |

Figure 9 (continued)

Neuropeptide FF/neuropeptide AF receptors

NPFF1

| Agonists | References | Antagonists | References |
|---|---|---|---|
| 1DMe | | | |
| [$^{125}$I]1DMe | | BIBP3226 | Mollereau et al., 2002 *Eur J Pharmacol*, 451 |
| EFWSLAAPQRF-NH$_2$ | Bonini et al., 2000 *J Biol Chem*, 275 | | |
| NPFF | Gouardères et al., 2002 *Neuroscience*, 115, | | |
| PP (frog) | Mollereau et al., 2002 *Eur J Pharmacol*, 451 | | |
| RFRP-3 (human) | | RF9 | Simonin et al., 2006, *Proc Natl Acad Sci U S A*, 103 |
| Y-RFRP-3 | | | |
| [$^{125}$I]Y-RFRP-3 | | | |

Figure 9 (continued)

Neuropeptide FF/neuropeptide AF receptors

NPFF2

| Agonists | References | Antagonists | References |
|---|---|---|---|
| 1DMe | Gouardères et al., 2002 *Neuroscience*, 115, | | |
| dNPA | Quelven et al., 2005 *Eur J Pharmacol*, 508 | BIBP3226 | Mollereau et al., 2002 *ur J Pharmacol*, 451 |
| EFWSLAAPQRF-NH$_2$ | Mollereau et al., 2002 *Eur J Pharmacol*, 451 | | |
| NPFF | Mollereau et al., 2001 *Br J Pharmacol*, 133 | | |
| PP (frog) | | RF9 | Simoninet al., 2006, *Proc Natl Acad Sci U S A*, 103 |
| RFRP-3 (human) | Mollereau et al., 2002 *Eur J Pharmacol*, 451 | | |
| YVPNLPQRF-NH$_2$ | | | |

Figure 9 (continued)

Nicotinic acid receptor family

GPR81

| Agonists | references |
|---|---|
| Nicotinic acid | Wise et al., 2003 J Biol Chem, 278 |

GPR109A

| Agonists | References |
|---|---|
| (+)-5-(5-bromothiophen-3-yl)-5-methyl-4-oxo-4,5-dihydro-furan-2-carboxylic acid | Taggart et al., 2005 J Biol Chem, 280 |
| D-β-hydroxybutyrate | |
| acifran | |
| acipimox | Wise et al., 2003 J Biol Chem, 278 |
| 5-butyl-1H-pyrazole-3-carboxylic acid | van Herk et al., 2003 J Med Chem, 46 |
| 5-methyl nicotinic acid | |
| nicotinic acid | Wise et al., 2003 J Biol Chem, 278 |
| [$^3$H]nicotinic acid | |
| 3-pyridine-acetic acid | |

GPR109B

| Agonists | References |
|---|---|
| acifran | |
| 5-ethyl-4-oxo-5-phenyl-4,5-dihydro-furan-2-carboxylic acid | Jung et al., 2007 J Med Chem, 50 |
| 1-isopropylbenzotriazole-5-carboxylic acid | Semple et al., 200 6 J Med Chem, 49 |
| 5-methyl-5-(5-methyl-triophen-3-yl)-4-oxo-4,5-dihydro-furan-2-carboxylic acid | Jung et al., 2007 J Med Chem, 50 |
| nicotinic acid | Wise et al., 2003 J Biol Chem, 278 |

NB: Currently no antagonists are known for GPR81, GPR109A or GPR109B

Figure 9 (continued)

| Opioid δ Receptor | | | |
|---|---|---|---|
| Agonists | References | Antagonists | References |
| β endorphin, | | (-)-naloxone | |
| (-)-bremazocine | | | |
| (-)-cyclazocine | | (-)-quadazocine | |
| (-)-EKC | | | |
| (-)-pentazocine | | BNTX | Toll et al., 1998 |
| DADLE | | | NIDA Res Monogr, 178 |
| deltorphin II | | | |
| dihydromorphine | Raynor et al., 1994 | CTAP | Yasuda et al., 1993 |
| diprenorphine | Mol Pharmacol, 45 | | Proc. Natl. Acad. Sci.., 90 |
| [³H]diprenorphine | | | |
| DPDPE | Toll et al., 1998 | β-FNA | Neilan et al., 1999 |
| DSLET | NIDA Res Monogr, 178 | | Br J Pharmacol, 128, |
| dynorphin 1-11 | | | |
| dynorphin 1-13 | Yasuda et al., 1993 | ICI 174,864 | |
| dynorphin 1-17 | Proc. Natl. Acad. Sci.., 90 | | Raynor et al., 1994 |
| dynorphin 1-8 | | naloxone | Mol Pharmacol, 45 |
| dynorphin B | Gong et al., 1998 | | |
| EKC | FEBS Lett, 439 | naltrexone | |
| endomorphin-1 | | | |
| [Leu]-enkephalin | Quock et al., 1997 | naltriben | |
| [Met]-enkephalin | Eur J Pharmacol, 326 | | |
| etonitazene | | naltrindole | |
| etorphine | | | |
| fentanyl | | nor-binaltorphimine | |
| morphine | | | |
| nalmefene | | TIPPψ | |
| nalorphine | | | |
| α-neoendorphin | | | |
| normorphine | | | |
| SNC80 | | | |

Figure 9 (continued)

Opioid K receptor

| Agonists | References | Antagonists | References |
|---|---|---|---|
| β endorphin (human) | | (−)-naloxone | Toll et al., 1998 |
| (±)-EKC | | (−)-quadazocine | NIDA Res Monogr, 178 |
| (−)-bremazocine | | | |
| (−)-cyclazocine | | BNTX | Yasuda et al., 1993 |
| (−)-EKC | Toll et al., 1998 | buprenorphine | Proc. Natl. Acad. Sci., 90 |
| (−)-methadone | NIDA Res Monogr, 178 | diprenorphine | |
| (−)-pentazocine | Zhu et al., 1997 J | [³H]diprenorphine | Simonin et al., 1995 |
| bremazocine | Pharmacol Exp Ther, 282 | | Proc Natl Acad Sci 92 |
| CI 977 | | β-FNA | |
| DAMGO | Yasuda et al., 1993 | GNTI | Jones and Portoghese 2000 |
| dihydromorphine | Proc. Natl. Acad. Sci., 90 | nalmefene | Eur J Pharmacol, 396 |
| dynorphin 1-11 | Hjorth et al., 1996 | (+)-naloxone | |
| dynorphin 1-13 | Mol Pharmacol, 50 | naltrexone | Chen et al., 1993 |
| dynorphin 1-13 | Meng et al., 1993 | naltriben | Biochem J, 295 |
| [D-Ala², F₅, Phe⁴]-dynorphin 1-13-NH₂ | Proc Natl Acad Sci 90 | | |
| dynorphin 1-17 | | naltrindole | |
| [Met⁵]-dynorphin 1-17 | Neumeyer et al., 2003 | nor-binaltorphimine | |
| dynorphin 1-17-NH₂ | J Med Chem, 46 | | |
| [D-Ala², F₅, Phe⁴]-dynorphin 1-17-NH₂ | | | |
| dynorphin 1-8 | | | |
| dynorphin B | | | |
| E2078 | | | |
| EKC | | | |
| enadoline | | | |
| [Leu]-enkephalin | | | |
| [Met]-enkephalin | | | |
| etonitazene | | | |
| etorphine | | | |
| fentanyl | | | |
| GR 89696 | | | |

Figure 9 (continued)

| Opioid K receptor | |
|---|---|
| Agonists | References |
| ICI 204448 | |
| morphine | Toll et al., 1998<br>NIDA Res Monogr, 178 |
| nalorphine | |
| naloxone benzoylhydrazone | Zhu et al., 1997 J Pharmacol Exp Ther, 282 |
| α-neoendorphin | |
| β-neoendorphin | Yasuda et al., 1993<br>Proc. Natl. Acad. Sci.., 90 |
| normorphine | Hjorth et al., 1996<br>Mol Pharmacol, 50 |
| pentazocine | Meng et al., 1993<br>Proc Natl Acad Sci 90 |
| salvinorin A | |
| tifluadom | Neumeyer et al., 2003<br>J Med Chem, 46 |
| TRK820 | |
| U50488<br>U63640<br>U69593 | |
| [$^3$H]U69593 | |

Figure 9 (continued)

| Opioid μ receptor | | | |
|---|---|---|---|
| Agonists | References | Antagonists | References |
| β endorphin | | (-)-bremazocine | |
| (-)-cyclazocine | | (-)-naloxone | |
| (-)-EKC | | (-)-naloxone | |
| (-)-methadone | | (-)-quadazocine | |
| (-)-pentazocine | | BNTX | |
| buprenorphine | | CTAP | |
| codeine | | CTOP | |
| DADLE | | diprenorphine | |
| DAMGO | Raynor et al., 1994 Mol Pharmacol, 45 | diprenorphine | Raynor et al., 1994 Mol Pharmacol, 45 |
| [tyrosyl 3,5-³H]DAMGO | | [15,16-³H]diprenorphine | |
| dihydromorphine | | β-FNA | |
| DSLET | Toll et al., 1998 NIDA Res Monogr, 178 | β-FNA | Toll et al., 1998 NIDA Res Monogr, 178 |
| dynorphin 1-11 | | nalmefene | |
| dynorphin 1-13 | | nalorphine | |
| dynorphin 1-17 | | naloxonazine | |
| dynorphin 1-8 | Gong et al., 1998 FEBS Lett, 439 | [N-allyl-2,3-³H]naloxone | |
| dynorphin B | | naloxone benzoylhydrazone | |
| endomorphin-1 | | naloxone | |
| [Leu]-enkephalin | | naloxone benzoylhydrazone | |
| [Met]-enkephalin | | naltrexone | |
| etonitazene | | naltriben | |
| etorphine | | naltrindole | |
| fentanyl | | nor-binaltorphimine | |
| morphine | | | |
| normorphine | | | |
| PL017 | | | |

Figure 9 (continued)

| Opioid NOP receptor | | | |
|---|---|---|---|
| Agonists | References | Antagonists | References |
| [³H]14-Tyr-N/OFQ | Adapa and Toll 1997 Neuropeptides, 31 | J-113397 | Ozaki et al., 2000 Eur J Pharmacol, 402 |
| AC-RYYRIK-NH$_2$</SUB<td> | | | |
| AC-RYYRIK-NH$_2$ | McDonald et al., 2003 Br J Pharmacol, 140, | JTC-801 | Shinkai et al., 2000 J Med Chem, 43 |
| AC-RYYRWK-NH$_2$ | Dooley et al., 1997 J Pharmacol Exp Ther, 283 | | |
| AC-RYYRWK-NH$_2$ | McDonald et al., 2003 Br J Pharmacol, 140 | [Nphe¹]N/OFQ(1-13)NH$_2$ | Calo et al., 2002 Br J Pharmacol, 136 |
| N/OFQ | | | |
| N/OFQ | | | |
| [³H]N/OFQ | Okada et al., 2000 Biochem Biophys Res Commun, 278 | peptide III-BTD | Becker et al., 1999 J Biol Chem, 274 |
| [Arg¹⁴Lys¹⁵]N/OFQ | | | |
| N/OFQ(1-13)NH$_2$ | Enck et al., 2000 Proc Natl Acad Sci 97 | | |
| [(pF)Phe⁴]N/OFQ(1-13)NH$_2$ | | SB 612111 | Zaratin et al., 2004 J Pharmacol Exp Ther, 308 |
| [F/G]N/OFQ(1-13)NH$_2$ | | | |
| N/OFQ-NH$_2$ | | | |
| Ro64-6198 | Carrà et al., 2005 J Pharmacol Exp Ther, 312 | UFP-101 | Calo et al., 2002 Br J Pharmacol, 136 |
| UFP-102 | | | |

Figure 9 (continued)

| Orexin OX1 receptor | | | |
|---|---|---|---|
| Agonists | references | Antagonists | References |
| Orexin-A | Langmead et al., 2004 Br J Pharmacol, 141 | 1-(2,4-dibromo-phenyl)-3-((4S,5S)-2,2-dimethyl-4-phenyl-[1,3]dioxan-5-yl)-urea | McAtee et al., 2004 Bioorg Med Chem Lett, 14 |
| Orexin-A 2-33 | Lang et al., 2004 J Med Chem, 47 | 1-(2-bromo-phenyl)-3-((4S,5S)-2,2-dimethyl-4-phenyl-[1,3]dioxan-5-yl)-urea | Porter et al., 2001 Bioorg Med Chem Lett, 11 |
| Orexin-B | Langmead et al., 2004 Br J Pharmacol, 141 | SB-334867 | |
| | | SB-408124 | |
| [Ala11, D-Leu11]Orexin-B | Asahi et al., 2003 Bioorg Med Chem Lett, 13 | SB-410220 | Langmead et al., 2004 Br J Pharmacol, 141 |
| | | [3H]SB-674042 | |

Figure 9 (continued)

| P2Y12 receptor | | | |
|---|---|---|---|
| Agonists | References | Antagonists | References |
| 2MeSADP | Herbert and Savi 2003 *Semin Vasc Med*, 3 | 2MeSAMP | Takasaki et al., 2001 *Mol Pharmacol*, 60 |
| [³H]2MeSADP | Takasaki et al., 2001 *Mol Pharmacol*, 60 | active metabolite of clopidogrel | Herbert and Savi 2003 *Semin Vasc Med*, 3 |
| 2MeSATP | Herbert and Savi 2003 *Semin Vasc Med*, 3 | AR-C69931MX | Takasaki et al., 2001 *Mol Pharmacol*, 60 |
| ADP | Takasaki et al., 2001 *Mol Pharmacol*, 60 | | |
| ADPβS | | | |
| ATP | Herbert and Savi 2003 *Semin Vasc Med*, 3 | pCMPS | Herbert and Savi 2003 *Semin Vasc Med*, 3 |
| ATPγS | | | |

Figure 9 (continued)

P2Y13 receptor

| Agonists | References | Antagonists | References |
|---|---|---|---|
| 2MeSADP | | 2MeSAMP | |
| [33P]2MeSADP | | $Ap_4A$ | |
| 2MeSATP | Marteau et al., 2003 | AR-C67085MX | Marteau et al., 2003 |
| ADP | *Mol Pharmacol*, 64, | AR-C69931MX | *Mol Pharmacol*, 64, |
| ADPβS | | PPADS | |
| ATP | | reactive blue 2 | |
| ATPγS | | suramin | |

P2Y14 receptor

| Agonists | References |
|---|---|
| UDP-glucose | Freeman et al., 2001 |
| UDP-glucuronic acid | *Genomics*, 78 |
| UDP-N-acetylglucosamine | |

NB: No antagonists are known for P2Y14

Figure 9 (continued)

Prostanoid DP2 receptors

| Agonists | References | Antagonists | References |
|---|---|---|---|
| $\Delta^{12}$-PGJ$_2$ | | | |
| 13,14-dihydro-15-keto-PGD$_2$ | | | |
| 13,14-dihydro-15-keto-PGF$_{2\alpha}$ | | | |
| 15(R)-15-methyl-PGD$_2$ | Sawyer et al., 2002 Br J Pharmacol, 137 | | |
| 15(S)-15-methyl-PGD$_2$ | Hata et al., 2003 J Pharmacol Exp Ther, 306 | | |
| 15-deoxy-$\Delta^{12,14}$-PGD$_2$ | | | |
| 15-deoxy-$\Delta^{12,14}$-PGJ$_2$ | | | |
| CAY 10471 | Ulven and Kostenis 2005 J Med Chem, 48 | | |
| indomethacin | | ramatroban | Hata et al., 2005 J Biol Chem, 280 |
| L-883,595 | Gervais et al., 2005 Mol Pharmacol, 67 | | |
| L-888,291 | | | |
| L-888,607 | Shichijo et al., 2003 J Pharmacol Exp Ther, 307 | | |
| PGD$_2$ | | | |
| [$^3$H]PGD$_2$ | | [$^3$H]ramatroban | Sugimoto et al., 2005 Eur J Pharmacol, 524 |
| PGD$_3$ | | | |
| PGE$_2$ | | | |
| PGF$_{2\alpha}$ | | | |
| PGJ$_2$ | | | |
| U46619 | | | |

Figure 9 (continued)

Serotonin 5-HT1A receptor

| Agonists | References | Antagonists | References |
|---|---|---|---|
| (-)-quinpirole | | (-)-propranolol | |
| apomorphine | | (-)-tertatolol | |
| aripiprazole | | (R)-flurocarazolol | Newman-Tancredi et al., 1997 Naunyn Schmiedebergs Arch Pharmacol, 355 |
| BMY-14802 | Newman-Tancredi et al.,1999 Naunyn Schmiedebergs Arch Pharmacol, 359 | (S)-flurocarazolol | |
| BMY-7378 | | [³H]-p-MPPF | |
| BRL-15572 | Millan et al., 2002 J Pharmacol Exp Ther, 303 | p-MPPI | |
| bromocriptine | | (+)-butaclamol | Newman-Tancredi et al., 1998 Eur J Pharmacol, 355 |
| buspirone | Shapiro et al., 2003 Neuropsychopharmacology, 28 | chlorpromazine | |
| cabergoline | | cyamemazine | |
| clozapine | | fluspirilene | Roth et al., 2001 Psychopharmacology (Berl), 157 |
| CP 93129 | Newman-Tancredi et al., 1998 Eur J Pharmacol, 355 | GR 125,743 | Kalipatnapu et al., 2004 Biosci Rep, 24 |
| 5-CT | | GR 218,231 | |
| donitriptan | Khawaja et al., 1997 Life Sci, 60 | haloperidol | |
| eletriptan | | iloperidone | Hameg et al., 2003 Biochem Pharmacol, 65, |
| EMDT | Price et al., 1997 Naunyn Schmiedebergs Arch. Pharmacol., 356 | iloperidone | |
| FG-5893 | | ketanserin | Schotte et al., 1996 Psychopharmacology (Berl), 124 |
| (+)-flesinoxan | Newman-Tancredi et al., 1992 Biochem J, 285 | methiothepin | |
| fluparoxan | | MPDT | Millan et al., 2000 J Pharmacol Exp Ther, 293 |
| GR-127935 | | NAD 299 | |
| 5-HT | | [³H]NAD 299 | |

Figure 9 (continued)

Serotonin 5-HT1A receptor

| Agonists | References | Antagonists | References |
|---|---|---|---|
| ipsapirone | | NAN 190 | |
| L-694,247 | | 9-OH-risperidone | |
| L-772,405 | | pimozide | |
| lisuride | Millan et al., 2002 *J Pharmacol Exp Ther*, 303 | pindolol | Newman-Tancredi et al., 1997 *Naunyn Schmiedebergs Arch Pharmacol*, 355 |
| LSD | Newman-Tancredi et al., 1998 *Eur J Pharmacol*, 355 | pipamperone | |
| LY293284 | | pizotifen | |
| LY334370 | | raclopride | Kalkman et al., 2001 *Neuropsychopharmacology*, 25 |
| LY344864 | | Rec 15/3079 | |
| 7-methoxy-1-naphthylpiperazine | Newman-Tancredi et al., 1992 *Biochem J*, 285 | repinotan | |
| nafadotride | John et al., 1999 *J Pharmacol Exp Ther*, 290 | risperidone | Kongsamut et al., 1996 *Eur J Pharmacol*, 317 |
| 1-naphthylpiperazine | | risperidone | |
| naratriptan | Napier et al., 1999 *Eur J Pharmacol*, 368 | ritanserin | |
| ocaperidone | | SB 272183 | Newman-Tancredi et al., 1992 *Biochem J*, 285 |
| 8-OH-DPAT | Millan et al., 2000 *Synapse*, 35 | SB 649915 | |
| [³H]8-OH-DPAT | | SB 714786 | Newman-Tancredi et al., 1998 *Eur J Pharmacol*, 355 |
| olanzapine | | SDZ-216525 | |
| ORG-5222 | | sertindole | |
| PAPP | | spiperone | |
| pergolide | | thioridazine | |

Figure 9 (continued)

Serotonin 5-HT1A receptor

| Agonists | References | Antagonists | References |
|---|---|---|---|
| piribedil | | tiospirone | |
| quetiapine | | | |
| rizatriptan | Millan et al., 2002 *J Pharmacol Exp Ther*, 303 | | |
| roxindole | | (+)-UH 301 | Newman-Tancredi et al., 1998 *Eur J Pharmacol*, 355 |
| RU 24969 | Newman-Tancredi et al., 1998 *Eur J Pharmacol*, 355 | | |
| S-14506 | | | |
| S-14671 | | WAY-100135 | Millan et al., 2000 *Synapse*, 35 |
| S-15535 | Newman-Tancredi et al., 1992 *Biochem J*, 285 | | |
| [³H]S-15535 | | WAY-100635 | Newman-Tancredi et al., 1998 *Naunyn Schmiedebergs Arch Pharmacol*, 357 |
| S-16924 | | | |
| SB 216641 | Russell et al., 1999 *J Med Chem*, 42 | | |
| SL65.0155 | | yohimbine | Schotte et al., 1996 *Psychopharmacology (Berl)*, 124 |
| spiroxatrine | Newman-Tancredi et al., 1997 *Naunyn Schmiedebergs Arch Pharmacol*, 355 | | |
| sumatriptan | | | |
| tandospirone | | | |
| terguride | Nichols et al., 2002 *J Med Chem*, 45 | zotepine | |
| U92012A | | | |
| xanomeline | Blair et al., 2000 *J Med Chem*, 43 | | |
| zalospirone | | | |
| ziprasidone | | | |
| zolmitriptan | | | |

Figure 9 (continued)
Serotonin 5-HT1B receptor

| Agonists | References | Antagonists | References |
|---|---|---|---|
| 5-(nonyloxy)-tryptamine | | (-)-pindolol | |
| alniditan | Granas and Larhammar 1999 *Eur J Pharmacol*, 380 | (R)-flurocarazolol | |
| [³H]alniditan | | (S)-flurocarazolol | |
| aripiprazole | | cyanopindolol | |
| BMS 181,101 | Leysen et al., 1996 *Mol Pharmacol*, 50 | [³H]GR-125743 | Roth et al., 2001 *Psychopharmacology (Berl)*, 157 |
| BRL-15572 | | GR-127935 | |
| bromocriptine | | ketanserin | |
| cabergoline | Lesage et al., 1998 *Br J Pharmacol*, 123 | ketanserin | Maroteaux et al., 1992 *Proc Natl Acad Sci U S A*, 89 |
| CGS-12066 | | metergoline | |
| clozapine | Shapiro et al., 2003 *Neuropsychopharmacology*, 28 | methiothepin | Granas and Larhammar 1999 *Eur J Pharmacol*, 380 |
| CP-122288 | | methysergide | |
| 5-CT | | mianserin | Lesage et al., 1998 *Br J Pharmacol*, 123 |
| dihydroergotamine | Newman-Tancredi et al., 2000 *Mol Pharmacol*, 58 | ocaperidone | |
| dipropyl-5-CT | | 5-OH-DPAT | Parker et al., 1996 *J Neurochem*, 67 |
| donitriptan | Price et al., 1997 *Naunyn Schmiedebergs Arch. Pharmacol.*, 356 | 9-OH-risperidone | |
| eletriptan | | pipamperone | |
| [³H]eletriptan | | rauwolscine | Schotte et al., 1996 *Psychopharmacology (Berl)*, 124 |
| F 11356 | | risperidone | |
| GR-55562 | | ritanserin | |
| GR 127935 | | | |
| 5-HT | | S33084 | |

Figure 9 (continued)

Serotonin 5-HT1B receptor

| Agonists | References | Antagonists | References |
|---|---|---|---|
| [³H]-5-HT | | SB 224289 | |
| L-694,247 | Davidson et al., 1997 Br J Pharmacol, 121 | SB 272183 | Roth et al., 2001 Psychopharmacology (Berl), 157 |
| L-772,405 | | | |
| L-775,606 | Selkirk et al., 1998 Br J Pharmacol, 125 | SB 649915 | Maroteaux et al., 1992 Proc Natl Acad Sci U S A, 89 |
| lisuride | | | |
| LY344864 | | SB 714786 | Granas and Larhammar 1999 Eur J Pharmacol, 380 |
| lysergol | Newman-Tancredi et al., 1999 Naunyn Schmiedebergs Arch Pharmacol, 359 | sertindole | |
| 2-Me-5-HT | | | |
| 5-MeOT | | spiperone | Lesage et al., 1998 Br J Pharmacol, 123 |
| 7-methoxy-1-naphthylpiperazine | Leysen et al., 1996 Mol Pharmacol, 50 | (+)-WAY 100135 | Parker et al., 1996 J Neurochem, 67 |
| 1-naphthylpiperazine | | | |
| naratriptan | Granas and Larhammar 1999 Eur J Pharmacol, 380 | yohimbine | |
| 8-OH-DPAT | | yohimbine | Schotte et al., 1996 Psychopharmacology (Berl), 124 |
| [³H]8-OH-DPAT | | | |
| olanzapine | | zotepine | |
| ORG-5222 | | | |
| oxymetazoline | | | |
| pergolide | | | |
| rizatriptan | | | |
| roxindole | | | |

Figure 9 (continued)

| Serotonin 5-HT1B receptor | |
|---|---|
| Agonists | References |
| RU 24969 | |
| SB 216641 | |
| SL65.0155 | |
| sumatriptan | Shapiro et al., 2003 *Neuropsychopharmacology*, 28 |
| [$^3$H]sumatriptan | Newman-Tancredi et al., 2000 *Mol Pharmacol*, 58 |
| terguride | Price et al., 1997 *Naunyn Schmiedebergs Arch. Pharmacol.*, 356 |
| TFMPP | |
| tryptamine | Leysen et al., 1996 *Mol Pharmacol*, 50 |
| xanomeline | |
| ziprasidone | |
| zolmitriptan | |

Figure 9 (continued)

Serotonin 5-HT1D receptor

| Agonists | References | Antagonists | References |
|---|---|---|---|
| alniditan | Lesage et al., 1998 *Br J Pharmacol*, 123 | m-CPP | Millan et al., 2002 *J Pharmacol Exp Ther*, 303, |
| [³H]alniditan | | bufotenine | |
| aripiprazole | Shapiro et al., 2003 *Neuropsychopharmacolog y*, 28 | cyanopindolol | |
| BRL-15572 | | fluspirilene | Weinshank et al., 1992 *Proc. Natl. Acad. Sci. U.S.A.*, 89 |
| bromocriptine | | GR-127935 | |
| cabergoline | | haloperidol | |
| CGS-12066 | Price, et al., 1997 *Naunyn Schmiedebergs Arch. Pharmacol*, 356 | ketanserin | Schotte et al., 1996 *Psychopharmacology (Berl)*, 124 |
| clozapine | | L-772,405 | |
| CP-122288 | | metergoline | |
| 5-CT | Millan et al., 2002 *J Pharmacol Exp Ther*, 303, | methiothepin | Hamblin and Metcalf 1991 *Mol Pharmacol*, 40 |
| dihydroergotamine | | methysergide | |
| dimethyltryptamine | | MPDT | |
| dipropyl-5-CT | Weinshank et al., 1992 *Proc. Natl. Acad. Sci. U.S.A.*, 89 | ocaperidone | Leysen et al., 1996 *Mol Pharmacol*, 50, |
| donitriptan | | 9-OH-risperidone | |
| eletriptan | | pipamperone | |
| [³H]eletriptan | Schotte et al., 1996 *Psychopharmacology (Berl)*, 124 | rauwolscine | Millan et al., 2000 *J Pharmacol Exp Ther*, 293 |
| EMDT | | risperidone | |
| F 11356 | Domenech et al., 1997 *Naunyn Schmiedebergs Arch Pharmacol*, 356 | | |
| GR 127935 | | ritanserin | |
| 5-HT | | | |

Figure 9 (continued)

Serotonin 5-HT1D receptor

| Agonists | References | Antagonists | References |
|---|---|---|---|
| [³H]5-HT | Shapiro et al., 2003 Neuropsychopharmacology, 28 | S33084 | Millan et al., 2002 J Pharmacol Exp Ther, 303, |
| lisuride | | | |
| LY344864 | | SB 224289 | |
| (+)-lysergic acid | Price, et al., 1997 Nauryn Schmiedebergs Arch. Pharmacol., 356 | SB 272183 | Weinshank et al., 1992 Proc. Natl. Acad. Sci. U.S.A., 89 |
| lysergol | | | |
| α-Me-5-HT | Millan et al., 2002 J Pharmacol Exp Ther, 303, | SB 277011-A | |
| 2-Me-5-HT | | SB 649915 | Schotte et al., 1996 Psychopharmacology (Berl), 124 |
| 5-MeOT | Weinshank et al., 1992 Proc. Natl. Acad. Sci. U.S.A., 89 | | |
| 7-methoxy-1-naphthylpiperazine | | SB 714786 | |
| 1-naphthylpiperazine | Napier, et al., 1999 Eur J Pharmacol, 368, | sertindole | |
| naratriptan | | spiperone | Hamblin and Metcalf 1991 Mol Pharmacol, 40 |
| 8-OH-DPAT | | (+)-WAY 100135 | |
| [³H]8-OH-DPAT | Glennon et al., 2000 J Med Chem, 43 | | |
| olanzapine | | | |
| ORG-5222 | Leysen et al., 1996 Mol Pharmacol, 50, | yohimbine | Leysen et al., 1996 Mol Pharmacol, 50, |
| oxymetazoline | | | |
| pergolide | | zotepine | Millan et al., 2000 J Pharmacol Exp Ther, 293 |
| quetiapine | | | |
| rizatriptan | | | |
| roxindole | | | |

Figure 9 (continued)

| Serotonin 5-HT1D receptor | |
|---|---|
| Agonists | References |
| RU 24969 | Price, et al., 1997 *Naunyn Schmiedebergs Arch. Pharmacol.*, 356 |
| SB 216641 | |
| SL65.0155 | Millan et al., 2002 *J Pharmacol Exp Ther*, 303, |
| sumatriptan | Weinshank et al., 1992 *Proc. Natl. Acad. Sci. U.S.A.*, 89 |
| [$^3$H]sumatriptan | Napier, et al., 1999 *Eur J Pharmacol*, 368 |
| terguride | Phebus et al., 1997 *Life Sci*, 61 |
| TFMPP | Schotte et al., 1996 *Psychopharmacology (Berl)*, 124 |
| tryptamine | |
| xanomeline | |
| ziprasidone | |
| zolmitriptan | |

Figure 9 (continued)

Serotonin 5-ht1e receptor

| Agonists | references | Antagonists | References |
|---|---|---|---|
| m-CPP | Bai et al., 2004 Eur J Pharmacol, 484 | fluspirilene | |
| BRL-15572 | | metergoline | |
| clozapine | Schotte et al., 1996 Psychopharmacology (Berl), 124 | methiothepin | Schotte et al., 1996 Psychopharmacology (Berl), 124 |
| 5-CT | Adham et al., 1993 Proc Natl Acad Sci U S A, 90, | methylergonovine | |
| dihydroergotamine | | | |
| DOI | | methysergide | McAllister et al., 1992 Proc Natl Acad Sci U S A, 89, |
| donitriptan | Parker et al., 1996 J Neurochem, 67 | 1-naphthylpiperazine | |
| eletriptan | | 9-OH-risperidone | Adham et al., 1993 Proc Natl Acad Sci 90 |
| EMDT | John et al., 1999 J Pharmacol Exp Ther, 290, | rauwolscine | |
| ergonovine | | risperidone | Parker et al., 1996 J Neurochem, 67 |
| ergotamine | Bai et al., 2004 Eur J Pharmacol, 484 | sertindole | |
| 5-fluorotryptamine | | yohimbine | |
| GR-127935 | Schotte et al., 1996 Psychopharmacology (Berl), 124 | zotepine | |
| 5-HT | | | |
| [³H]5-HT | | | |
| LY344864 | | | |
| lysergol | | | |

Figure 9 (continued)

| Serotonin 5-ht1e receptor | |
|---|---|
| α-Me-5-HT | |
| 2-Me-5-HT | |
| 5-MeO-DMT | Bai et al., 2004 *Eur J Pharmacol*, 484 |
| 5-MeOT | |
| naratriptan | Schotte et al., 1996 *Psychopharmacology (Berl)*, 124 |
| 8-OH-DPAT | Adham et al., 1993 *Proc Natl Acad Sci U S A*, 90, |
| olanzapine | |
| ORG-5222 | Parker et al., 1996 *J Neurochem*, 67 |
| quetiapine | |
| rizatriptan | John et al., 1999 *J Pharmacol Exp Ther*, 290, |
| sumatriptan | Bai et al., 2004 *Eur J Pharmacol*, 484, |
| TFMPP | |
| tryptamine | Schotte et al., 1996 *Psychopharmacology (Berl)*, 124 |
| xanomeline | |
| ziprasidone | |
| zolmitriptan | |

Figure 9 (continued)

| Serotonin 5-HT1F receptor | | | |
|---|---|---|---|
| Agonists | references | Antagonists | references |
| BRL-15572 | Dhawan, et al., 1996 Pharmacol. Rev., 48 | | |
| clozapine | | metergoline | |
| 5-CT | | metergoline | |
| 5-CT | Horan et al., 1993 J Pharmacol Exp Ther, 266 | | |
| dihydroergotamine | | methiothepin | Wang et al., 1994 FEBS Lett., 348 |
| dipropyl-5-CT | Zajac et al., 1983 Biochem. Biophys. Res. Commun., 111 | methylergonovine | |
| DOI | | methysergide | Mollereau et al., 1994 FEBS Lett, 341 |
| donitriptan | | methysergide | Zajac et al., 1983 Biochem. Biophys. Res. Commun., 111, |
| eletriptan | Wang et al., 1994 FEBS Lett., 348, | | |
| ergotamine | | 1-naphthylpiperazine | |
| ergotamine | Mollereau et al., 1994 FEBS Lett, 341, | | |
| GR-127935 | | risperidone | Horan et al., 1993 J Pharmacol Exp Ther, 266, |
| 5-HT | | | |
| 5-HT | Hu et al., 1998 J Neurosci, 18, | sertindole | |
| [³H]-5-HT | | | |
| LY334370 | | yohimbine | |
| [³H]LY334370 | Pan et al., 2002 J Neurophysiol, 88 | | |
| LY344864 | | yohimbine | |
| α-Me-5-HT | | | |

Figure 9 (continued)

| Serotonin 5-HT1F receptor | |
|---|---|
| Agonists | References |
| 2-Me-5-HT | |
| 5-MeO-DMT | Dhawan, et al., 1996 *Pharmacol. Rev.*, 48 |
| 5-MeOT | |
| NAN 190 | Horan et al., 1993 *J Pharmacol Exp Ther*, 266 |
| naratriptan | |
| 8-OH-DPAT | Zajac et al., 1983 *Biochem. Biophys. Res. Commun.*, 111 |
| olanzapine | Wang et al., 1994 *FEBS Lett.*, 348, |
| quetiapine | |
| rizatriptan | Mollereau et al., 1994 *FEBS Lett*, 341, |
| sumatriptan | |
| sumatriptan | Hu et al., 1998 *J Neurosci*, 18, |
| TFMPP | |
| tryptamine | Pan et al., 2002 *J Neurophysiol*, 88 |
| xanomeline | |
| zolmitriptan | |

Figure 9 (continued)

Serotonin 5-ht5a receptor

| Agonists | References | Antagonists | References |
|---|---|---|---|
| 5-CT | Matthes et al., 1993 *Mol. Pharmacol.*, 43 | (-)-propranolol | Rees et al., 1994 *FEBS Lett.*, 355, |
| [³H]5-CT | | bufotenine | |
| donitriptan | Grailhe et al., 2001 *Eur J Pharmacol*, 418, | clozapine | Matthes et al., 1993 *Mol. Pharmacol.*, 43 |
| EMDT | | ergotamine | Grailhe et al., 2001 *Eur J Pharmacol*, 418 |
| 5-HT | Erlander et al., 1993 *Proc Natl Acad Sci U S A*, 90, | ketanserin | |
| [¹²⁵I]LSD | | methiothepin | Erlander et al., 1993 *Proc Natl Acad Sci U S A*, 90, |
| lysergic acid | | methysergide | |
| 8-OH-DPAT | John et al., 1999 *J Pharmacol Exp Ther*, 290 | MPDT | Glennon et al., 2000 *J Med Chem*, 43 |
| RU 24969 | | ritanserin | |
| sumatriptan | Rees et al., 1994 *FEBS Lett.*, 355, | SB 699551 | Grailhe et al., 2001 *Eur J Pharmacol*, 418 |
| TFMPP | | yohimbine | |

Figure 15 (continued)

| | cAMP[1] in response to Gi stimulation | Gi mediated cellular response measured by CDS | Difference between Gi and Gs cellular response | Phosphorylation | Cell proliferation | Comments |
|---|---|---|---|---|---|---|
| FG1 | • cAMP increases relative to control (baseline cAMP concentration following forskolin stimulation) <br><br> OPN effect : •cAMP increases even more | • Highest reduction in dZiecs relative to control <br> • Lowest Gi-coupled receptor response <br> • 60-90% reduction in activity compared to control (i.e., 10-40% of maximal response of control) <br><br> OPN effect : •reduction in dZiecs is decreased (Gi-coupled response is increased) | • ΔG < -10 measured by CDS <br> • Ratio of cellular response Gi/Gs < about 0.5 <br><br> OPN effect : — | • All Gi (1-3) are phosphorylated (inactive) <br><br> OPN effect : • increase in Gi phosphorylation | • Greatest reduction in cell proliferation (about 50% or more) relative to control <br><br> OPN effect : • increase in cell proliferation | • Coupled to Gs; <br> • 60-90% reduction in Gi mediated activity compared to control <br><br> • OPN has a protective effect (decreases risk for developing IS) <br> • Fold effect: >100% of maximal response |
| FG2 | • No significant (or very weak) cAMP decrease relative to control (i.e. baseline cAMP concentration following forskolin stimulation) <br><br> OPN effect : • weak increase in cAMP production (i.e., weaker cAMP reduction) | • Intermediate reduction in dZiecs relative to control; <br> • Intermediate Gi-coupled receptor response <br> • 40-60% reduction in activity compared to control (i.e., 60-40% of maximal response of control) <br><br> OPN effect : <br> • Further reduction in dZiecs <br> • Gi-coupled receptor response is further decreased in the presence of OPN. | • ΔG between + 10 and -10 measured by CDS <br> • Ratio of cellular response Gi/Gs between about 0.5 and 1.5 <br><br> OPN effect : — | • Gi1 and Gi2 are Phosphorylated <br> • Gi3 is not Phosphorylated, remains functional. <br><br> OPN effect : • Further increase in Gi phosphorylation | • Intermediate reduction in cell proliferation (between about 25-45% reduction) relative to control <br><br> OPN effect : • Further reduction in cell proliferation | • FG2 subjects are more likely to progress to more severe form of scoliosis. <br><br> • 40-60% reduction in Gi mediated activity compared to control <br><br> • OPN exacerbates the defect in the strongest way. (increases risk for developing IS) <br> • Fold effect: <50% of maximal response |

[1] cAMP normally significantly decreases in response to Gi stimulation in control cells.

Figure 15 (continued)

| FG3 | • Weak cAMP decrease relative to control (i.e. baseline cAMP concentration following forskolin stimulation) | • Lowest reduction in dZIEcs or % of maximal response relative to control; • Highest Gi-coupled receptor response (but less than control) • 10-40% reduction in activity compared to control (i.e., 60-90% of maximal response of control) | • $\Delta G > +10$ measured by CDS • Ratio of cellular response Gi/Gs > about 1.5 | • $G_{i2}$ and $G_{i3}$ are phosphorylated. • $G_{i1}$ is not phosphorylated, remains functional. | • Lowest reduction in cell proliferation (about 25% or less) relative to control | • 10-40% reduction in Gi mediated activity compared to control |
|---|---|---|---|---|---|---|
| | OPN effect : • weak increase in cAMP production (i.e., less significant than for FG2) | OPN effect : • Further reduction in dZIEcs • Gi-coupled receptor response is further decreased in the presence of OPN. | OPN effect : --- | OPN effect : • Further increase in Gi phosphorylation | OPN effect : • Further reduction in cell proliferation | • OPN exacerbates the defect but to a lesser extent than in FG2 patients. (increases risk for developing IS) • Fold effect: between 50%-95% of maximal response |

Figure 16 (continued)

| Agonist | Receptor | Activity | Primary Transducer | Effector/Response | Secondary Transduction | Effector/Response |
|---|---|---|---|---|---|---|
| | | | | CLUSTER 1 | | |
| DAMGO | Mu opioid receptor | Full agonist | $G_i/G_o$ family | Adenylate cyclase stimulation | $G_q/G_{11}$ family | Phospholipase C stimulation |
| | | | | Adenylate cyclase inhibition | | Comments: $G_{16}$ couples to the μ opioid receptor and activates PLC. |
| | | | | Phospholipase C stimulation | | |
| | | | | Potassium channel | | |
| | | | | Calcium channel | | |
| | | | | Phospholipase $A_2$ stimulation | | |
| | | | | Phospholipase D stimulation | | |
| | | | | Comments: The following systems have also been reported to be activated following $G_i/G_o$ activation via the μ receptor: | | |
| | | | | epidermal growth factor receptor transactivation and subsequent mitogen activated protein kinase ERK [10,65], | | |
| | | | | Jun N-terminal kinase (JNK) expression and activity [33,54,112], | | |
| | | | | Increases cAMP, intracellular calcium, conductance change pathway unknown. Others include: Rho | | |
| LPA | LPA5 receptor | Full agonist | $G_q/G_{11}$ family | | | |
| | | | $G_{12}/G_{13}$ family | | | |
| | LPA4 receptor | Agonist | $G_s$ family | Adenylate cyclase stimulation | | |
| | | | $G_i/G_o$ family | | | |
| | | | $G_q/G_{11}$ family | | | |

Figure 16 (continued)

| | | | | | |
|---|---|---|---|---|---|
| | LPA3 receptor | Agonist | $G_{12}/G_{13}$ family | | |
| | | | $G_i/G_o$ family | Adenylate cyclase inhibition | |
| | | | $G_q/G_{11}$ family | Phospholipase $A_2$ stimulation | |
| | S1P1 receptor | Agonist | $G_i/G_o$ family | Adenylate cyclase inhibition | |
| | | | | Phospholipase C stimulation | |
| | | | | Calcium channel | |
| | | | | Phospholipase D stimulation | |
| | | | | involved in ERK phosphorylation [26] and stimulation of the PI3K/PKB and MEK/ERK pathways [7], and activation of Rac | |
| | LPA2 receptor | Agonist | $G_i/G_o$ family | Adenylate cyclase inhibition | $G_i/G_o$ family |
| | | | $G_q/G_{11}$ family | Phospholipase $A_2$ stimulation | $G_q/G_{11}$ family |
| | | | $G_{12}/G_{13}$ family | Phosphatidylinositol-3-Kinase, RAS, Rho, MAP kinase activation | $G_{12}/G_{13}$ family |
| | LPA6 receptor | Agonist | $G_s$ family | Adenylate cyclase stimulation | |
| | | | $G_i/G_o$ family | Phospholipase C stimulation | |
| | | | $G_{12}/G_{13}$ family | Increased intracellular calcium using a promiscuous Gs protein, ERK1/2 activation, and reduced forskolin-stimulated cAMP. G13-Rho pathway [17], and Gα12/13-Rho, PLC, PKC, ROCK, p38, PI3K pathway stimulation | |
| NECA | A3 receptor | Full agonist | $G_i/G_o$ family | Adenylate cyclase inhibition | $G_i/G_o$ family |
| | A2A receptor | Full agonist | $G_s$ family | Adenylate cyclase stimulation | $G_q/G_{11}$ family |
| | A1 receptor | Full agonist | $G_i/G_o$ family | Adenylate cyclase inhibition | $G_s$ family |
| | | | | Phospholipase C stimulation | |
| | | | | | $G_q/G_{11}$ family |

Figure 16 (continued)

| | | A2B receptor | Full agonist | $G_q/G_{11}$ family | Phospholipase C stimulation | | |
|---|---|---|---|---|---|---|---|
| Melatonin | MT1 | | Full agonist | $G_i/G_o$ family | Adenylate cyclase inhibition | $G_q/G_{11}$ family | |
| | MT2 | | Full agonist | $G_i/G_o$ family | Adenylate cyclase inhibition, phospholipase C stimulation | | |
| | | | | | CLUSTER 2 | | |
| CB65 | C2B | | Full agonist | $G_i/G_o$ family | Adenylate cyclase inhibition | $G_s$ family | Adenylate cyclase stimulation |
| | | | | | Comments: Activation of MAP kinase leading to immediate early gene expression[14,26]. | | |
| UK14304 | a2AR | | Full agonist | $G_i/G_o$ family | Adenylate cyclase inhibition | $G_s$ family | Adenylate cyclase stimulation |
| | | | | | Potassium channel | | Comments: The physiological significance of this mechanism is unknown. |
| | | | | | Calcium channel | | |
| | | | | | Phospholipase $A_2$ stimulation | | |
| | a2B | | Partial agonist | $G_i/G_o$ family | | $G_s$ family | |
| | a2C | | Partial agonist | $G_i/G_o$ family | | $G_s$ family | |
| | | | | | CLUSTER 3 | | |
| Somatostatin | SST | | | $G_i/G_o$ family | Adenylate cyclase inhibition | $G_i/G_o$ family | Adenylate cyclase stimulation |
| | SSTR1 | | | G protein independent mechanism | Potassium channel | $G_q/G_{11}$ family | Phospholipase C stimulation |
| | SSTR2 | | | G protein (identity unknown) | Calcium channel | G protein independent mechanism | Potassium channel |
| | SSTR3 | | | | Comments: G protein independent: Inhibition of phosphoinositide 3-kinase | G protein (identity unknown) | Calcium channel |

Figure 16 (continued)

| | | | |
|---|---|---|---|
| | activity through direct molecular interactions (and competition) between sst2 first intracellular loop and the regulatory PI3K p85 subunit or filamin-A [19,97]. | | |
| | G-protein-dependent activation of ERK and PI3K activity in sst2-transfected CHO cells [75] and [59]. | Phospholipase D stimulation | |
| SSTR4 | | | Comments: PLC activation is via the $G_q$ G-protein. |
| SSTR5 | | | K+ channel activation and $Ca^{2+}$ channel inhibition is via $G_i/G_o$. |
| | | | There is also protein tyrosine phosphatase (PTP) activation via a PTX-insensitive G-protein. |
| | | | sst2 activates PLC via a mechanism involving Galpha14 and has also been shown to activate PLD in clonal beta cells HIT-T15 [35,62,84]. |
| | | | Adenylate cyclase stimulation has been reported at very high agonist doses in overexpression systems. |
| | | | Other downstream events reported to be consequential to somatostatin binding include inhibition of the PI3K-mTOR pathway and cap-dependent translation |

Figure 16 (continued)

| | | | | | [11,30,140], activation of the protein-tyrosine phosphatases SHP-1, SHP-2 or PTPeia [13,49] and inhibition of eNOS activity [8]. |
|---|---|---|---|---|---|
| MNK1 | FPR2/ALX | Full Agonist | $G_i/G_o$ family | Phospholipase C stimulation | Phospholipase C stimulation |
| | | | | Phospholipase $A_2$ stimulation | Phospholipase $A_2$ stimulation |
| | | | | Phospholipase D stimulation | Phospholipase D stimulation |
| | | | | | $G_q/G_{11}$ family |
| | | | | | Comments: FPR2/ALX joins a small group of chemoattractant/ chemokine receptors to share a mechanism of using CD38-dependent cyclic ADP ribose for calcium flux and chemotaxis. Many of these receptors also couple to $G_q$ in addition to Gproteins. |
| | FPR | | | | |
| | FPRL1 | | | | |
| | | | CLUSTER 4 | | |
| Apelin-17 | APJR | Agonist | $G_i/G_o$ family | Adenylate cyclase inhibition | |
| | | | | Comments: Downstream of $G_i$ activation apelin triggers a sharp increase in intracellular $Ca^{2+}$ levels and activates ERKs via a PKC dependent pathway. Apelin dependent activation of ERK and PI3Kinase leads to activation of p70S6 kinase in endothelial cells. | |

Figure 16 (continued)

| BP554 | 5-HT1A | | G$_i$/G$_o$ family | Adenylate cyclase inhibition |
| --- | --- | --- | --- | --- |
| | | | | The 5-HT1A has also been found to stimulate cAMP accumulation via Gi2 and ACII |
| Quinpirole | D3R | Full Agonist | G$_i$/G$_o$ family | Adenylate cyclase inhibition |
| | D2R | Full Agonist | G$_i$/G$_o$ family | Adenylate cyclase inhibition, potassium channel |
| | D4R | Full Agonist | G$_i$/G$_o$ family | Adenylate cyclase inhibition |
| | 5-HT1A | Full Agonist | G$_i$/G$_o$ family | Adenylate cyclase inhibition |

KITS FOR CLASSIFYING A SUBJECT HAVING OR AT RISK FOR DEVELOPING IDIOPATHIC SCOLIOSIS

CROSS REFERENCE TO RELATED APPLICATIONS

The present application is a national phase entry under 35 U.S.C. § 371 of International Application No. PCT/CA2014/050853 filed Sep. 9, 2014, published as International Publication No. WO 2015/032005 A1, which claims priority from U.S. Provisional Application No. 61/875,162, filed Sep. 9, 2013 and U.S. Provisional Application No. 61/879,314, filed Sep. 18, 2013, all of which are incorporated herein by reference.

STATEMENT REGARDING FEDERALLY SPONSORED RESEARCH OR DEVELOPMENT

N.A.

FIELD OF THE INVENTION

The present invention relates to markers for idiopathic scoliosis diagnosis and prognosis. More specifically, the present invention is concerned with methods of identifying subjects at risk of developing scoliosis and methods of classifying subjects having or at risk of developing scoliosis according to their GiPCR mediated cellular responses in the presence of osteopontin (OPN).

BACKGROUND OF THE INVENTION

Idiopathic Scoliosis (IS) (e.g., Infantile Idiopathic Scoliosis, Juvenile Idiopathic Scoliosis or Adolescent Idiopathic Scoliosis (AIS)) is a spine deformity of unknown cause generally defined as a lateral curvature greater than 10 degrees accompanied by a vertebral rotation[1]. The condition affects 4% of the paediatric population and is most commonly diagnosed between the ages of 9 to 13 years[2,3,4]. The diagnosis is primarily of exclusion and is made only after ruling out other causes of spinal deformity such as vertebral malformation, neuromuscular or syndromic disorders. Traditionally, the trunkal asymmetry is revealed by Adams forward bending test and measured with scoliometer during physical examination[5]. The diagnosis can then be confirmed by radiographic observation of the curve and the angle measurement using the Cobb method[6].

Once diagnosed, the primary concern for physicians in managing scoliotic children is whether the curve will progress. Indeed, the curve progression is often unpredictable and is more frequently observed among girls than in boys[7]. If untreated, the curve can progress dramatically, creating significant physical deformity and even cardiopulmonary problems. These manifestations become life threatening when the curve exceeds 70 degrees[8,9]. The current treatment options to prevent or stop curve progression include bracing and surgery. In general, bracing is recommended for curves between 25 and 40 degrees, while surgery is reserved for curve greater than 45 degrees or curves that are unresponsive to bracing.

Today in the United States there are approximately one million children between ages 10 and 16 with some degree of IS and about 100 000 children in Canada are diagnosed with IS. The total cost of diagnosis and monitoring of the scoliotic children by X-ray exposure is over $2.5 billion dollars annually in North America. Approximately, 10% of children diagnosed with idiopathic scoliosis have curve progression requiring corrective surgery[10]. About 29,000 scoliosis surgeries are done every year in North America, resulting in significant psychological and physical morbidity.

Currently, there is no approved method or test available to identify subjects at risk of developing IS or to predict which affected individuals will show a curve progression that will require surgery. Therefore, the application of current treatments, such as bracing or surgical correction, is delayed until a significant deformity is detected or until a significant progression is clearly demonstrated, resulting in a delayed, less than optimal treatment and often important psychological sequels (Scoliosis Research Society) Morbidity & Mortality Committee annual Report 1997). All diagnosed children are subjected to multiple radiographs over several years, usually until they reach skeletal maturity. It is estimated that the typical patients with scoliosis will have approximately 22 radiological examinations over a 3-year period[11]. Because of the potential risk of multiple radiographic examinations, the alternative approaches that could allow performing the prognosis of idiopathic scoliosis without exposing children to ionizing radiation are strongly desirable.

The major limitation in developing prognostic tests that could facilitate treatment choices for patients is the heterogeneous nature of IS. At the clinical level, the heterogeneity of IS is clearly illustrated by the variability of curve patterns, localisations and curve magnitude even in families with multiple affected members. In absence of reliable IS phenotypes, there is a need to understand better the molecular changes associated with disease onset and spinal deformity progression. Molecular definition of disease is rapidly replacing traditional pathology-based disease descriptions in part because of its utility in identifying the optimal treatment regimen for patients.

In this regard, the present inventors have previously discovered that scoliotic patients and subjects at risk of developing scoliosis are less responsive to Gi protein (inhibitory guanine nucleotide binding protein in G protein coupled receptors (GPCRs) also known as $G_i$ alpha subunit) stimulation when compared with healthy control subjects. The presence of a general differential Gi-signaling dysfunction allowed to stratify/classify patients into three functional groups (FG1, FG2 and FG3) representing distinct biological endophenotypes. This impairment was detected in all cell types tested including bone-forming cells; muscle-forming cells and blood cells (e.g., PBMCs). Furthermore, because the response impairment is generalized and not specific to a particular receptor, any Gi-PCR agonist can be used to classify subjects.

A first classification method is based on the percentage of degree of reduction (inhibitory response) relative to control group. The classification ranges were fixed between about 10 and 40% (or below 40%) of reduction of response relative to control group for FG3, about 40 and 60% for FG2 and above about 60% (e.g., between about 60% and 90%) for FG1. The same the classification ranges can be expressed as the percentage of maximal response relative to the control (as opposed to the % of reduction of response relative to the control). In such a case, the ranges are fixed between about 10-40% for FG1, about 40 and 60% for FG2 and about 60-90% for FG3. Both classification ranges can be used interchangeably (See Moreau et al., 2004; Akoume et al., 2010; Azeddine et al., 2007; Letellier et al., 2008; WO2003/073102, WO2010/040234 to Moreau, which are incorporated herein by reference in their entirety).

More recently, the present inventors have modified this approach by demonstrating that the three functional groups can clearly be distinguished according to the profile of imbalance between response to Gi and Gs stimulation (i.e. Gi response minus Gs response or Gi/Gs-See PCT/CA2014/ 050562, which is incorporated herein by reference). It was found that the response to Gi stimulation predominated in FG3, while no substantial imbalance (or a very small imbalance) was observed in FG2. In contrast, FG1 exhibited predominance for response to Gs stimulation. In addition, evidence was provided to the effect that patients belonging to the FG2 endophenotype are more at risk of progressing to the point of needing surgery[17].

The differences in Gi-mediated cellular response observed among the three endophenotypes is (at least partly) a consequence of differences observed at the level of Gi protein phosphorylation. When Giα proteins are phosphorylated they become inactive. The inventors have shown that the degree of serine phosphorylation of Giα proteins can alternatively be used to classify subjects into a specific functional groups. In FG1 subjects, all Giα proteins (Giα1-3) are phosphorylated and their level of serine phosphorylation is substantially higher than in control subjects. In FG2 Giα1 and Giα2 are phosphorylated, the level of Giα1 and Giα2 phosphorylation is higher than in control subjects and most Giα3 proteins are not phosphorylated and thus, remain functional. Finally, in FG3 subjects Giα2 and Giα3 are phosphorylated, their level of phosphorylation is higher than in control subjects and most Giα1 are not phosphorylated and thus remain functional[18].

The assessment of an imbalance between Gi and Gs coupled receptor signaling (as opposed to the assessment of a Gi-coupled receptor signaling impairment), greatly simplifies the risk assessment and endophenotype (functional group) assessment by eliminating the need of a reference signal from a control subject. The establishment of a reference signal is often difficult and may sometimes constitute an obstacle because the control subject(s) from whom the reference signal is derived should preferably match with age, gender and medication, if any.

Although the methods of diagnosing subjects suffering from scoliosis or at risk of developing scoliosis described above provide significant advantages, certain subjects are more difficult to classify into a functional group (FG1, FG2 or FG3) because their response to Gi stimulation or degree of Gi/Gs imbalance approaches the cut-off values defined for the classification. Furthermore, determining the phosphorylation level/pattern of Giα proteins may be more difficult to implement in a clinical setting. Therefore there is a need for novel alternative or complementary methods for classifying subjects having diseases involving spinal deformities (e.g., scoliosis, such as IS) and for diagnosing a predisposition to scoliosis.

The present description refers to a number of documents, the content of which is herein incorporated by reference in their entirety.

SUMMARY OF THE INVENTION

Accordingly, there are provided novel alternative methods of identifying subjects at risk of developing IS and of classifying IS subjects into a specific IS functional group. The methods can be used alone or in combination with one or more previous methods to increase the specificity of the functional group identification which in turn can increase the specificity and sensitivity of risk prediction and/or facilitate/improve the application of preventive or treatment measures. Once a subject is identified as belonging to a given functional group, treatment and preventive measures can be adapted to his/her specific endophenotype.

Applicants demonstrate herein for the first time a differential effect of osteopontin (OPN) on the response to Gi stimulation among functional groups in IS. Subjects suffering from IS can be classified into a particular functional group based on their Gi mediated response to OPN. Furthermore, subjects at risk of developing IS may also be identified and classified. Indeed, it was found that in the presence of OPN, the response to Gi stimulation increases in FG1, while it decreases in FG2 and FG3. Furthermore, the response to Gi stimulation decreases to a higher extent in the FG2 than in the FG3 functional group.

In a second aspect, Applicants show herein that IS subjects or subjects at risk of developing IS can be classified according to their impedance signature (i.e., the shape of their impedance curve) in response to GiPCR stimulation with four Gi-coupled receptor clusters (GiPCR clusters). By using cluster II GiPCR agonists (e.g., agonists to the CB2R α2AR, α2BR and α2C receptors), it is possible to rapidly distinguish subjects belonging to the FG1 functional group over those belonging to the FG2 and FG3 functional groups. Indeed, subjects belonging to the FG1 group show a characteristic negative impedance phase in response to Gi-PCR cluster II stimulation, which is not present for subjects belonging to the FG2 and FG3 groups. Hence, this method can also be useful to identify or classify subjects which are difficult to identify or classify using other methods such as subjects which have a Gi cellular response considered to be borderline between two groups.

In a third aspect, the present inventors have found that IS subjects or subjects at risk of developing IS can also be classified according to their Gi-mediated response in the presence of inhibitors/antagonists of Gi proteins such as Pertussis Toxin (PTX) and GP Ant-2, which inactivates Gi/G$_o$ proteins. The IC50 value for GP Ant-2 is smaller for FG1 subjects than for FG3 subjects. FG2 subjects have an IC50 value for GP-Ant 2 which is between that of FG1 and FG3 subjects. Similar results were obtained with the G-protein antagonist PTX, although the differences were less important. Unexpectedly, at high concentrations of PTX subjects belonging to the FG1 functional group can also be rapidly distinguished over FG2 and FG3 subjects based on their response to cluster I and/or cluster II GiPCR agonists. Indeed, at high PTX concentrations, stimulation by cluster I or cluster II agonists results in a cellular response which is substantially higher than the response observe in FG2 and FG3 subjects (as opposed to a lower/decreased response normally observed at lower concentrations of PTX). This difference/shift in the FG1 response was not observed with the GP Ant-2 antagonist.

Accordingly, in an aspect there is provided a method of classifying a subject having idiopathic scoliosis (IS) or at risk of developing IS comprising: (a) determining the cellular response to Gi stimulation in a cell sample from the subject in the presence of OPN; (b) determining the cellular response to Gi stimulation in a cell sample from the subject in the absence of OPN; and (c) comparing the cellular response obtained in the presence of OPN with the cellular response obtained in the absence of OPN, whereby the comparing step enables the classification of the subject into one IS functional group.

In a specific embodiment of the method, an increase in cellular response following Gi-stimulation in the presence of OPN in the sample is indicative that the subject belongs to functional group FG1; and wherein a decrease in cellular response following Gi-stimulation in the presence of OPN is indicative that the subject belongs to functional group FG2 or FG3.

In another specific embodiment, step (c) comprises determining the Fold effect (Fe) of OPN on the cellular response to Gi stimulation. In another specific embodiment, a Fe value above about 100% is indicative that the subject belongs to IS functional group FG1; a Fe value below about 50% is indicative that the subject belongs to IS functional group FG2 and a Fe value below about 95% and above about 50% is indicative that the subject belongs to IS functional group FG3. In another specific embodiment, the method is used to classify subjects found to be borderline according to a previously used alternative classification method, into one IS functional group.

The present invention also concerns a method of classifying a subject having idiopathic scoliosis (IS) or at risk of developing IS comprising: (a) contacting a cell sample from the subject with i) an agonist of cluster I or cluster II GiPCR; and ii) Pertussis toxin (PXT); (b) Determining the cellular response to Gi stimulation; and (c) Classifying the subject into a IS functional group according to the subject's cellular response profile. In an embodiment, step (c) comprises (i) classifying the subject into a first functional group when the cellular response is above the cellular response of a control sample; or (ii) Classifying the subject into a second functional group when the cellular response is substantially comparable to the cellular response of a control sample. In an embodiment, the cluster I GiPCR is lysophosphatidic acid receptor (LPAR), melatonin receptor (MT1 or MT2), mu-opioid receptor (OR) or adenosine receptor (AR). In an embodiment, the agonist is melatonin, iodomelatonin, phenylmelatonin, LPA, DAMGO or NECA. In a particular embodiment, the cluster II GiPCR is cannabinoid receptor (CB2R) or a α2-Adrenoreceptor (α2AR). In an embodiment, the agonist is CB65 or UK14304.

In another specific embodiment of the above methods, the cellular response to Gi stimulation is determined by measuring cellular impedance. In another specific embodiment, the cellular impedance is measured by cellular dielectric spectroscopy.

The present invention further provides a method of classifying a subject having idiopathic scoliosis IS or at risk of developing IS comprising: (a) contacting a cell sample from the subject with an agonist of a cluster II GiPCR; (b) determining the cellular response to Gi protein stimulation by cellular impedance; and (c) classifying the subject into a IS functional group according to the subject's cellular impedance profile. In an embodiment, step (c) comprises: (i) classifying the subject into a first IS functional group when the cellular impedance profile comprises a phase of negative impedance followed by a phase of positive impedance; and (ii) classifying the subject into a second IS functional group when the cellular impedance profile does not comprise a phase of negative impedance. In an embodiment the cluster II GiPCR is cannabinoid receptor (CB2R) or a α2-Adrenoreceptor (α2AR). In an embodiment, the agonist is CB65 or UK14304.

In another specific embodiment, the method methods of the present invention further comprises classifying borderline subjects into one IS functional group by using an alternative classification method. In another specific embodiment, the alternative classification method is performed prior to step (a) of the method.

In another specific embodiment, the alternative classification method comprises determining the difference between cellular responses to Gi and Gs protein stimulations in the cell sample from the subject. In another specific embodiment, determining the difference between cellular responses to Gi and Gs protein stimulations comprises measuring cAMP cellular concentration produced by each of Gi and Gs protein stimulations.

In another specific embodiment, determining the difference between cellular responses to Gi and Gs protein stimulations comprises measuring cellular impedance. In another specific embodiment, the cellular impedance is measured by cellular dielectric spectroscopy (CDS). In another specific embodiment, determining the difference between cellular responses to Gi and Gs protein stimulations is performed by determining the $\Delta G$ in the sample from the subject. In another specific embodiment, the $\Delta G$ is determined by measuring cellular impedance and the cellular impedance is measured by CDS, and wherein i) a $\Delta G$ below $-10$ is indicative that the subject belongs to IS functional group FG1; ii) a $\Delta G$ above $-10$ and below $+10$ is indicative that the subject belongs to IS functional group FG2; and iii) a $\Delta G$ above $+10$ is indicative that the subject belongs to IS functional group FG3.

In another specific embodiment, determining the difference between cellular responses to Gi and Gs protein stimulations is performed by determining a ratio between cellular responses to Gi and Gs protein stimulations (Gi/Gs). In another specific embodiment, i) a ratio below about 0.5 is indicative that the subject belongs to IS functional group FG1; ii) a ratio between about 0.5 and 1.5, is indicative that the subject belongs to IS functional group FG2; and iii) a ratio above 1.5 is indicative that the subject belongs to IS functional group FG3

In another specific embodiment, the alternative method comprises determining the magnitude of a cellular response to Gi stimulation in the cell sample relative to a control sample. In another specific embodiment, i) a reduction of between about 60-90% of the cellular response to Gi stimulation relative to control is indicative that the subject belongs to IS functional group FG1; ii) a reduction of between about 40-60% of the cellular response to Gi stimulation relative to control is indicative that the subject belongs to IS functional group FG2; and iii) a reduction between about 10-40% of the cellular response to Gi stimulation relative to control is indicative that the subject belongs to IS functional group FG3. In another specific embodiment, i) a reduction above 60% of the cellular response to Gi stimulation relative to control is indicative that the subject belongs to IS functional group FG1; ii) a reduction of between about 40-60% of the cellular response to Gi stimulation relative to control is indicative that the subject belongs to IS functional group FG2; and iii) a reduction below about 40% of the cellular response to Gi stimulation relative to control is indicative that the subject belongs to IS functional group FG3. In another specific embodiment, the magnitude of a cellular response to Gi stimulation is determined by measuring cellular impedance. In another specific embodiment, cellular impedance is measured by cellular dielectric spectroscopy (CDS). In another specific embodiment, the alternative method comprises measuring cAMP concentration. In another specific embodiment, i) an increase in cAMP concentration relative to baseline is indicative that the subject belongs to IS functional group FG1, ii) no significant or weak reduction in cAMP concentration relative to baseline is indicative that the subject belongs to IS functional group FG2; and iii) a reduction in cAMP concentration relative to baseline is indicative that the subject belongs to IS functional group FG3.

In another specific embodiment, the alternative method comprises determining the phosphorylation state of Giα proteins in the cell sample. In another specific embodiment, i) the presence of serine phosphorylated Giα1, Giα2 and Giα3 proteins (or of an increase in or substantially higher level of serine phosphorylated Giα1, Giα2 and Giα3 proteins as compared to a control sample from a subject not having IS or not at risk of developing IS) is indicative that the subject belongs to IS functional group FG1; ii) an absence of serine phosphorylation in Giα3 proteins (or a level of serine phosphorylation in Giα3 proteins comparable or lower to the level of serine phosphorylation in Giα3 proteins in a control sample from a subject not having IS or not at risk of developing IS) is indicative that the subject belongs to IS functional group FG2; and iii) an absence of serine phosphorylation in Giα1 proteins (or a level of serine phosphorylation in Giα1 protein comparable or lower to the level of serine phosphorylation in Giα1 proteins in a control sample from a subject not having IS or not at risk of developing IS) is indicative that the subject belongs to IS functional group FG3.

In another specific embodiment, the alternative method comprises determining cellular proliferation of the cell sample relative to a control sample. In another specific embodiment, i) a reduction in cellular proliferation of about 50% or more relative to control is indicative that the subject belongs to IS functional group FG1; ii) a reduction in cellular proliferation between about 25% and 45% relative to control is indicative that the subject belongs to IS functional group FG2; and iii) a reduction in cellular proliferation of about 25% or less relative to control is indicative that the subject belongs to IS functional group FG3.

In accordance with another aspect of the present invention, there is provided a method of predicting the risk of developing IS comprising: a) determining the cellular response to Gi stimulation in a cell sample from the subject in the presence of OPN; b) determining the cellular response to Gi stimulation in a cell sample from the subject in the absence of OPN; and c) comparing the cellular response obtained in the presence of OPN with the cellular response obtained in the absence of OPN, whereby the comparing step enables the prediction of the risk of developing IS. In a specific embodiment, an increase in cellular response following Gi-stimulation in the presence of OPN in the sample is indicative that the subject belongs to functional group FG1; and wherein a decrease in cellular response following Gi-stimulation in the presence of OPN is indicative that the subject belongs to functional group FG2 or FG3 and wherein identification of the subject as belonging to the FG2 functional group indicates that the subject is at risk of developing severe IS. In another specific embodiment, step (c) comprises determining the Fold effect (Fe) of OPN on the cellular response to Gi stimulation. In another specific embodiment, a Fe value above about 100% is indicative that the subject belongs to IS functional group FG1; a Fe value below about 50% is indicative that the subject belongs to IS functional group FG2 and a Fe value below about 95% and above about 50% is indicative that the subject belongs to IS functional group FG3.

The present invention further relates to method of determining the risk of developing IS in a subject comprising: (a) contacting a cell sample from the subject with i) an agonist of cluster I or cluster II GiPCR; and ii) Pertussis toxin (PXT); (b) determining the cellular response to Gi stimulation; and (c) classifying the subject into a IS functional group according to the subject's cellular response profile. In an embodiment, step (c) comprises (i) classifying the subject into a first functional group when the cellular response is above the cellular response of a control sample; or (ii) classifying the subject into a second functional group when the cellular response is substantially comparable to the cellular response of a control sample. In a particular embodiment, the cluster I GiPCR is lysophosphatidic acid receptor (LPAR), melatonin receptor (MT1 or MT2), mu-opioid receptor (OR) or adenosine receptor (AR). In an embodiment, the agonist is melatonin, iodomelatonin, phenylmelatonin, LPA, DAMGO or NECA. In an embodiment, the cluster II GiPCR is cannabinoid receptor (CB2R) or a α2-Adrenoreceptor (α2AR). In a particular embodiment, the agonist is CB65 or UK14304. In an embodiment, the identification of the subject as belonging to the FG2 functional group indicates that the subject is at risk of developing severe IS.

In another specific embodiment, the cellular response to Gi stimulation is determined by measuring cellular impedance. In another specific embodiment, the cellular impedance is measured by cellular dielectric spectroscopy.

The present invention also relates to a method of determining the risk of developing IS in a subject comprising: (a) contacting a cell sample from the subject with an agonist of a cluster II Gi-PCR; (b) determining the cellular response to Gi protein stimulation by cellular impedance; and (c) classifying the subject into a IS functional group according to the subject's cellular impedance profile. In an embodiment, step (c) comprises: (i) classifying the subject into a first IS functional group when the cellular impedance profile comprises a phase of negative impedance followed by a phase of positive impedance; and (ii) classifying the subject into a second IS functional group when the cellular impedance profile does not comprise a phase of negative impedance. In an embodiment the cluster II GiPCR is cannabinoid receptor (CB2R) or a α2-Adrenoreceptor (α2AR). In an embodiment, the identification of the subject as belonging to the FG2 functional group indicates that the subject is at risk of developing severe IS.

In another specific embodiment, the method further comprises classifying borderline subjects into one IS functional group by using an alternative classification method. In another specific embodiment, the alternative classification method is performed prior to step (a) of the method of the present invention. In another specific embodiment, the alternative classification method comprises determining the difference between cellular responses to Gi and Gs protein stimulations in the cell sample from the subject. In another specific embodiment, determining the difference between cellular responses to Gi and Gs protein stimulations comprises measuring cAMP cellular concentration produced by each of Gi and Gs protein stimulations. In another specific embodiment, determining the difference between cellular responses to Gi and Gs protein stimulations comprises measuring cellular impedance. In another specific embodiment, the cellular impedance is measured by cellular dielectric spectroscopy (CDS). In another specific embodiment, determining the difference between cellular responses to Gi and Gs protein stimulations is performed by determining the $\Delta G$ in the sample from the subject. In another specific embodiment, the $\Delta G$ is determined by measuring cellular impedance and the cellular impedance is measured by CDS, and wherein i) a $\Delta G$ below $-10$ is indicative that the subject belongs to IS functional group FG1; ii) a $\Delta G$ above $-10$ and below $+10$ is indicative that the subject belongs to IS functional group FG2; and iii) a $\Delta G$ above $+10$ is indicative that the subject belongs to IS functional group FG3.

In another specific embodiment, determining the difference between cellular responses to Gi and Gs protein stimulations is performed by determining a ratio between cellular responses to Gi and Gs protein stimulations (Gi/Gs). In another specific embodiment, i) a ratio below about 0.5 is indicative that the subject belongs to IS functional group FG1; ii) a ratio between about 0.5 and 1.5, is indicative that the subject belongs to IS functional group FG2; and iii) a ratio above 1.5 is indicative that the subject belongs to IS functional group FG3.

In another specific embodiment, the alternative method comprises determining the magnitude of a cellular response to Gi stimulation in the cell sample relative to a control sample. In another specific embodiment, i) a reduction of between about 60-90% of the cellular response to Gi stimulation relative to control is indicative that the subject belongs to IS functional group FG1; ii) a reduction of between about 40-60% of the cellular response to Gi stimulation relative to control is indicative that the subject belongs to IS functional group FG2; and iii) a reduction between about 10-40% of the cellular response to Gi stimulation relative to control is indicative that the subject belongs to IS functional group FG3. In another specific embodiment, i) a reduction above 60% of the cellular response to Gi stimulation relative to control is indicative that the subject belongs to IS functional group FG1; ii) a reduction of between about 40-60% of the cellular response to Gi stimulation relative to control is indicative that the subject belongs to IS functional group FG2; and iii) a reduction below about 40% of the cellular response to Gi stimulation relative to control is indicative that the subject belongs to IS functional group FG3.

In another specific embodiment, the magnitude of a cellular response to Gi stimulation is determined by measuring cellular impedance. In another specific embodiment, cellular impedance is measured by cellular dielectric spectroscopy (CDS). In another specific embodiment, the alternative method comprises measuring cAMP concentration. In another specific embodiment, i) an increase in cAMP concentration relative to baseline is indicative that the subject belongs to IS functional group FG1, ii) no significant or weak reduction in cAMP concentration relative to baseline is indicative that the subject belongs to IS functional group FG2; and iii) a reduction in cAMP concentration relative to baseline is indicative that the subject belongs to IS functional group FG3.

In another specific embodiment, the alternative method comprises determining the phosphorylation state of Giα proteins in the cell sample. In another specific embodiment, i) the presence of serine phosphorylated Giα1, Giα2 and Giα3 proteins (or of a substantially higher level of serine phosphorylated Giα1, Giα2 and Giα3 proteins as compared to a control sample not having IS or not at risk of developing IS) is indicative that the subject belongs to IS functional group FG1; ii) an absence of serine phosphorylation in Giα3 proteins (or a level of serine phosphorylation in Giα3 protein comparable or lower to the level of serine phosphorylation in Giα3 proteins in a control sample from a subject not having IS or not at risk of developing IS) is indicative that the subject belongs to IS functional group FG2; and iii) an absence of serine phosphorylation in Giα1 proteins (or a level of serine phosphorylation in Giα1 proteins comparable or lower to the level of serine phosphorylation in Giα1 proteins in a control sample from a subject not having IS or not at risk of developing IS) is indicative that the subject belongs to IS functional group FG3. In another specific embodiment, the alternative method comprises determining cellular proliferation of the cell sample relative to a control sample. In another specific embodiment, i) a reduction in cellular proliferation of about 50% or more relative to control is indicative that the subject belongs to IS functional group FG1; ii) a reduction in cellular proliferation between about 25% and 45% relative to control is indicative that the subject belongs to IS functional group FG2; and iii) a reduction in cellular proliferation of about 25% or less relative to control is indicative that the subject belongs to IS functional group FG3.

In accordance with another aspect of the present invention, there is provided a method of selecting a preventive measure, treatment or follow-up schedule for a subject suffering from IS or at risk of developing IS comprising classifying the subject using one or more of the above-noted methods: a) When the subject is classified as belonging to the FG1 functional group: i) the level of OPN in said subject is increased; ii) the level of HA in said subject is increased; iii) the level of CD44 in said subject is decreased; and/or iv) the frequency of assessment of scoliosis progression is decreased; b) when the subject is classified as belonging to the FG2 functional group: i) the level of OPN is said subject is decreased; ii) the level of HA in said subject is decreased; and/or iii) the level of CD44 in said subject is increased; iv) the frequency of assessment of scoliosis progression is increased; and/or v) the subject is prescribed corrective surgery prior to reaching a scoliosis with a cobb angle of 45 degree; or c) when the subject is classified as belonging to the FG3 functional group: i) the level of OPN is said subject is decreased; ii) the level of HA in said subject is decreased; iii) the level of CD44 in said subject is increased; and/or iv) the frequency of assessment of scoliosis progression is decreased.

In an embodiment, increasing the level of OPN comprises performing massages such as by applying pulsative compressive pressure to a body part of the subject. In an embodiment, increasing the level of OPN comprises administering OPN or a fragment thereof or derivative thereof to the subject. In an embodiment, increasing the level of OPN comprises applying low intensity pulsed ultrasound (LIPUS) to the subject. In a specific embodiment, increasing the level of HA comprises administering to the subject HA supplements or complying to a HA-rich diet. In a specific embodiment, decreasing the level of HA comprises complying to a HA-poor diet. In an embodiment decreasing OPN level comprises brace treatment. In an embodiment decreasing OPN level comprises administering to the subject selenium supplements, melatonin or PROTANDIM™. In an embodiment decreasing OPN level comprises accupoint heat sensitive moxibustion, heat therapy with pad, thermal bath and electroacupuncture. In a specific embodiment decreasing the frequency of assessment of scoliosis progression comprises performing less than 22 radiological examinations within the 3 years following classification.

In a specific embodiment of the methods, the subject is a subject pre-diagnosed with IS. In another specific embodiment, the subject is asymptomatic. In another specific embodiment, the subject is a subject having at least one family member suffering from IS. In another specific embodiment, the cell sample comprises osteoblasts, chondrocytes, myoblasts and/or peripheral blood mononuclear cells (PBMCs). In another specific embodiment, the cell sample comprises PBMCs. In another specific embodiment, the PBMCs comprise lymphocytes. In another specific embodiment, the PBMCs are frozen PBMCs. In another specific embodiment, the PBMCs are fresh PBMCs. In another specific embodiment, the Gi stimulation comprises contacting the cells with somatostatin. In another specific embodiment, the Gi-stimulation comprises contacting the cells with a cluster I, cluster II, cluster III and/or cluster IV receptor agonist. In an embodiment the cluster I receptor is the melatonin receptor (MT1 or MT2), lysophosphatidic acid receptor (LPAR), mu-opioid receptor (OR) or the adenosine receptor (AR). In an embodiment, the cluster I agonist is LPA, DAMGO or NECA. In an embodiment, the cluster II receptor is α2 adrenergic receptor or the type 2 cannabinoid receptor (CB2R). In an embodiment, the cluster II agonist is CB65 or UK14304. In an embodiment, the cluster III receptor is the somatostatin receptor (SSTR) or the formyl peptide receptor 2 (FPR2). In an embodiment, the cluster III agonist is somatostatin or MMK1. In an embodiment, the cluster iv receptor is the Apelin receptor (APJR), the 5-HT1 receptor (5-HT1R) or the domapine D2 receptor (D2R). In an embodiment, the cluster iv agonist is Apelin-17, BP554 or quinpirole. In another specific embodiment, the Gi stimulation comprises contacting the cells with a cluster I or cluster II agonist. In another specific embodiment, the Gs stimulation comprises contacting the cells with isoproterenol. In another specific embodiment, the IS is Adolescent idiopathic scoliosis (AIS).

In accordance with another aspect of the present invention, there is provided a kit for classifying a subject having idiopathic scoliosis (IS) or at risk of developing IS or for predicting the risk of developing IS comprising: OPN; and one or more ligands for Gi stimulation.

In another aspect of the present invention, there is provided a kit for classifying a subject having idiopathic scoliosis (IS) or at risk of developing IS or for predicting the risk of developing IS comprising: a cluster II GiPCR (e.g., CB2R or α2AR) agonist (e.g., CB65 or UK14304). In an embodiment, the kit further comprises at least one of i) a cluster iv GiPCR (e.g., APJR, 5-HT1R or D2R) agonist (e.g., Apelin-17 BP554 or quinpirole); ii) OPN; iii) PTX and iv) instructions for classifying the subject or for predicting the risk of developing IS.

In another aspect of the present invention, there is provided a kit for classifying a subject having idiopathic scoliosis (IS) or at risk of developing IS or for predicting the risk of developing IS comprising: i) a cluster I GiPCR (e.g., LPAR, OR, A1R or melatonin receptor) and/or cluster II GiPCR (e.g., CB2R or α2AR) agonist (e.g., melatonin, LPA, DAMGO, NECA, CB65 or UK14304); and ii) PTX. In an embodiment, the kit further comprises at least one of i) a cluster III GiPCR agonist (e.g., somatostatin, MMK1); ii) a cluster IV GiPCR agonist (Apelin-17, BP554 or quinpirole); iii) OPN; and/or iv) instructions for classifying the subject or for predicting the risk of developing IS.

In an embodiment, the above-noted kits are for predicting the risk of developing IS.

In another specific embodiment, the above-noted kits further comprise: a ligand for Gs stimulation; one or more antibodies for detecting Giα phosphorylation (e.g., an antibody specific for Giα1, Giα2 and/or Giα3); hyaluronic acid (HA) and/or instructions for classifying the subject or for predicting the risk of developing IS.

In an embodiment, the above-mentioned method is performed on more than one receptor coupled to a $G_i$ protein. In another embodiment, the above-mentioned method is performed using more than one ligand specific for a receptor coupled to a $G_i$ protein. In another specific embodiment, each ligand is specific to a different receptor coupled to a $G_i$ protein (e.g., 2, 3, 4, 5 or 6 ligands).

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 3 shows the percent (%) viability and cell concentration obtained in an illustrative experiment described in Examples 1 and 2 as determined using an automated cell counter and viability analyzer;

FIG. 8 shows a list of known Gi-protein coupled receptors;

FIG. 9 shows a list of known ligands to Gi-protein coupled receptors;

FIG. 15 summarizes alternative methods to classify IS subjects or subjects at risk of developing IS; and FIG. 16 Provides examples of Examples of clusters I (1) to IV (4) GiPCR ligands (e.g., full or partial agonists)

DESCRIPTION OF ILLUSTRATIVE EMBODIMENTS

Figure 1:
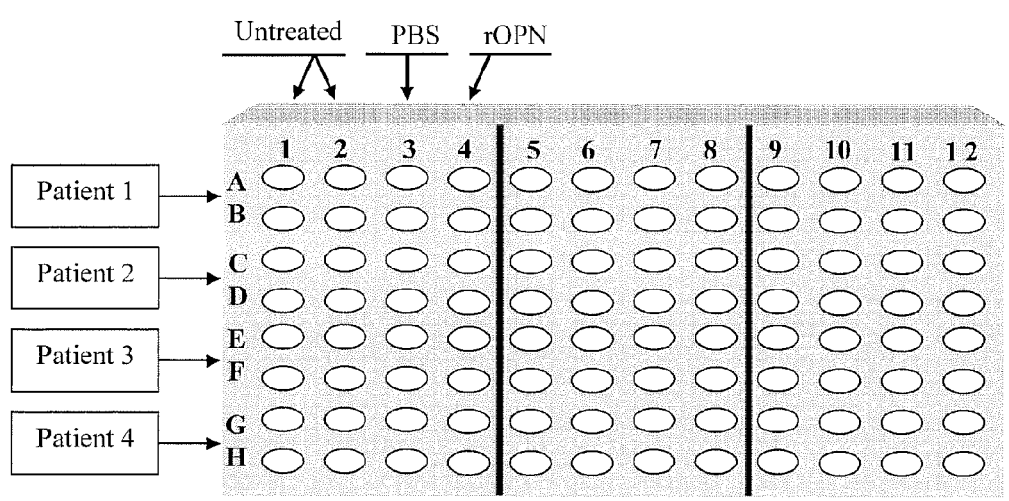
FIG. 1 shows an embodiment of a design for cell seeding in accordance with the present invention.

The Applicants have tested on a large number of pre-classified subjects (by one or more of previous stratification methods (e.g., response to Gi-agonist stimulation (cAMP production inhibition, impedance modifications (by cellular dielectric spectroscopy), etc.)) the effect of OPN on Gi response.

They have found that depending on the functional group (e.g., FG1, FG2 or FG3), subjects at risk of suffering from scoliosis (e.g., already diagnosed IS subjects or suspected IS subjects) have a different Gi-dependent cellular response in the presence of OPN. In the FG1 group the presence of OPN increases the cellular response following Gi stimulation, while in groups FG2 and FG3, the Gi-dependent cellular response is decreased in the presence of OPN. Groups FG2 and FG3 can be further distinguished based on the extent of the OPN effect.

Applicants have also found that subjects can further be distinguished based on their impedance profiles following Gi protein stimulation in four GiPCR clusters (I, II, III and IV). The impedance profile for each cluster has a different shape. In addition, in the case of GiPCR cluster II, only FG1 subject show an impedance profile comprising a characteristic negative impedance phase followed by a positive phase, thereby enabling to easily distinguish FG1 subjects from FG2 and FG3 subjects.

Furthermore, results presented herein show that FG1 subjects can further be distinguished over FG2 and FG3 subjects based on their cellular response to GiPCR cluster I and/or II stimulation in the presence of high concentration of PTX.

The methods of the present invention can be used to classify subjects already diagnosed with IS or to identify subject at risk of developing IS. For example asymptomatic subjects predisposed to IS (e.g., a subject having at least one family member suffering from IS) can be tested and their risk of developing scoliosis determined based e.g., on their impedance profile following Gi protein stimulation with Gi PCR cluster I, II, III and/or IV agonist (or ligand) or based on their Gi response in the presence of i) OPN; or ii) PTX. Their risk of developing severe scoliosis and of requiring surgery can also be determined based on their classification into a specific functional group. The present methods can be used alone or preferably in combination with one or more alternative methods of identifying the risk of developing IS and/or classifying subjects into one particular functional group (endophenotype). Combining the assessment of OPN effect, PTX effect (e.g., for cluster I and II GiPCR cellular response) or cluster II GiPCR stimulation on Gi cellular response with another method of identifying the risk of developing IS and/or classifying IS subjects allows to greatly improve the specificity of the method by allowing the classification of otherwise borderline subjects into one specific functional group (i.e., when one classification method alone did not enable to distinguish between two groups (e.g., between FG1 and FG2 or FG2 and FG3)). Thus, the precision of prior classification tests based on the response to Gi stimulation (or Gi/Gs imbalance) can thus further be improved by demonstrating a differential effect of osteopontin (OPN); or PTX on the response to Gi stimulation among functional groups or by looking at the impedance profiles in response to Gi protein stimulation in the presence of cluster I, II, III or iv GiPCR agonists.

The following predictive algorithm Table 6 is used in accordance with the present invention for the selection of agonists and GPCRs (Clusters I, II, III, IV) corresponding to functional classification of idiopathic scoliosis patients.

TABLE 6

|                         | Cluster I                                                                                                       | Cluster II                                      | Cluster III                                                                                                     | Cluster IV                                  |
|-------------------------|-----------------------------------------------------------------------------------------------------------------|-------------------------------------------------|-----------------------------------------------------------------------------------------------------------------|---------------------------------------------|
| FG1                     | LPA/Gs+                                                                                                         | CB65/Gs+                                        | Somatostatin/Gs+ and Gq+                                                                                        | Apelin-17/Gs− and Gq−                       |
| FG2                     | LPA/Gq+                                                                                                         | CB65/Gs− and Gq−                                | Somatostatin/Gq+                                                                                                | Apelin-17/Gs− and Gq−                       |
| FG3                     | LPA/Gq+                                                                                                         | CB65/Gs− and Gq−                                | Somatostatin/Gs+ and Gq+                                                                                        | Apelin-17/Gs− and Gq−                       |
| Cluster characteristics | Gs permissive (coupled) only for FG1 Gq permissive (coupled) only for FG2 and FG3 | Gs permissive (coupled) only for FG1 | Mainly Gq permissive (coupled) for all groups with weak Gs interaction (coupling) for FG1 and FG3 groups | Not permissive (not coupled) for Gq and Gs |

Cluster I GiPCR (and their ligands (e.g., agonists)) are coupled to Gs only for FG1, while being coupled to Gq for FG2 and FG3. Cluster II GiPCR (and their ligands (e.g., agonists)) are coupled to Gs, for FG1 only. Cluster III GiPCR (and their ligands (e.g., agonists)) are mainly coupled to Gq but also show a weak interaction with Gs for FG1 and FG3 groups. Cluster IV GiPCR (and ligands (e.g., agonists)) are not coupled to Gq and Gs.

Non-limiting examples of GICPR and their agonist for cluster I, II, III and IV are given in Table 7 below.

Accordingly, the present invention provides a method of classifying a subject having IS or at risk of developing IS (and/or of predicting the risk of developing IS) comprising: (a) determining the cellular response to Gi stimulation in a cell sample from the subject in the presence of OPN; (b) determining the cellular response to Gi stimulation in a cell sample from the subject in the absence of OPN; (c) comparing the cellular response obtained in the presence of OPN with the cellular response obtained in the absence of OPN; whereby the comparing step enables the classification of the subject into one IS functional group (and/or enables predicting the risk of developing IS).

In the above method based on the effect of OPN, classification into a specific functional group can be performed as follows. For example, when detecting an increase in cellular response following Gi-stimulation in the presence of OPN (when compared to in the absence of OPN), the subject is classified into the FG1 functional group; whereas when detecting a decrease in cellular response following Gi-stimulation in the presence of OPN (when compared to in the absence of OPN), the subject is classified into the FG2 or FG3 functional group depending on the extent of the OPN effect (the FG2 functional group being more sensitive to OPN).

Optionally and advantageously, the above-described methods may further comprise determining the fold effect (Fe) of OPN on Gi-mediated response which allows to more effectively distinguish between groups. The fold effect of OPN is determined by dividing the average of response magnitude to Gi stimulation in presence of OPN (RmGiOPN) with the average of response magnitude to Gi stimulation in the absence of OPN (RmGi) using the following formula:

$$Fe = 100 \times (RmGiOPN/RmGi)$$

According to the above formulae, a Fe value above about 100% is indicative that the subject belongs to IS functional group FG1; a Fe value below about 50% is indicative that the subject belongs to IS functional group FG2 and a Fe value below about 95% and above about 50% is indicative that the subject belongs to IS functional group FG3.

The present invention also provides a method of classifying a subject having idiopathic scoliosis (IS) or at risk of developing IS (and/or of predicting the risk of developing IS) comprising: a) Contacting a cell sample from the subject with i) an agonist of cluster I or cluster II GiPCR; and ii) Pertussis toxin (PXT); b) Determining the cellular response to Gi protein stimulation; and c) Classifying the subject into a IS functional group according to the subject's cellular response profile.

Subjects can be classified into a specific functional group based on their response curve in the presence of increasing amounts of PTX. For all functional groups (i.e., FG1, FG2 and FG3), the response curve showed a left shift with respect to the control sample (i.e., the IC50 for PTX was smaller than in control samples). This characteristic can be used to identify subjects at risk of developing scoliosis.

Following GiPCR cluster I or cluster II agonist stimulation, the response curve in the presence of PTX is characterized by a first phase in which the response decreases with increasing amounts of PTX followed by a second phase where the response increases with increasing amounts of PTX (V shape curve). In the second phase of the response, the % of response relative to administration of a control vehicle is above that of the corresponding % of response for control (subjects not having IS or not at risk of developing IS), FG2 and FG3 subjects. Hence, a magnitude of cellular response in the presence of high concentration of PTX that is above that of a control (subjects not having IS or not at risk of developing IS as well as FG2 and FG3 subjects) indicates that the subjects belongs to the FG1 functional group.

By "high PTX concentration" is meant a concentration of PXT at which the GiPCR-mediated cellular response is almost completely inhibited by PTX in cells from subjects not having IS or not at risk of developing IS. For example, a high PTX concentration is a concentration at which the % of the GiPCR-mediated response is from from about 0% (i.e., background noise) to 20%, from about 0% to 15% or from about 0% to 10%, preferably below 5% of the corresponding cellular response in the presence of a vehicle (instead of PTX). The high PTX concentration may also be expressed relative to the IC50 value for PTX in control samples. For example, a high PTX concentration in accordance with the present invention is a concentration that is at least 3×, 5×, 6×, 8×, 9×, 10×, 75×, 100×, 150×, 200×, 250×, 500×, 750× or 1000× the concentration of PTX at which 50% of the cellular response is normally inhibited (IC50) in control cells (e.g., cells from subjects not having IS or not at risk of developing IS). In an embodiment, the high PTX concentration is 6× the IC50 concentration. In a particular embodiment, the high PTX concentration is 0.5 ug/ml). As one skilled in the art can appreciate from the results presented herein, the higher the concentration of PTX, the greater the difference in the cellular response between FG1 subjects and control/FG2/FG3 subjects.

In another aspect, the present invention concerns a method of classifying a subject having idiopathic scoliosis IS or at risk of developing IS comprising: a) Contacting a cell sample from the subject with an agonist of a cluster II GiPCR; b) Determining the cellular response to Gi protein stimulation by cellular impedance; and c) Classifying the subject into a IS functional group according to the subject's cellular impedance profile.

Classification into a specific functional group can also be made by looking at the shape of the impedance profile following stimulation with one or more of clusters I, II, III and IV GiPCR agonists relative to control samples. Each GiPCR cluster gives a shape of impedance curve (i.e, an impedance signature) which is different from the other clusters. In addition, among a given GiPCR cluster, controls, FG1, FG2 and FG3 subjects have an impedance profile which is different from the other functional groups and from control, healthy subjects. Unexpectedly and advantageously, following stimulation with cluster II GiPCR agonists, subjects belonging to the FG1 or FG2/FG3 functional groups can be easily classified/identified by the sole shape of their impedance curve in the absence of any control sample. Indeed, GiPCR cluster II agonist stimulation of samples from subjects belonging to the FG1 functional group results in an impedance curve which begins with a negative impedance phase followed by a phase of positive impedance. This negative impedance phase is absent in FG2 and FG3 subjects, thereby allowing to unambiguously identify FG1 subjects.

All classification methods described herein can be used for i) predicting the risk of developing a scoliosis in a subject, ii) for selecting an appropriate preventive measure or treatment iii) for identifying compounds useful in the prevention or treatment of scoliosis or for simply classifying a subject into a specific functional group for clinical trials or other studies in which the effect of a given molecule or treatment may differ between functional groups.

The above described methods may be used alone or in combination and may also be used in addition to at least one other/alternative method of classification and/or method of predicting the risk of developing IS (e.g., method using the $\Delta G$ to classify the subject and/or predict the risk of developing IS). The at least one other method may be used prior to or after using one or more of the above-described methods. In a specific embodiment, the at least one other/alternative method is used prior to using the one or more above-described methods. When the at least one other/alternative method is used prior to using the one or more above-described methods, the above-described methods may advantageously be used (alone or in combination) to classify subjects that had borderline values (i.e. could not be clearly classified into one functional group) by using the other/alternative method (e.g., subjects having a $\Delta G$ of about 10 or about −10 using CDS) into a IS functional group. When the other/alternative method is used after the above-cited one or more methods, it may advantageously be used to classify subjects that had borderline values (i.e. could not be clearly classified into one functional group) by using the above-described method (e.g., subjects having Fe value of about 50% or between about 95 and about 100%) into a IS functional group.

As used herein the terms "borderline subjects" refer to subjects that could not be classified with sufficient confidence (i.e., specificity) into one specific IS functional group using a specific method of classifying IS subjects or where there is a need to simply confirm to which specific functional group a subject belongs.

OPN also has an effect on the cellular response to Gi stimulation in normal cells. In normal cells, OPN will decrease the cellular response to Gi-stimulation through its interaction with integrins (e.g., $\alpha_5\beta_1$). The use of a control sample (e.g., sample from a normal healthy subject) is therefore preferred for identification of at least FG3 subjects based on the above method since these subjects have a Gi cellular response that is closest to normal subjects and a response to Gi-stimulation that is least modified in the presence of OPN. The same observation is made when classifying subjects in accordance with their impedance profile or in the presence of a GiPCR antagonists. When used for predicting the risk of developing a scoliosis in asymptomatic patients, FG3 subjects may thus be difficult to unambiguously identify if no comparison is made with normal subjects. Preferably, a control a sample is used for identification of FG2 and FG3 subjects when predicting the risk of developing a scoliosis.

Hence, in certain embodiments of the above mentioned methods, an additional step of further comparing the results with a control sample (e.g., one or more samples from healthy subject(s) or an equivalent "control value" derived from samples from control subjects) may be useful where, for example, asymptomatic subjects are tested for classifying subjects or predicting the risk of developing scoliosis. This step may however be omitted if an optimal concentration of OPN (i.e., concentration showing no or weak effect on normal cells) has been selected or if only certain functional groups need to be identified (e.g., FG1 and FG2). A control sample (e.g., sample from normal subject) may also not be necessary when the above methods are used as a classification method for borderline subjects in conjunction with (e.g., prior to) an alternative classification methods as explained below. In those cases, the alternative method has already determined with a control that the subject has an IS.

As indicated above, Applicants have discovered that combining one or more methods of the present invention (e.g., the detection of the OPN effect on Gi cellular response) with another classification method allows to more precisely classify subjects having values that are borderline between two functional groups or fall outside the above OPN Fe ranges (e.g., a Fe value of about 50% or between about 95 and about 100%). Any alternative method of classifying a subject into a functional subgroup may be used in accordance with the present invention. For example, confirmation can be performed by classifying the subject into one IS functional group by i) determining the difference ($\Delta G$) or ratio (e.g., Gi/Gs) between cellular responses to Gi and Gs protein stimulations in the cell sample from the subject; ii) determining the magnitude of a cellular response to GiPCR-stimulation in the cell sample relative to a control sample (using GiPCR agonist stimulation and optionally antagonists of Gi-PCR cellular response); iii) determining the phosphorylation states of Gi proteins; or iv) determining the cell (e.g., osteoblasts, chondrocytes, myoblasts) proliferation (described in Moreau et al., 2004; Akoume et al., 2010; Azeddine et al., 2007; Letellier et al., 2008; and WO2003/073102; WO2010/040234 and PCT/CA2014/050562 and U.S. 61/879,314 to Moreau, all incorporated herein by reference).

Preferably, the confirmation is performed by determining the difference between cellular responses to Gi and Gs protein stimulations ($\Delta G$) in the cell sample from the subject. The ΔG is determined by subtracting the average of response magnitude to Gi stimulation (RmGi) from the average of response magnitude to Gs stimulation (RmGs) using the following formula:

$$\Delta G = RmGi - RmGs.$$

According to the ΔG classification, response to Gi stimulation predominates in FG3, while no apparent (i.e., no substantial) imbalance is observed in FG2 subjects. In contrast, FG1 subjects exhibit predominance for response to Gs stimulation. A value of ΔG below −10 is indicative that the subject belongs to IS subgroup FG1; a value of ΔG above −10 and below +10 is indicative that the subject belongs to IS subgroup FG2; and a value of ΔG above +10 is indicative that the subject belongs to IS subgroup FG3.

Alternatively, the difference between Gi and Gs responses may be expressed as a ratio of response to Gi vs. Gs stimulation (Gi/Gs). The FG3 group shows a predominance of response to Gi stimulation (i.e. a Gi/Gs ratio of more than about 1.5), there is no substantial imbalance observed in the FG2 group (i.e. a Gi/Gs ratio of between about 0.5 and 1.5) and the FG1 group exhibits a predominance of response to Gs stimulation (i.e. a Gi/Gs ratio of less than about 0.5).

In the case where classification is resolved by determining the magnitude of a cellular response to Gi stimulation in the cell sample relative to a control sample: i) a cellular response to Gi stimulation lower than the control sample by about 60% (e.g., 60% to 90%) is indicative that the subject belongs to IS subgroup FG1; ii) a cellular response to Gi stimulation lower than the control sample by about 40 to 60% is indicative that the subject belongs to IS subgroup FG2; and iii) a cellular response to Gi stimulation lower than the control sample by less than about (i.e., at most) 40% (or by about 10 to 40%) is indicative that the subject belongs to IS subgroup FG3. The above classification is based on the percentage of degree of reduction relative to control group. Alternatively, the classification can be expressed as the percentage of maximal response relative to the control. In such an embodiment, i) a maximal response below 40% of the control (e.g., between about 10 and 40%) is indicative that the subject belongs to IS subgroup FG1; ii) a maximal response between about 40 and 60% of the control is indicative that the subject belongs to IS subgroup FG2; and iii) a maximal response above about 60% of the control (or between about 60 and 90%) is indicative that the subject belongs to IS subgroup FG3. Because the Gi-mediated defective signaling is due to reduced Gi-protein activity, the magnitude of a cellular response to Gi-stimulation for each endophenotype (i.e., FG1, FG2 and FG3 subgroups) can also be assessed by determining (e.g., measuring) the effect of a GPCR antagonist (e.g., GP Ant-2 or PTX) or GiPCR activator (e.g., mastoparan-7). For example, inhibition curves of GPCR antagonist GP Ant-2 on response to various selective agonists of Gi-coupled receptors (from clusters i to iv) give relative inhibition profiles (e.g., IC50 FG1>IC50 FG2>IC50 FG3) which reflect the magnitude of Gi-mediated response relative to control observed for agonist stimulation. GiPCR activator Mastoparan-7 produces Gi protein-response profiles in control and IS (FG1, FG2 and FG3) groups similar to that observed for any other Gi-protein agonists with similar degree (%) of Gi-mediated response relative to the control group. The magnitude of a cellular response to Gi stimulation (as measured following Gi-stimulation and/or inhibition) can be determined by various methods including but not limited to determination of impedance (e.g., CDS), Time-Resolved fluorescence (TRF), Time-Resolved-Florescence Resonance Energy Transfer (TR-FRET), Enzyme Fragment complementation (EFC), melanophore phenotype and optical biosensor.

In certain subjects, scoliosis develops rapidly over a short period of time to the point of requiring a corrective surgery (often when the deformity reaches a Cobb's angle ≥45°). Current courses of action available from the moment a scoliosis such as IS is diagnosed (when scoliosis is apparent) include observation (including periodic x-rays, when Cobb's angle is around 10-25°), orthopedic devices (such as bracing, when Cobb's angle is around 25-30°), and surgery (Cobb's angle over 45°). Thus, a more reliable determination of the risk of progression (through better classification) could enable to 1) select an appropriate diet to remove certain food products identified as contributors to scoliosis in certain subjects (e.g., Hyaluronic acid (HA) for FG1 and FG2 subjects); 2) select the best therapeutic agent o treatment or preventive measure (an inhibitor of OPN expression or activity (e.g., neutralizing antibody specific to OPN, sCD44 or RGD peptide or derivative thereof, long term brace treatment which reduce OPN level, melatonin, selenium, PROTANDIM) in the case of FG2 and FG3 subjects or a stimulator of OPN expression or activity in the case of FG1 subjects (e.g., HA supplements or HA-rich diet, antibody against CD44 etc.); 3) select the least invasive available treatment such as postural exercises (e.g., massages (e.g., 30-90 minutes pulsative compressive pressure applied locally) or low intensity pulsed ultrasound (LIPUS) which increase OPN level for FG1 subjects, orthopedic device (brace) or other treatment or preventive measure (e.g., accupoint heat sensitive moxibustion, heat therapy with pad, thermal bath, electroacupuncture) which decrease OPN level, for FG2 and FG3 subjects, or less invasive surgeries or surgeries without fusions (a surgery that does not fuse vertebra and preserves column mobility) and/or 4) the best follow-up schedule (e.g., increasing or decreasing the number of follow-up visit to the doctor during for example a 3, 6 or 12 month period or increasing or decreasing the number of x-rays during for example a 3, 6 or 12 month period).

Applicants have determined that subjects classified in the FG2 functional group are more at risk of developing severe scoliosis (i.e., a scoliosis which will require corrective surgery or which will progress more rapidly). Furthermore as disclosed herein and in copending U.S. 61/879,314, OPN, which is an important factor in scoliosis progression and development, has opposite effects in FG1 subjects as compared to FG2 and FG3 subjects. Applicant's have found that OPN has a protective effect in FG1 subjects by increasing the Gi-mediated cellular response in these subjects (i.e. OPN is able to help compensate the Gi signalling defect present in scoliosis subjects or subject at risk of developing scoliosis). Conversely, FG2 and FG3 subjects are sensitive to OPN i.e., that OPN further reduces the Gi-mediated response in these subjects and thereby further contributes (enhance) scoliosis development and progression. OPN's effect is more pronounced in FG2 subjects, which are qualified as being "hypersensitive to OPN.

The present inventors have also previously established that OPN's inhibitory action on Gi-mediated cell signalling is due (at least partly) to its interaction with integrins (e.g., $\alpha_5\beta_1$). This interaction can be modulated by the presence of CD44, another OPN receptor. A mutation in CD44 (CT mutation) has been shown to further increase the sensitivity of scoliotic subjects to the damaging effects of OPN (see PCT/CA2014/050569, to Moreau). CD44 (e.g., soluble CD44) can compete with integrins for OPN binding and therefore indirectly regulate OPN's effect on Gi-mediated cell signaling. Furthermore, PIPK1γ activity increases the affinity of integrins for OPN through FAK and Src. In turn, PIP1Kγ activity is regulated by PTPµ. PIPK1γ has been shown to be upregulated while PTPµ has been shown to be downregulated in cells from IS subjects (see PCT/CA2014/050568 to Moreau).

Accordingly, the present invention provides a method of predicting the risk of developing severe IS comprising determining the effect of OPN on the cellular response to GiPCR stimulation by comparing the cellular response obtained in the presence of OPN with the cellular response obtained in the absence of OPN and classifying the subject into one IS functional, wherein classification into the FG2 functional group is indicative that the subject is at risk of developing severe IS. Corresponding methods of predicting the risk of developing scoliosis are provided based on i) the impedance signature in response to Gi protein stimulation (e.g., cluster II receptor agonists) and ii) the cellular response to Gi protein stimulation in the presence of PTX. The present invention also encompasses selecting the most efficient and least invasive known preventive action, treatment or follow-up schedule in view of the determined classification and risk of developing scoliosis.

Accordingly, the present invention provides a method of selecting a preventive action, treatment or follow-up schedule for a subject suffering from IS comprising classifying the subject using at least one of the above described classification methods.

As discussed above, in the FG1 subgroup, OPN has a protective effect on scoliosis development and progression. Accordingly, in these subjects it is desirable to increase OPN level or bioavailability rather than to decrease it. Preventive and treatment measures in FG1 subjects should thus aim at increasing OPN level or activity. Conversely, FG2 and FG3 subjects are particularly sensitive to OPN. In these subjects high OPN levels are undesirable and can increase the risk of scoliosis development. Preventive and treatment measures in FG2 and FG3 subjects should thus aim at decreasing OPN level or activity.

Hyaluronic Acid (HA) is known to compete with OPN for binding to CD44 (another OPN receptor) and thus to increase the level of OPN available to bind to integrins. Accordingly, one way of increasing OPN's activity (e.g., binding to integrins) is by increasing the amount of HA in the subject which in turn increases OPN bioavailability. This can be done for example by taking HA supplements or by increasing HA intake or HA synthesis by favoring certain food. Non-limiting examples of food with high HA content or which stimulates/support HA production include, meat and meat organs (e.g., veal, lamb, beef and gizzards, livers, hearts and kidneys), fish, poultry (including meat fish and poultry broths), soy (including soy milk), root vegetables containing starch including potatoes and sweet potatoes, satoimo (Japanese sweet potato), imoji (Japanese sweet potato), Konyaku concoction (root vegetable concoction. Fruits and vegetables rich in vitamin C, magnesium or zinc are also useful as they support the synthesis of HA by the body. Non-limiting examples of food rich in vitamin C include lemons, oranges, limes, grapefruit, guava, mango, cherries, kiwi, blueberries, raspberries, all varieties of grapes, parsley and thyme. Fruits and vegetables rich in magnesium include apples, bananas, tomatoes, avocados, pineapples, melons, peaches, pears, spinach, cauliflower, broccoli, asparagus, green lettuce, Brussels sprouts and green beans. Non-limiting examples of food rich in zinc include pumpkins, yeast, peanuts, whole grains, beans, and brown rice.

Conversely, FG2 and FG3 subjects should decrease or maintain lower levels of HA and therefore should comply with a HA-poor diet (by avoiding one or more of the above food).

Other non-limiting examples of treatment or preventive measures which increase OPN expression (e.g., circulating OPN levels) or activity and which may be beneficial to FG1 subjects include low intensity pulsed ultrasound (LIPUS) and the application of massages/pulsative compressive pressure as described in U.S. Ser. No. 13/822,982.

Other non-limiting examples of treatment or preventive measures which decrease OPN expression (e.g., circulating OPN levels) or activity and which may be beneficial to FG2 and/or FG3 subjects include accupoint heat sensitive moxibustion, heat therapies with pad, thermal bath, electroacupuncture, melatonin, selenium (as supplements or by complying to a selenium-rich diet), PROTANDIM (nutraceutic cocktail known to reduce plasma or serum OPN levels and used as a natural anti-oxydant mix), etc, which have been shown to decrease OPN levels.

Other ways to increase or decrease the level or activity OPN include the examples provided in Table 1, below.

TABLE 1

Non-limiting examples of treatment and preventive measures according to the functional endophenotype.

| Treatment or preventive measure | Functional group | | | Comments |
| --- | --- | --- | --- | --- |
| | FG1 | FG2 | FG3 | |
| Increase in OPN level or activity | yes | no | no | OPN has a protective effect in FG1 subjects but constitute a risk factor in FG2 and FG3 subjects. |
| Increase in sCD44 level | no | yes | yes | Decreases OPN's bioavailability to integrins |
| Incease HA level | yes | avoid | avoid | HA increases OPN's bioavailability |
| Decrease HA level | avoid | yes | yes | HA increases OPN's bioavailability |
| Brace treatment | Avoid or close monitoring of OPN level required. | yes | yes | Long term brace treatment decreases OPN level (see U.S. 61/879,314) |
| Massages (e.g., pulsative compressive pressure) | yes | avoid | avoid | Increase OPN level (see U.S. 13/822,982) |
| Src inhibitors | — | yes | yes | Involved in the activation of PIPK1γ |
| FAK inhibitors | — | yes | yes | Involved in the activation of PIPK1γ |
| RGD peptides | — | yes | yes | Inhibit the binding of OPN to integrins |
| Decreasing PIPK1γ level or activity (e.g., inhibitors) | — | yes | yes | Increases bniding of integrins to OPN |
| Increasing the level or activity of PTPµ | — | yes | yes | Involves in the dephosphorylation (inhibition) of PIPK1γ |

TABLE 1-continued

Non-limiting examples of treatment and preventive
measures according to the functional endophenotype.

| Treatment or preventive measure | Functional group | | | Comments |
|---|---|---|---|---|
| | FG1 | FG2 | FG3 | |
| Early corrective surgery (before 45 degree Cobb angle) | no | yes | no | FG2 subjects have an increased risk of severe scoliosis (assessment of sCD44 levels, OPN levels and presence of mutation in CD44 which decreases affinity toward OPN are also important in making decision) |

In an embodiment, when the subject is classified as belonging to the FG2 functional group the subject is prescribed corrective surgery prior to reaching a 45 degree scoliosis (e.g., prior to reaching 30, 32, 34, 36, 38, 40, 41, 42, 43, 44 degree scoliosis); and wherein when the subject belongs to the FG1 or FG2 functional group, the subject has a decreased risk of curve progression over a 45° angle and the subject is prescribed fewer than 22 radiological examinations within the next 3 years following classification.

The present invention also encompasses kits for classifying subjects having IS or at risk of developing IS; kits for predicting the risk of developing IS and kits for predicting the risk of developing severe IS. Such kits may comprise 1. (a) recombinant OPN (rOPN); (b) one or more ligands (e.g., agonists) for stimulating GiPCRs (e.g., Cluster I, II, III or iv ligands (e.g., agonists), Mastoparan, etc.); or 2. a) PTX; b) one or more ligands for stimulating GiPCRs (e.g., Cluster I, II, III or IV ligands (e.g., agonists). Optionally the kits may comprise (c) i) one or more ligands for stimulating GsPCRs; ii) one or more ligands for inhibiting GiPCR (e.g., antagonists, GP Ant-2) and/or (ii) one or more antibody for detecting Giα phosphorylation, together with instructions for using the kit.

Definitions

For clarity, definitions of the following terms in the context of the present invention are provided.

As used herein the terms "at risk of developing a scoliosis" or "at risk of developing IS" refer to a genetic or metabolic predisposition of a subject to develop a scoliosis (i.e. spinal deformity) and/or a more severe scoliosis at a future time (i.e., curve progression of the spine). For instance, an increase of the Cobb's angle of a subject (e.g., from 40° to 50° or from 18° to 25°) is a "development" of a scoliosis. The terminology "a subject at risk of developing a scoliosis" includes asymptomatic subjects which are more likely than the general population to suffer in a future time of a scoliosis such as subjects (e.g., children) having at least one parent, sibling or family member suffering from a scoliosis. Among others, age (adolescence), gender and other family antecedent are factors that are known to contribute to the risk of developing a scoliosis and are used to evaluate the risk of developing a scoliosis. Also included in the terminology "a subject at risk of developing a scoliosis" are subjects already diagnosed with IS but which are at risk to develop a more severe scoliosis (i.e. curve progression).

As used herein, the terms "severe scoliosis", "severe IS" or "severe progression" is an increase of the Cobb's angle to 45° or more, potentially at a younger age.

As used herein the term "subject" is meant to refer to any mammal including human, mouse, rat, dog, chicken, cat, pig, monkey, horse, etc. In a particular embodiment, it refers to a human.

As used herein the term "treating" or "treatment" in reference to scoliosis is meant to refer to at least one of a reduction of Cobb's angle in a preexisting spinal deformity, improvement of column mobility, preservation/maintenance of column mobility, improvement of equilibrium and balance in a specific plan; maintenance/preservation of equilibrium and balance in a specific plan; improvement of functionality in a specific plan, preservation/maintenance of functionality in a specific plan, cosmetic improvement, and combination of any of the above.

As used herein the term "preventing" or "prevention" in reference to scoliosis is meant to refer to a at least one of a reduction in the progression of a Cobb's angle in a patient having a scoliosis or in an asymptomatic patient, a complete prevention of apparition of a spinal deformity, including changes affecting the rib cage and pelvis in 3D, or a combination of any of the above.

As used herein the terms "follow-up schedule" is meant to refer to future medical visits a subject diagnosed with a scoliosis or at risk of developing a scoliosis is prescribed once the diagnosis or risk evaluation is made. For example, when a subject is identified as being at risk of developing a severe scoliosis or at risk of rapid curve progression (e.g., a subject classified as belonging to the FG2 subgroup in accordance with the present invention), the number of medical visits (e.g., to the orthopedist) is increased and/or the number of x-rays in a given period (e.g., 3, 6 or 12 months) is increased. On the other hand, when a subject is identified as having a lower risk of curve progression or rapid curve progression (e.g., subject being classified as belonging to the F1 or FG3 subgroup) the number of medical visits or x-rays may be decreased to less than the average (e.g., less than 22 x-rays over a 3 year period or less than 1 visit every 3 months, 6 months or 12 months).

As used herein, the terminology "blood sample" is meant to refer to blood, plasma or serum.

As used herein, the terminology "cell sample" is meant to refer to a sample containing cells expressing the desired GPCR(s) in sufficient amount to detect a cellular response in accordance with the present invention. The cells in the cell sample may be any type of cells as long as they express the desired GPCR to be tested. The cells used herein naturally express one or more receptors coupled to $G_i$ proteins and were selected in part for their accessibility for collection from subjects. Hence, cells such as osteoblasts, osteoclasts, peripheral blood mononuclear cell (PBMC) (inherently including principally lymphocytes but also monocytes) and myoblasts are advantageously accessible and may conveniently be used in the methods of the present invention. Blood cells (e.g., PBMCs, platelets (thrombocytes), etc.) in particular are particularly accessible and provide for a more rapid testing. Any blood cell can be used for the methods of the present invention so long as it possesses at least one GPCR receptor coupled to a Gi protein. The cells can be fresh or frozen and may or may not have been cultured (expanded) prior to testing. The "sample" may be of any origin including blood, saliva, tears, sputum, urine, feces, biopsy (e.g., muscle biopsy), as long as it contains cells expressing the desired GPCR(s).

The methods of the invention may be performed using cell expressing one or more receptor(s) coupled to a $G_i$ and/or Gs proteins. "Receptor" as used herein refers to wild-type receptors as well as to fragments and/or variants thereof that retains the activity (i.e. GPCR-mediated activity) of the wild-type receptors. FIG. 8 presents a non-exhaustive list of GiPCRs suitable for use in the method of the present invention.

As used herein the terminology "control sample" is meant to refer to a sample from which it is possible to make a comparison and to classify/stratify subjects into a specific functional group. In an embodiment, a "control sample" is a sample that does not originate from a subject known to have scoliosis or known to be a likely candidate for developing a scoliosis (e.g., idiopathic scoliosis (e.g., Infantile Idiopathic Scoliosis, Juvenile Idiopathic Scoliosis or Adolescent Idiopathic Scoliosis (AIS))). In another embodiment, the control sample is from one or more subjects of the group FG1, FG2 or FG3. In the context of the present invention, "a control sample" also includes a "control value" or "reference signal" derived from one or more control samples from one or more subjects. In methods for predicting the risk of developing scoliosis in a subject that is pre-diagnosed with scoliosis, the sample may also come from the subject under scrutiny at an earlier stage of the disease or disorder. In an embodiment, the control sample is a cell of the same type (e.g., both the test sample and the reference sample(s) are e.g., lymphocytes, osteoblasts, myoblasts or chondrocytes) as that from the subject. Of course multiple control samples derived from different categories of subjects (e.g., FG1, FG2, FG3 and healthy subjects) can be used in the methods of the present invention. As used herein, the term "reference signal" or "control value" is meant to refer to a signal (e.g., fluorescence, impedance, cAMP concentration or any other measurable signal) that serves as a reference in predicting the risk of developing scoliosis or in establishing classification of a subject into a particular functional group. A reference signal can be obtained by using one or more samples from suitable control subjects (subjects not having a scoliosis or not at risk of developing a scoliosis, FG1, FG2 or FG3 subjects depending on the method). The reference signal may originate from a single control subject ((i.e., a normal healthy subject or a subject already classified in a given endophenotype group) or may be derived from a group of control subjects (i.e., equivalent to the average response in control subjects).

"GPCRs" or "G protein-coupled receptors" constitute a large protein family of receptors that sense molecules outside the cell and activate inside signal transduction pathways leading to various cellular responses.

The G protein-coupled receptor is activated by an external signal in the form of a ligand (e.g., agonists). This creates a conformational change in the receptor, causing activation of a G protein. Further effect depends on the type of G protein. Four types of G proteins exists: Gαs (Gs), Gαi/o (Gi), Gαq/11, and Gα12/13. Gαs (Gs) is a heterotrimeric G protein subunit that activates the cAMP-dependent pathway by activating adelylate cyclase. Gαi/o (Gi) is a heterotrimeric G protein subunit that inhibits the cAMP-dependent pathway by inhibiting adelylate cyclase. As supported herein by the identification of four difference GiPCR receptor cluster, G protein-coupled receptors are not necessarily exclusively coupled to a particular type of G protein (e.g., Gi or Gs) but may interact with other G proteins (e.g., Gi or Gs) depending on the conditions.

The ligands (e.g., agonists and antagonists) that bind and activate (inhibit) these receptors include light-sensitive compounds, odors, pheromones, hormones, and neurotransmitters, and vary in size from small molecules to peptides to large proteins. As used herein, the term "ligand" includes any molecule (synthetic or natural) capable of binding to GPCR to modulate (increase or decrease) its cellular response. Accordingly, the term "ligand" in the expression "GiPCR ligand" or "GsPCR ligand" includes agonists of GiPCR, agonists of GsPCR, antagonists of GiPCR and antagonists of GsPCR. Any molecule can be used in accordance to the present invention as long as it allows measuring the magnitude of the cellular responses involving Gi or GsPCR.

There are two principal signal transduction pathways involving the G protein-coupled receptors: the cAMP signal pathway and the phosphatidylinositol signal pathway. When a ligand binds to the GPCR it causes a conformational change in the GPCR, which allows it to act as a guanine nucleotide exchange factor (GEF). The GPCR can then activate an associated G-protein by exchanging its bound GDP for a GTP. The G-protein's a subunit, together with the bound GTP, can then dissociate from the β and γ subunits to further affect intracellular signaling proteins or target functional proteins directly depending on the α subunit type.

The effector of both the Gs and Gi pathways is the cyclic-adenosine monophosphate (cAMP) generating enzyme adenylate cyclase, or AC. AC catalyzes the conversion of cytosolic adenosine triphosphate (ATP) to cAMP, and all are directly stimulated by G-proteins of the Gs class. Conversely, interaction with Gα subunits of the Gi type inhibits AC from generating cAMP. Thus, a GPCR coupled to Gαs counteracts the actions of a GPCR coupled to Gαi/o, and vice versa. The level of cytosolic cAMP may then determine the activity of various ion channels as well as members of the ser/thr specific protein kinase A (PKA) family. Thus cAMP is considered a second messenger and PKA a secondary effector.

Accordingly, as used herein the term "GiPCR" refers to a GPCR preferably (i.e., mainly) coupled to the Gαi proteins (e.g., Gαi1, Gαi2 and Gαi3) which when stimulated by a ligand (i.e., an agonist to the GiPCR receptor) inhibits (reduces) the production of cAMP in a cell. The methods of the present invention may be performed by stimulating any GiPCR and more than one GiPCR at the same time (1, 2, 3, 4 GiPCRs). GPCRs coupled to the $G_i$ protein include, for example, CD47, serotonin receptors (5-HT), adenosine receptors, adrenergic receptors, cannabinoid receptors, histamine receptors, prostaglandin receptors and dopamine receptors. Non-limiting examples of GiPCRs suitable for use in the method of the present invention are presented in FIG. 8. Furthermore, any ligand of a given GiPCR may be used in accordance with the present invention as long as it leads to the activation of the Gi protein and reduction of cellular cAMP. Multiple ligands (agonists and antagonists) may also be used in accordance with the present invention. Ligands (e.g., synthetic or natural) of GiPCRs are well known in the art and several of these ligands are commercially available. FIG. 9 presents a non-exhaustive list of GiPCR ligands suitable for use in the method of the present invention. In an embodiment, the above-mentioned receptor coupled to a $G_i$ protein is a melatonin receptor, a serotonin receptor, a somatostatin receptor, an Apelin receptor, a dopaminergic receptor, a lysophosphatidic acid receptor, a formyl peptide receptor, an α-adrenergic receptor, an adenosine receptor, a cannabinoid receptor or any combination thereof. In a further embodiment, the above-mentioned receptor is LPAR, A1R, MT2R, 5-HT1AR, α2-ADR, A3R, OR, D2R, SSTR, APJ, FPR2 or CB2.

In a specific embodiment, the above-mentioned ligand is a known agonist of the receptor. In an embodiment, the above-mentioned ligand is (a) melatonin for the MT2 receptor, (b) 1-[3-(3,4-Methylenedioxyphenoxy)propyl]-4-phenyl-piperazine maleate (known as BP554 maleate) for the 5-HT1A receptor, (c) 5-bromo-N-(4,5-dihydro-1H-imidazol-2-yl)-6-quinoxalinamine (known as UK14304) for the α2-AD receptor; (d) 1-Deoxy-1-[6-[[(3-iodophenyl)methyl]amino]-9H-purin-9-yl]-N-methyl-β-D-ribofuranuronamide (known as IB-MECA) for the A3 receptor; Lysophosphatidic acid (known as LPA) for the LPA receptor; (2S)-2-[[2-[[(2R)-2-[[(2S)-2-amino-3-(4-hydroxyphenyl)propanoyl]amino]propanoyl]amino]acetyl]-methylamino]-N-(2-hydroxyethyl)-3-phenylpropanamide (known as DMAGO) for the mu-opioid receptor, 1-(6-Amino-9H-purin-9-yl)-1-deoxy-N-ethyl-β-D-ribofuranuronamide (known as NECA) for the adenosine receptors (e.g., A1, A2a and A3); somatostatin for the SSTR receptor; peptide MMK-1 (LESIFRSLLFRVM) for the FPR2 receptor; Apelin-17 for the APJR receptor; (4aR,8aR)-5-propyl-4,4a,5,6,7,8,8a,9-octahydro-1H-pyrazolo[3,4-g]quinolone (known as quinpirole) for the D2 and D3 receptors and/or (e) N-Cyclohexyl-7-chloro-1-[2-(4-morpholinyl)ethyl]quinolin-4(1H)-one-3-carboxamide (known as CB65) for the CB2 receptor.

Similarly, as used herein the term "GsPCR" refers to a GPCR preferably (i.e., mainly) coupled to the Gαs protein which when stimulated by a ligand (i.e., an agonist to the GsPCR receptor) leads to the activation of the cAMP-dependent pathway thereby increasing the level of cAMP in a cell. When assessing an imbalance between Gi and Gs cellular responses in accordance with the methods of the present invention the activity (cellular response) of any GsPCR may assessed. Also the activity (cellular response) of more than one GsPCR may be assessed at the same time (1, 2, 3, 4 GsPCRs). Non-limiting examples of GsPCRs that can be used in accordance with the present invention include receptors types 5-HT4 and 5-HT7, ACTH receptor, Adenosine receptor types A2a and A2b, Arginine vasopressin receptor 2, β-adrenergic receptors types β1, β2 and β3, Calcitonin receptor, Calcitonin gene-related peptide receptor, corticotropin-releasing hormone receptor, Dopamine receptors D1-like family (D1 and D5), FSH-receptor, Gastric inhibitory polypeptide receptor, Glucagon receptor, Histamine H2 receptor, Luteinizing hormone/choriogonadotropin receptor, melanocortin receptor: MC1R, MC2R (aka ACTH receptor), MC3R, MC4R, MC5R, Parathyroid hormone receptor 1, Prostaglandin receptor types D2 and I2, secretin receptor and thyrotropin receptor. Furthermore, any ligand of a given GsPCR may be used in accordance with the present invention as long as it leads to the activation of the Gs protein and production of cAMP. Of course, the effect of antagonists to GsPCR may also alternatively be used to determine the magnitude of the cellular response to GsPCR stimulation and the use of antagonists is within the scope of the present invention. For example IC50 could be calculated to assess magnitude of GsPCR response within a cell. Antagonists to GsPCR are well-known and the skilled practitioner knows how to assess the magnitude of response to GsPCR response in the presence of antagonists. Multiple ligands (agonists and antagonists) for GsPCR may also be used in accordance with the present invention. Ligands (e.g., synthetic or natural) of GsPCRs are well known in the art and several of these ligands are commercially available.

As used herein, the expression "cellular response" in "determining the cellular response to Gi/Gs stimulation" for example is meant to refer to any detectable cellular response/reaction due to Gi or GsPCR stimulation and/or inhibition (agonist/antagonist ligand binding). For example, any cellular response linked to the activation/inhibition of the cAMP-dependent pathway may be used to assess Gi/GsPCR cellular response in accordance with the present invention. Cellular response to Gi/GsPCR stimulation include but is not limited to cAMP inhibition/activation; Gi and/or Gs proteins phosphorylation pattern and/or levels, kinases phosphorylation pattern and/or levels (PKA, PKC, CAMK1, CK, CAMK2), cellular proliferation levels, changes in protein-protein interactions and cellular impedance modifications (detected by cellular dielectric spectroscopy (CDS)). All of these cellular responses can be assessed following Gi or Gs-PCR stimulation with any agonists in the presence or absence of antagonists as long as it allows to determine the relative level of GiPCR and/or GsPCR cellular response in order to distinguish between the three endophenotypes (FG1, FG2 and FG3). For example, as disclosed herein, the magnitude of GiPCR response can be assessed and the endophenotypes distinguished based on their relative cellular response in the presence of GP Ant-2 or PTX, which both inhibit GPCRs. FIG. 15 provides examples of cellular responses expected when stimulating GiPCRs in the presence and absence of OPN.

"GiPCR/GsPCR stimulation" or "Gi/Gs stimulation" refers to GiPCR or GsPCR activation (ligand binding) leading to a cAMP-dependent cellular response. As noted above Gi/Gs stimulation is achieved by contacting a cell expressing a given GiPCR/GsPCR with its cognate ligand(s).

The changes in the magnitude of the signal induced by the ligand (i.e., changes in cellular response(s) induced by e.g. an agonist or antagonist) may be detected using any suitable methods. Methods for measuring the magnitude or intensity of the signal (e.g., intracellular response) mediated through GiPCRs are well known in the art. The magnitude of the signal may be determined, for example, by measuring the level of a molecule, such as a second messenger (e.g., cAMP, $Ca^{2+}$) or a gene product (e.g., mRNA or protein) whose level is modulated following triggering of the receptor by a ligand. The magnitude of the signal may also be determined, for example, by measuring changes in protein-protein interactions (e.g., by fluorescence resonance energy transfer (FRET); Time Resolved (TR)-FRET or bioluminescence resonance energy transfer (TR-BRET)) following triggering of the receptor by a ligand. Other methods to measure the magnitude or intensity of the signal mediated through GiPCRs include, for example, measurement of cAMP levels (Medhurst et al., 2003. In: J Neurochem., 84), measurement of thallium flux using GIRK-thallium Flux Assay (Niswender et al., 2008; In: Mol Pharmacol. 73(4)), Patch-clamp (Saugstad et al., 1996. In: J. Neurosci. 16), measurement of GTPγS binding using [$^{35}$S] GTPγS labelling assay (Riobo et al., 2006. In: Proc Natl Acad Sci USA, 103), and measurement of the changes in impedance (Peters et al., 2007. In: J Biomol. Screen. 12: 312-9). Other non-limiting examples of suitable methods include Enzyme Fragment Complementation (EFC), Time Resolved Florescence (TRF), melanophore phenotype and optical biosensor. In an embodiment, the change in magnitude of the signal is determined using the changes in impedance that occurs in the cell following receptor triggering (e.g., cellular dielectric spectroscopy (CDS)). Such measurement may be made, for example, using the real-time cell electronic sensing (RT-CES™) technology (ACEA Biosciences Inc., San Diego, Calif., USA) (Huang et al., Analyst, 2008, 133(5): 643-648; Solly et al., Assay Drug Dev. Technol., 2004, 2(4): 363-372) or using the CellKey™ technology (MDS Sciex, Concord, Ontario, Canada) according to the method described below. In a preferred embodiment, the magnitude of a cellular response to Gi or Gs stimulation is determined by (TR)-FRET, EFC, TRF, melanophore phenotype, optical biosensor or CDS.

In an embodiment, a lower or higher signal refers to a difference of at least about 5%, or 10%, in further embodiments at least about 15%, 20%, 25%, 30%, 35%, 40%, 45%, 50%, 55%, 60%, 65%, 70% 75%, 80%, 85%, 90%, 95% 100%, 120%, 130%, 140%, 150%, 160%, 170%, 180%, 190% or 200% between the signal obtained with the test sample (sample obtained from the subject being tested) relative to the reference (control) signal. In an embodiment, a substantially identical signal refers to a signal that differs by less than 10%, in further embodiments by less than 9%, 8%, 7%, 6% or 5%, as compared to the reference signal.

In an embodiment, the methods are performed in a format suitable for high throughput assays, e.g., 96- or 384-well format, and suitable robots, (e.g., pipetting robots), and instrumentation may be used. In an embodiment, the assay will be assayed in plates (e.g., 96-wells, 384-wells, etc.) containing the test sample and one or more samples.

As used herein, the terminology "fold effect" or "Fe", when used in the context of the present invention refers to the effect of OPN on the magnitude of the Gi-mediated cellular response. The fold effect (Fe) of OPN on Gi-mediated response is calculated by dividing the average of response magnitude to Gi stimulation in presence of OPN (RmGiOPN) with the average of response magnitude to Gi stimulation in the absence of OPN (RmGi) using the following formula:

Fe=100×(RmGiOPN/RmGi).

The articles "a," "an" and "the" are used herein to refer to one or more than one (i.e., to at least one) of the grammatical object of the article.

The term "including" and "comprising" are used herein to mean, and are used interchangeably with, the phrases "including but not limited to" and "comprising but not limited to".

The terms "such as" are used herein to mean, and is used interchangeably with, the phrase "such as but not limited to".

The present invention is illustrated in further details by the following non-limiting examples.

The classification protocols described below details embodiments of the experimental and analytical procedure for a cell-based assay developed in Applicants' laboratory as a functional test to predict the risk of developing idiopathic scoliosis in asymptomatic and IS subjects (e.g., AIS). In a first aspect of the present invention, the assay comprises the evaluation of the functional status (relative cellular response) of Gi and Gs proteins in cells (e.g., peripheral blood mononuclear cells (PBMCs)) by e.g., changes in impedance (e.g., cellular dielectric spectroscopy (CDS) assessed using e.g., CellKey™ apparatus) and in the classification of children into functional groups (FG1, FG2, FG3) with respect to the difference between the degree of response to Gi and Gs proteins stimulation (ΔG). Of course any other suitable methods of assessing Gi and Gs cellular response (e.g., TR-FRET; EFC, TRF, melanophore phenotype and optical biosensor) can be used in accordance with the present methods. The classification is further confirmed by the determination of the effect of osteopontin (OPN) on the subject's cellular response to Gi stimulation.

In accordance with the technique followed in Examples 1 and 2 below, approximately a volume of 10 mL of blood is required to extract PBMCs by Ficoll-gradient and cells are then stored in liquid nitrogen. The optimal number of PBMCs (about $1.5 \times 10^5$ cells or more) to perform the assay is obtained after about two days of cell culture. Essentially, cells are first incubated with phytohemmaglutinin (PHA). After 24 h incubation, the medium is replaced by a PHA-free culture medium for an additional 24 h prior to cell seeding and OPN treatment. Cells are then spectroscopically screened for their response to somatostatin and isoproterenol which activate Gi and Gs proteins, respectively, through their cognate receptors. Both somatostatin and isoproterenol are simultaneously injected with an integrated fluidics system and the cells' responses are monitored for 15 min.

The assay can be performed with fresh or frozen PBMCs (conserved frozen for up to one year) and the procedure is completed within 4 days. Since using freshly isolated PBMCs may be cumbersome when testing large number of individuals, frozen PBMCs may optimally be used and offer a more practical alternative in clinical setting. In addition, the use of frozen PBMCs allows simultaneous analysis, within a single assay run, of PBMCs samples from multiple time points during a longitudinal study. To maximize assay reproducibility, Applicants recommend avoiding freeze-thaw cycle and using the frozen sample only once. The procedure is very simple, allowing for accurate detection of defective Gi protein function in a short time. Using this procedure, asymptomatic and scoliotic children can be easily classified to better predict their clinical outcome without any danger for their health. However, when performing classification according to the degree of maximum response to Gi stimulation relative to the healthy control subjects[12], the fact that these control subjects should, not only match with age and gender of scoliotic or asymptomatic children, but also not be on any medication, may constitute an important obstacle for the recruitment of control subjects. Therefore, performing classification by examining the degree of imbalance between response to Gi and Gs protein stimulation (i.e. average of response magnitude to Gi stimulation (RmGi) minus the average of response magnitude to Gs stimulation (RmGs)) in the same individual is ideal to eliminate the necessity of using control subjects.

The use of the CDS-based system to perform this prognostic test advantageously simultaneously provides Gi- and Gs-mediated cellular response in the same assay.

Figure 4:
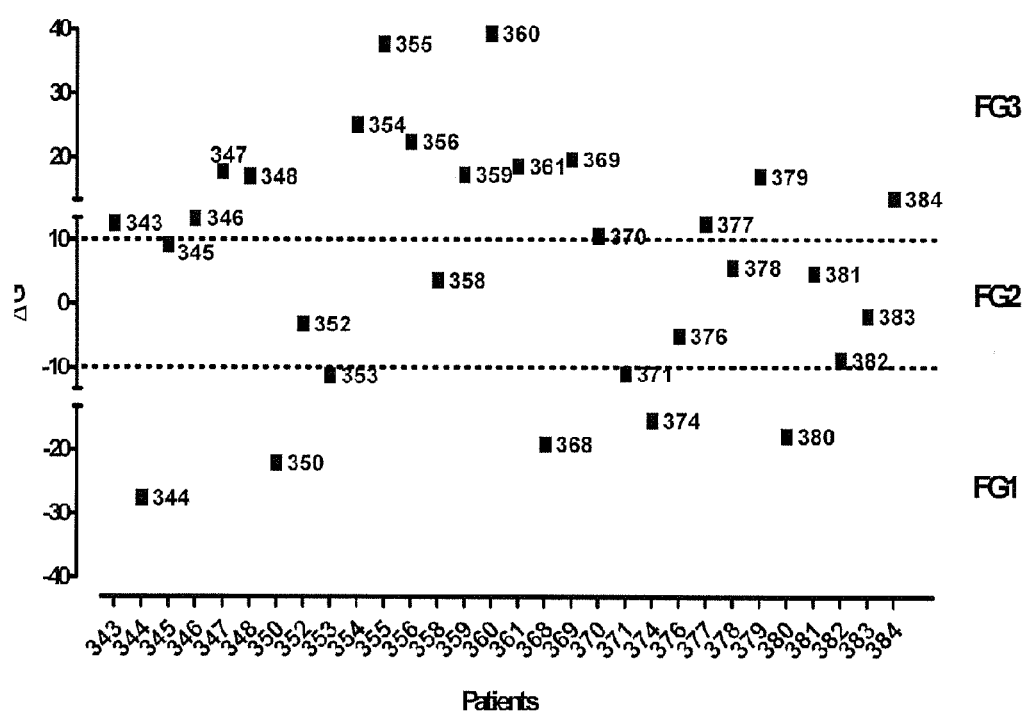
FIG. 4 illustrates the ΔG functional classification. The graph illustrates the difference between responses to Gi and Gs (i.e. ΔG) stimulation obtained in PBMCs from patients with IS. Values were measured by the CDS-based system in response to 10 µM of Somatostatin and isoproterenol. Each point represents the ΔG of both responses in duplicate.

Certain patients will exhibit borderline values in the ΔG CDS-based assay (or other classification methods based on e.g., Gi cellular response detection) making them difficult to classify, as illustrated by results presented in FIG. 4. Applicants have discovered that OPN induces a Gi-mediated cellular response that varies between the three functional groups. Applicants have found that in the presence of OPN, the response to Gi stimulation increases in functional FG1, while it decreases in FG2, and, to a lesser extent, in FG3.

The present invention is illustrated in further, details by the following non-limiting examples.

Example 1

Materials and Methods

Reagents and equipment. Table 2 presents the reagents, equipment and their sources used in an embodiment of the method of the present invention.

TABLE 2

| Name | Company | Catalog Number | Comments |
|---|---|---|---|
| RPMI | Wisent Inc | 350-005-CL | |
| FBS | Therno Scientific Hyclone | SH3007103 | |
| DMSO | Sigma Aldrich | D2650 | |
| Ficoll-Plaque | GE Healthcare | 17144003 | |
| Antibiotic-Antimycotic | Invitrogen | 15240-062 | |
| Phytohemagglutinin (PHA) | Invitrogen (Gibco) | 10576-015 | |
| Recombinant Human Osteopontin | R & D Systems, Inc | 1433-OP/CF | |
| Somatostatin | Tocris | 1157 | |
| Isoproterenol | Tocris | 1743 | |
| PBS | Wisent Inc | 311-010-CL | |
| Sterile pipette tips | Axygen Scientific | 301-06-451 | |
| Sterile Eppendorf tubes | Ultident | 24-MCT-150-C | |
| 50 mL conical tubes | VWR International | 89039-658 | |
| Cellkey ™ Small sample 96W microplate | Molecular Devices | 1026496 | |
| Cellkey ™ tips | Cybio | OL3800-25-559N | |
| Pre-cut pierceable seals | Excel Scientific, Inc. | XP-100 | |
| Equipment | | | |
| Automated cell counter (Vicell XR) | Beckman Coulter | 731050 | |
| Cell culture hood | Forma Scientific | 1284 | Class II |
| Liquid Nitrogen storage | Thermo Scientific | CY5093570 | |
| Water bath | VWR International | 89032-204 | |
| Standard light microscope | Leica Microsystems | DMIL LED | |
| Cell culture incubator | Thermo Scientific | 51019557 | 5% $CO_2$ at 37° C. |
| Low speed centrifuge | Thermo Scientific | 75004364 | |
| Cellkey ™ system | Molecular Devices | 1019185 | |

The solutions are prepared according to Table 3. The balanced salt solution (BSS) is kept at room temperature and all other solutions at 4° C. until the time of use. Cold media is warmed to 37° C. in a water bath for a few minutes before using.

TABLE 3

| | Solutions | |
|---|---|---|
| Solution A | Anhydrous D-glucose | 0.1% |
| | $CaCL_2 2H_2O$ | 0.05 mM |
| | $MgCL_2$ | 0.98 mM |
| | KCL | 5.4 mM |
| | Tris | 145 mM |
| Solution B | NaCL | 140 mM |
| Balanced Salt Solution (BSS) | Solution A | 1 volume |
| | Solution B | 9 volume |
| Complete media | RPMI-1640 | 500 mL |
| | Antibiotic-antimycotic | 1% |
| | FBS | 10% |
| Supplementary media | RPMI-1640 | 50 mL |
| | Antibiotic-antimycotic | 1% |
| | FBS | 40% |
| Freezing media | RPMI-1640 | 50 mL |
| | Antibiotic-antimycotic | 1% |
| | FBS | 40% |
| | DMSO | 20% |
| PHA media | RPMI-1640 | 500 mL |
| | Antibiotic-antimycotic | 1% |
| | FBS | 10% |
| | Phytohemaglutinin | 1% |

1. Preparation of olutions: 1. Prepare solutions according to Table 3 above. 2. Keep balanced salt solution (BSS) at room temperature and all other solutions at 4° C. until the time of use. 3. Heat media to 37° C. in the water bath for a few minutes before using.

2. Preparation and storage of PBMCs. 1. Collect 10 mL of whole blood in EDTA-treated collection tubes to prepare two aliquots of PBMCs using 5 mL for each aliquot. 2. Transfer 5 mL of whole blood from the EDTA-treated collection tube to a 50 mL tube. 3. Add an equal volume of BSS and mix sample by gentle pipetting up and down. 4. Place 3 mL of Ficoll in two 15 mL Falcon tubes. 5. Carefully layer 4.5 mL of diluted blood mixture over the Ficoll in each tube. 6. Let the tubes rest for up to 5 minutes to favor a clear separation of the blood and Ficoll. 7. Centrifuge the tubes at 400×g for 30 minutes at room temperature with no brake. 8. Carefully remove the tubes from the centrifuge so as to not disturb the layering. The PBMCs are visible at the BSS/Ficoll interface. 9. Harvest the cloudy layer of PBMCs at the interface of both tubes with a pipette and transfer to a new 50 mL tube. 10. Add 20 mL of complete media. 11. Centrifuge the tube at 288×g for 7 minutes at room temperature. 12. Remove the supernatant by aspiration. 13. Re-suspend the cell pellet in 500 µL of supplementary media. 14. Add an equal volume of freezing media. 15. Transfer the cell suspension to a cryovial. 16. Place the cryovial into a cryofreezing container with isopropanol. 17. Store the freezing container at −80° C. overnight. 18. Transfer the frozen PBMCs aliquot to liquid nitrogen for long-term storage.

3. Functional Assay: Day 1: 1. Place PBMCs aliquot from liquid nitrogen in water bath at 37° C. for a minute or until defrosted. 2. Transfer the cell suspension to a 50 mL tube with a sterile pipette. 3. Add 15 mL of Complete media and spin the cells down at 200×g for 5 minutes at room temperature. 4. Remove the supernatant by aspiration. 5. Gently suspend cell pellet in 1 mL of PHA media. 6. Complete the volume to 20 mL with the same media. 7. Cap the tube loosely to allow air to enter. 8. Leave the tube overnight at 37° C. in a $CO_2$ incubator to allow quiescent lymphocytes to transform into rapidly-proliferating lymphoblasts.

Day 2: 1. Take the tube out of the incubator, screw the caps completely and spin the cells down at 200×g for 5 min at room temperature. 2. Remove the supernatant by aspiration. 3. Gently suspend cell pellet in 1 mL of complete media. 4. Complete the volume to 20 mL with the same media. 5. Cap the tube loosely to allow air to enter. 6. Leave the tube overnight at 37° C. in a $CO_2$ incubator to expand cell numbers.

Day 3: 1. Take the tube out of the incubator, screw the caps completely and spin the cells down at 200×g for 5 min at room temperature. 2. Remove the supernatant by aspiration. 3. Wash cells twice with 10 mL of RPMI-1640 (media developed for growing human normal and neoplastic leukocytes (peripheral blood lymphocytes)) by centrifugation at 200×g for 5 min at room temperature. 4. Gently resuspend the cell pellet in 600 µL of RPMI-1640. 5. Measure the cell concentration and viability, using an automated cell counter and viability analyzer. 6. Add appropriate volume of RPMI-1640 to adjust to a cell concentration of $1.5 \times 10^5$ cell/20 µL. 7. Treat cells with recombinant OPN (rOPN) or vehicle (PBS). 7.1 Transfer 100 µL of cell suspension to two sterile 1.5 ml eppendorf tubes. 7.2 Add rOPN in one tube to a final concentration of 0.5 µg/mL. 7.3 Add an equal volume of PBS in the second tube. 7.4 Gently mix each condition by pipetting up and down twice using a sterile pipette set at 100 µL. 8. Prepare the small sample 96-well microplate. 8.1 Add 5 µL of RPMI-1640 to each well. 8.2 Centrifuge the plate at 200×g for 3 min to remove any air bubbles. 9. Seed the untreated cells as well as cells treated with rOPN or PBS. 9.1 Before transferring cells from tube to microplate, gently pipette up and down once to ensure a uniform suspension of cells. 9.2 Add 40 µL of cell suspension per well in quadruplicate for untreated cells, in duplicate for rOPN or PBS treated cells. Refer to FIG. 1 for the design. This design allows 12 patients to be tested on the same microplate. 9.3 Leave the cell plate under the sterile hood for 5 minutes to allow cells to rest and settle evenly to the bottom of the well before placing in the incubator. 9.4 Incubate the plate for 18 h at 37° C. in a $CO_2$ incubator to optimise the effect of OPN.

Figure 2:
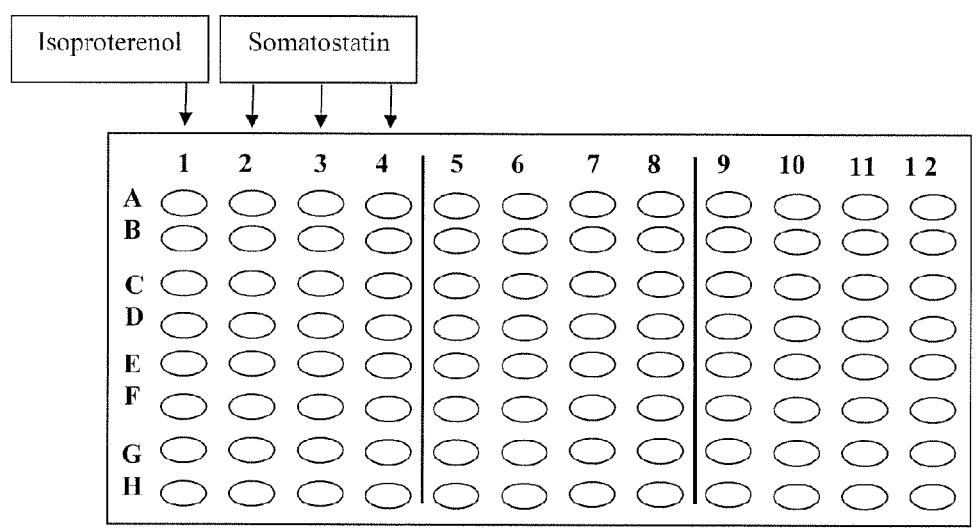
FIG. 2 shows an embodiment for a design for dispensing compounds in accordance with the present invention.

Day 4: 1. Run the plate with compounds. 1.1 Take the plate out of the incubator and leave it at room temperature for around 30 min. 1.2 Prepare 1 mL of 100 µM of Somatostatin (which activates Gi-mediated cellular response) and isoproterenol (which activates Gs-mediated cellular response) in RPMI-1640 by adding 10 µL of stock solution (10 mM) in 990 µL of RPMI-1640. 1.3 Fill the compound plate by dispensing 20 µL in appropriate wells as indicated in FIG. 2. 1.4 Cover the compound plate with a pre-cut pierceable seal to avoid change in compound concentration due to evaporation before or during incubation in the CDS-based system. 1.5 Load cell plate, pipette tips and compound plate into the CDS-based system. 1.6 Name the plate in the CDS-based instrument software. 1.7 Select the appropriate protocol. 1.8 The integrated fluidics system simultaneously adds the compounds to all wells by injecting 5 µL per well to achieve a final concentration of 10 µM in a total volume of 50 µL. 1.9 The CDS-based system automatically collects the data for 15 min after compound addition.

Data Analysis: 1. Select low and high ranges of frequencies to use when calculating extracted values for the non-adherent cells. 2. Select drift correction to correct the linear change in baseline impedance measurements over time. 3. Select data filtering to reduce variations in the kinetic response measurement due to electronic noise and compound addition. 4. Select the Max-Min method for the full analysis time. 5. Export data to Excel under the plate format option. 6. Calculate delta G (ΔG) by subtracting the average of response magnitude to Gi stimulation (RmGi) from the average of response magnitude to Gs stimulation (RmGs) using the following formula:

ΔG=RmGi−RmGs

7. Calculate the percentage of the fold effect (Fe) of OPN on Gi-mediated response by dividing the average of response magnitude to Gi stimulation in presence of OPN (RmGiOPN) with the average of response magnitude to Gi stimulation in presence of PBS (RmGiPBS) using the following formula:

Fe=100×(RmGiOPN/RmGiPBS)

Refer to Table 4 to classify patients.

TABLE 4

| Dynamic ranges with ΔG | Functional Groups | Dynamic ranges with Fe |
|---|---|---|
| ΔG < −10 | FG1 | Fe > 100% |
| −10 < ΔG < +10 | FG2 | Fe < 50% |
| ΔG > +10 | FG3 | 50% < Fe < 95% |

Example 2

IS Subjects or Subjects at Risk of Developing is can be Classified According to their Response to OPN Stimulation Cell viability was comparable between all samples with values consistent in the range of 86 and 96%. In contrast, high variations were noted in cell numbers among samples (FIG. 3). Of the 32 preclassified samples used, two had insufficient number of cells and have not been further classified. The functional classification of all patients samples used had been previously determined using one or more alternative classification method (e.g., cAMP-detection, impedance modification, etc.). An illustration of the functional classification according to the ΔG determined with CDS is showed in FIG. 4. The vertical axis of this figure is divided into three sections delineating the functional groups with dynamic ranges established as >+10 for FG3, between +10 and −10 for FG2 and finally <−10 for FG1. Among 30 patients tested 14, 6 and 5 patients were clearly classified into groups FG3, FG2 and FG1, respectively, while five patients notably 345, 353, 370, 371 and 382 had borderlines values (see FIG. 4).

Figure 5:
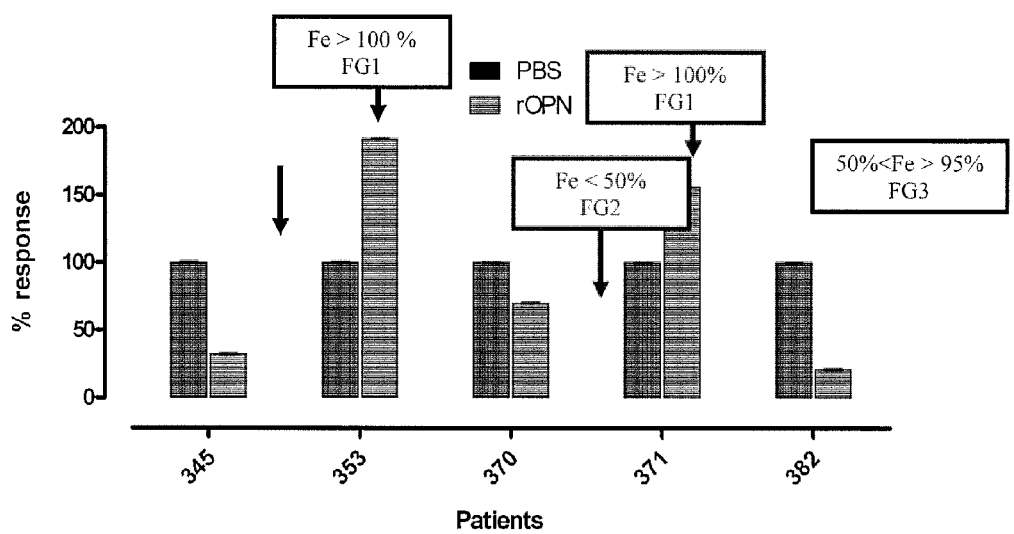
FIG. 5 shows the effect of rOPN on the cellular response to Gi stimulation in PBMCs. Cells were serum-starved for 18 h in the presence or absence of 0.5 µg/mL rOPN and then stimulated with 10 µM of somatostatin to initiate Gi-mediated cellular response. Data in the graph were generated from maximum-minimum impedance and correspond to the average of response in duplicate.

The evaluation of the OPN effect on the response to Gi stimulation revealed that OPN increased the response in patients 353 and 371. In contrast, the response was reduced by more than 50% in patients 345 and 382 and by less than 50% in patient 370 following rOPN treatment (FIG. 5). According to the classification criteria (Table 4) it was possible to categorize patients 353 and 371 in FG1, patients 345 and 382 in FG2, and patient 370 in FG3.

Figure 6:
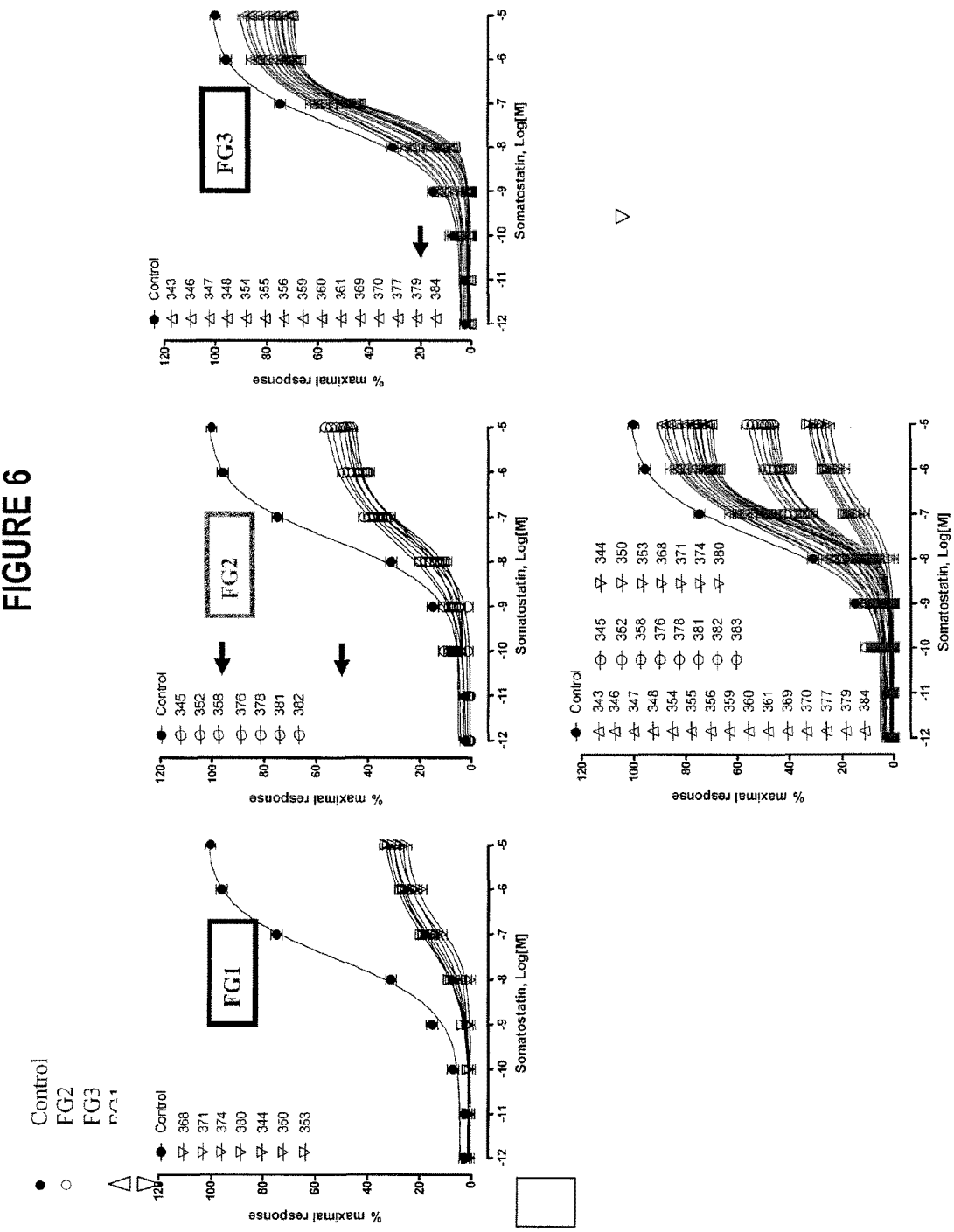
FIG. 6 shows the functional status (i.e., the magnitude of the cellular response to GiPCR-stimulation) of Gi proteins in PBMCs from control and scoliotic subjects. PBMCs from control and scoliotic subjects were exposed to increasing concentrations of somatostatin to stimulate Gi proteins via endogenous somatostatin receptor. The cellular response was measured by CDS-based system as described in Example 1. Curves were generated from maximum-minimum impedance. Each curve represents the non-linear regression performed with GraphPad™ Prism 5.0 software. Data were normalized to maximal response in cells from control subjects and each point corresponds to the average of response in duplicate. As shown, the percentage of maximal response relative to the control following Gi stimulation are below 40% (e.g., between about 10-40% for FG1), about 40 and 60% for FG2 and above 60% (e.g., about 60-90% for FG3).
Figure 7:
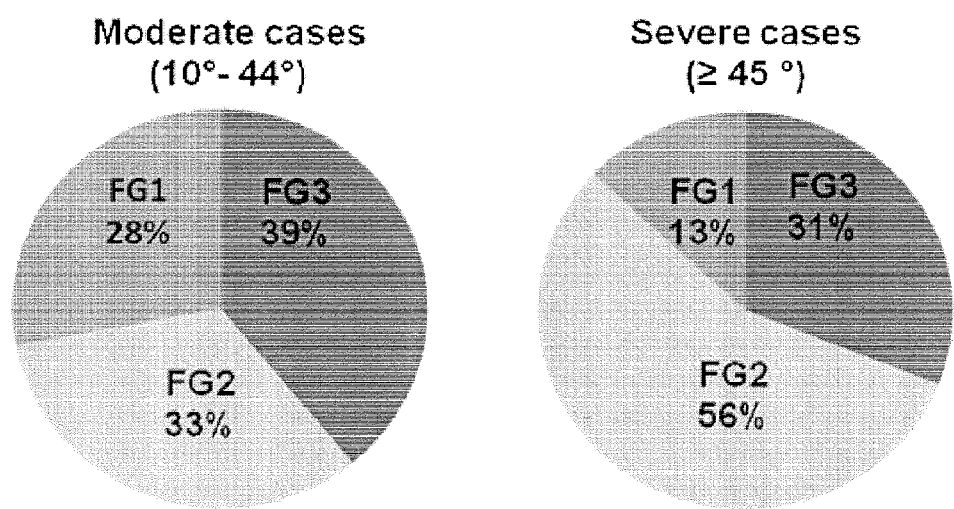
FIG. 7 shows the distribution of functional groups among different phases of scoliosis. A large cohort of scoliotic patients comprising 794 moderate cases (curvatures between 10 and 44 degrees) and 162 severe cases (curvature greater than 45 degrees) regularly followed at Sainte-Justine Hospital, were classified according to their degree of imbalance between response to Gi and Gs stimulation (ΔG). Responses were measured by the CDS-based system in response to 10 µM of somatostatin and isoproterenol.

In parallel, all patients were screened for their response to Gi protein stimulation and compared to control subjects. As expected, the latter classified the borderline subjects in the same functional group as the method determining the Gi mediated response in the presence or absence OPN ("Gi/OPN") did (FIG. 6). The classification of a large cohort of scoliotic patients regularly followed in our special clinic at Sainte-Justine Hospital has revealed that the three functional groups were similarly distributed among moderate cases, while the FG2 was predominant among severe cases (FIG. 7), identifying patients categorized into this functional group as more at risk for severe progression of the disease and indicating that this classification test can be useful in the prognosis of IS.

Example 3

Figure 10:
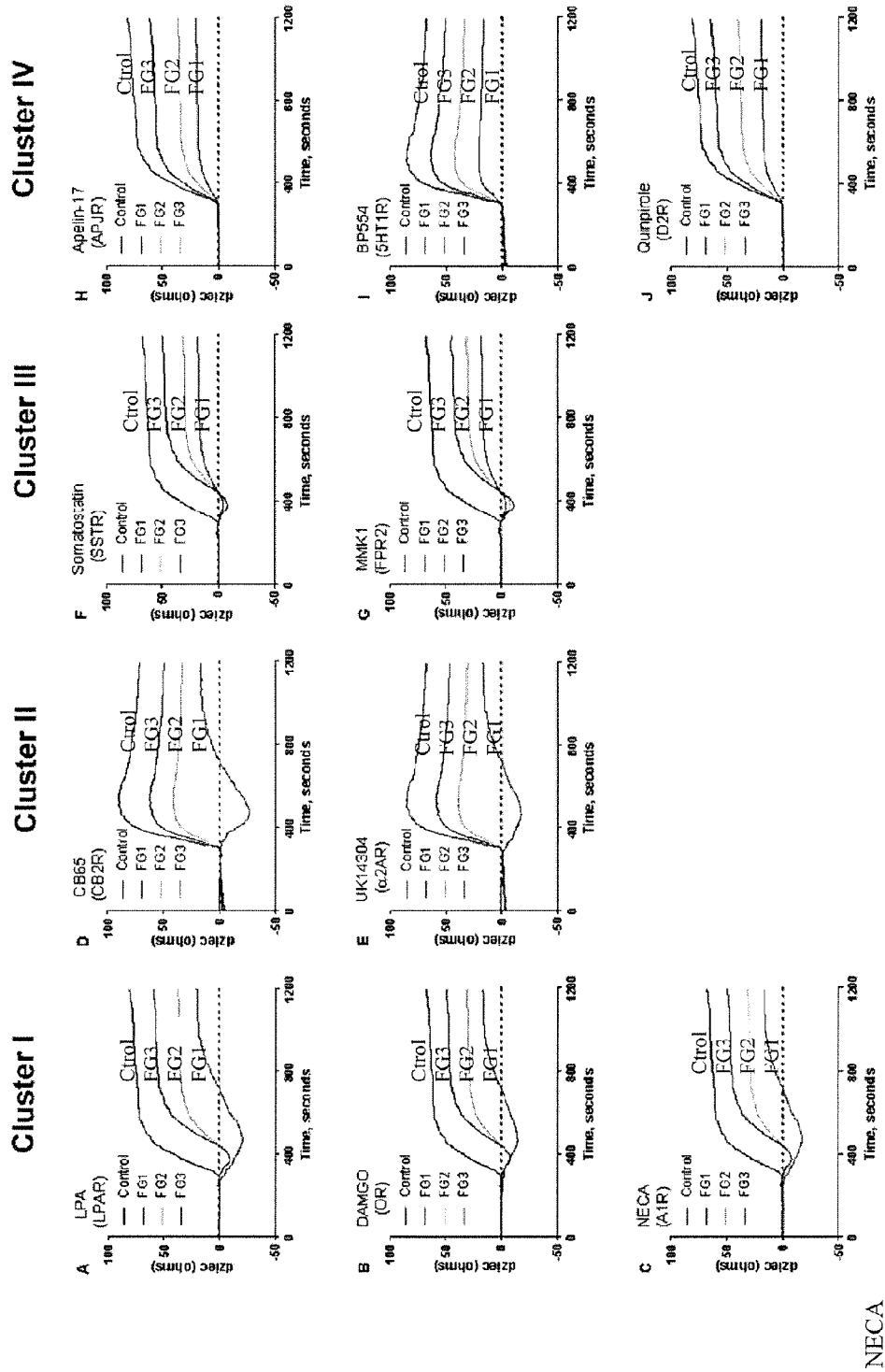
FIG. 10 shows that IS subjects or subjects at risk of developing IS can be classified according to their impedance signature in response to GiPCR stimulation in four receptor clusters. Impedance signatures of various GiPCR agonists in AIS osteoblasts reveal 4 distinct clusters. Cells were stimulated with 10 µM of (A) LPA, (B) DAMGO, (C) NECA, (D) CB65, (E) UK14304, (F) Somatostatin, (G) MMK1, (H) Apelin-17, (I) BP554 or (J) Quinpirole. The targeted endogenous receptors are shown in parentheses. The impedance represented in y-axis as dziec was measured by the Cellkey™ system every 2 sec. Data are representative of impedance signature in osteoblasts from 12 individuals tested three times in duplicate for each group.

IS Subjects or Subjects at Risk of Developing is can be Classified According to their Impedance Signature in Response to GiPCR Stimulation in Four Distinct Receptor Clusters In order to demonstrate that to determine if the reduced ability of Gi proteins to promote signal transduction in AIS is a generalized impairment and is not restricted to melatonin receptors, we performed a comparative study with various synthetic compounds activating selectively other receptors coupled to Gi proteins. A total of ten compounds were tested and the representative refraction index curves generated by each of these compounds in control and AIS osteoblasts are illustrated in FIGS. 10 (A-J). Analysis of impedance signature revealed that the tested compounds fell into four distinct clusters. In the cluster I (FIGS. 10, A-C), compounds elicit shapes of impedance profiles similar to those obtained with melatonin, consisting of a biphasic shape of impedance in all three AIS groups with a negative phase of larger extent for FG1. In cluster II (FIGS. 10, D and E), the compounds elicit negative response only in FG1. In cluster III (FIGS. 10, F and G), the compounds elicit a relatively short transient negative phase of a similar extent in all three AIS groups, while in cluster IV (FIGS. 10, H-J), the compounds totally lack this feature and elicit complete positive impedance in all AIS groups. Despite these differences in the shape of impedance profiles, the regression analysis of concentration-response curve of each tested compound revealed no significant difference in EC50 values between control and AIS groups (Table 5), while all groups were clearly distinguished by the amplitude of their maximum response (data not shown). In each case, the three AIS functional groups were less responsive than the control group. The reduction degree for each functional group relative to the control group was similar to that obtained with melatonin. This suggests that AIS patients can be classified using agonists of any GiPCR, with respect to the range of values as established with a melatonin receptor agonist.

Furthermore, based on the impedance profiles provided in FIG. 10 for cluster II agonists, it is possible to rapidly distinguish subjects belonging to the FG1 functional group over those belonging to the FG2 and FG3 functional groups. Indeed, subjects belonging to the FG1 functional group show a characteristic reduction in impedance, which is not present for the FG2 and FG3 groups.

TABLE 5

Potency of various GiPCR agonists for impedance response in osteoblasts from control and AIS patients

| | Control $EC_{50}$ (nM) | FG1 $EC_{50}$ (nM) | FG2 $EC_{50}$ (nM) | FG3 $EC_{50}$ (nM) |
|---|---|---|---|---|
| Melatonin | 33.4 = 8.4 | 42.3 = 9.4 | 48.68 = 6.4 | 45.79 = 5.3 |
| LPA | 8.52 = 1.5 | 8.78 ± 0.6 | 8.54 = 1.4 | 8.59 = 1.2 |
| DAMGO | 18.78 = 2.2 | 18.67 = 2.1 | 19.11 = 2.3 | 19.88 = 2.4 |
| NECA | 20.85 ± 2.2 | 20.88 = 1.7 | 20.83 = 1.2 | 22.25 = 2.2 |
| CB65 | 13.91 = 1.2 | 13.97 = 1.2 | 13.7 = 1.2 | 13.95 = 1.3 |
| UK14304 | 16.48 = 2.3 | 18.52 = 4.2 | 16.65 = 1.6 | 17.8 = 1.3 |
| Somatostatin | 31.12 = 3.3 | 31.23 = 3.1 | 31.3 = 2.6 | 30.98 = 2.3 |
| MMK1 | 48.95 = 4.3 | 50.51 = 2.3 | 50.45 = 5.2 | 51.58 = 2.3 |
| Apelin-17 | 32.50 = 2.3 | 32.45 = 2.6 | 32.67 = 1.9 | 39.1 = 2.4 |
| BP554 | 22.30 = 1.7 | 22.33 = 2.3 | 22.50 = 1.6 | 22.37 = 1.5 |
| Quinpirole | 43.57 = 4.1 | 45.39 = 4.2 | 47.1 = 3.2 | 48.7 ± 5.1 |

Example 4

IS Subjects or Subjects at Risk of Developing IS can be Classified According to their Response to GiPCR Stimulation in the Presence of PTX The effect of PTX on response to various selective agonists of Gi-coupled receptors was tested in AIS endophenotype groups FG1, FG2 and FG3 in four gene clusters.

Figure 11:
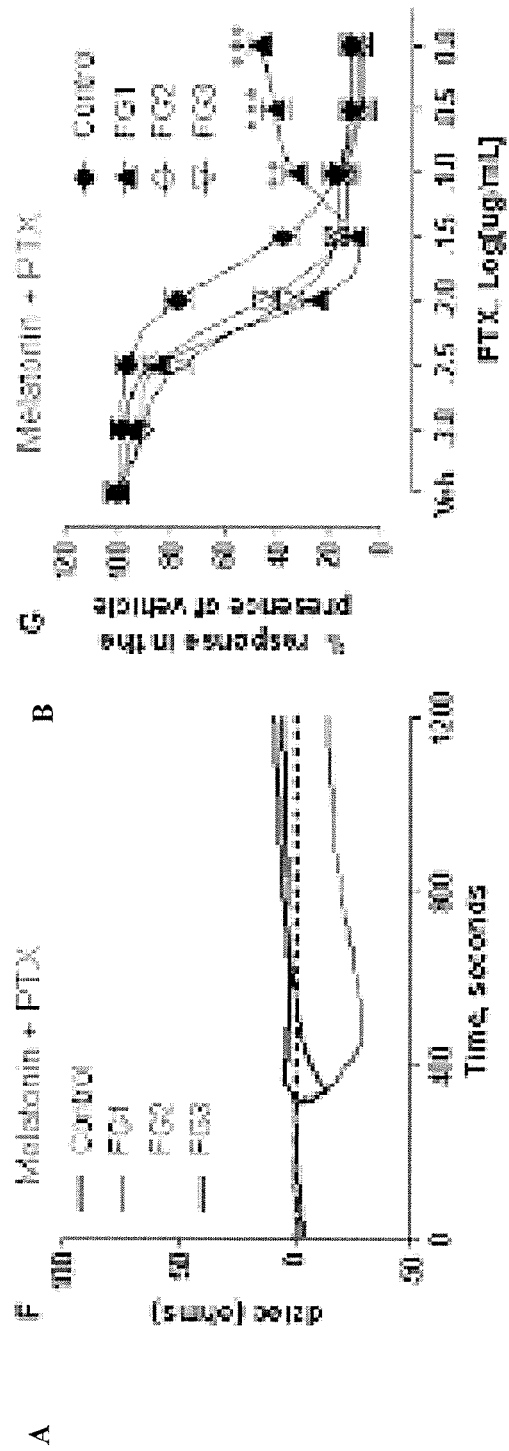
FIG. 11 shows dual melatonin signaling in AIS. (A) Effect of 16 h pre-treatment with 1 μg/mL PTX on kinetic signature of melatonin. (B) Effect of 16 h pre-treatment with varying concentration of PTX on impedance response to 10 μM melatonin normalized to the response in the presence of vehicle. Data are expressed as mean±SEM of experiments performed three times in duplicate for n=12 patients per group. *$P<0.05$, $P<0.01$, *$P<0.001$, versus control group based on one-way ANOVA followed by in post-doc test of Dunnett.

The amount of functional Gi proteins was selectively decreased by incubating osteoblasts with pertussis toxin (PTX) and Melatonin. Results showed that treatment with PTX did not alter the initial drop of the impedance response to melatonin in AIS groups but dramatically reduced the positive component as well in control as in AIS groups (FIG. 11A). The concentration-response curve describing the maximum impedance response showed that at low concentrations, PTX inhibited the response to melatonin in control and AIS groups, while at high concentrations, this treatment selectively increased response in FG1 (FIG. 11B). These results support a relationship between the divergent defective melatonin signaling and reduced Gi protein activity among AIS groups, and raise the possibility of a compensatory Gi-independent signaling pathway in AIS patients classified in FG1 group.

To determine if the reduced ability of Gi proteins to promote signal transduction in AIS is restricted to melatonin receptors, a comparative study using various agonists belonging to the four previously identified receptor clusters (see Example 3) in the presence of PTX was performed.

Figure 12:
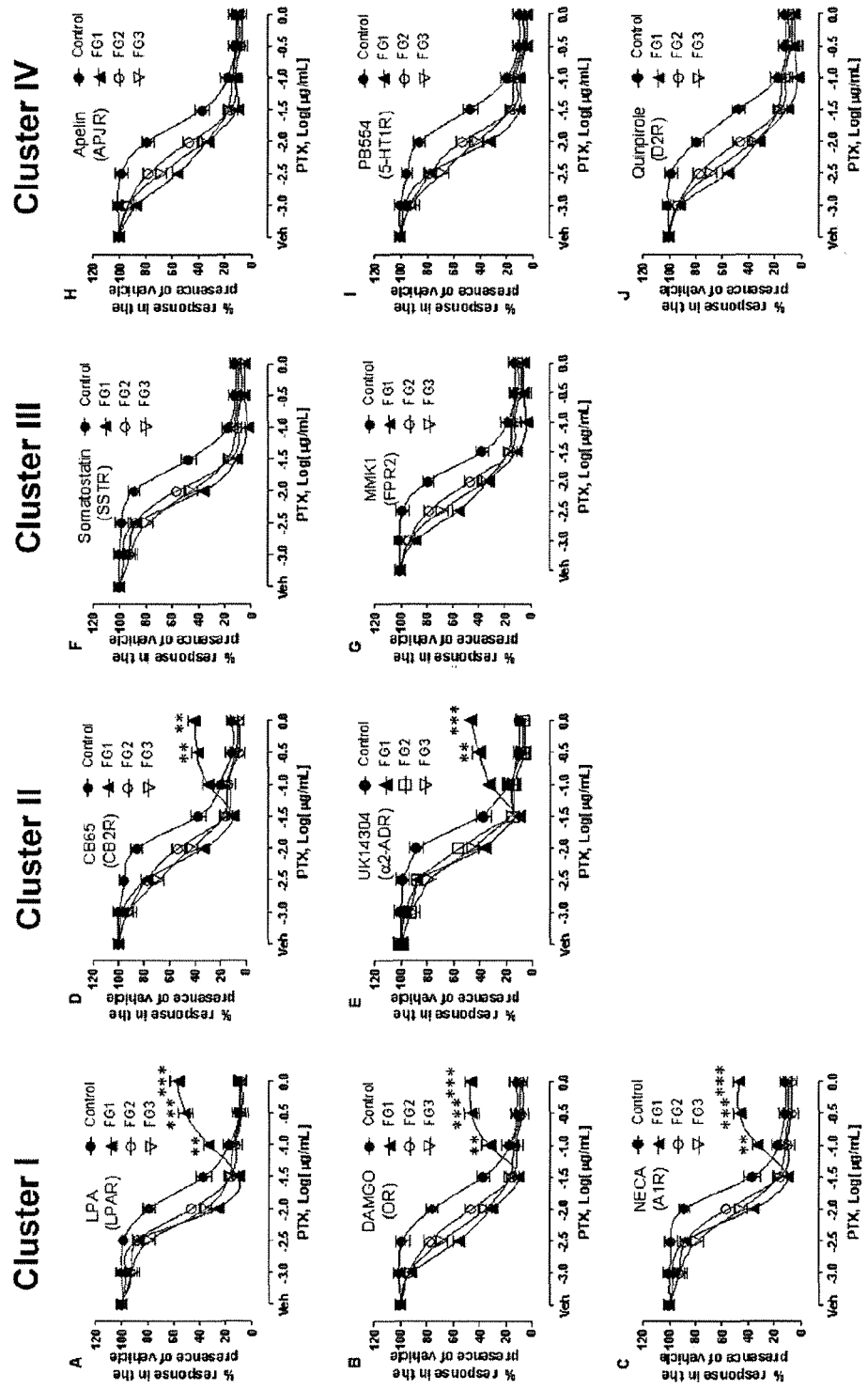
FIG. 12 shows the variations in the effect of PTX on response to various selective agonists of Gi-coupled receptors in FG1 subjects, depending on the receptor cluster. (A-J) Osteoblasts from control subjects or AIS patients of different groups were pre-incubated with varying concentrations of PTX for 16 h prior stimulation with 10 μM of specific synthetic agonist. The tested agonists and targeted receptors are indicated in each panel. Data were normalised to response in the presence of vehicle and are expressed as mean±SEM of experiments performed three times in duplicate for n=12 patients per group. *$P<0.05$, $P<0.01$, *$P<0.001$, versus control group based on one-way ANOVA followed by in post-doc test of Dunnett.

As shown in FIG. 12, following treatment with PTX at higher concentrations, only receptor agonists of clusters I and II (FIG. 12, A-E) elicited increased response in FG1 as observed following melatonin receptor stimulation, while response to receptor agonists of clusters III and IV in contrast, were abolished in all groups (FIG. 4, F-J). This supports the notion of a compensatory Gi-independent signaling in FG1 but independent of the receptor.

Based on these results, FG1 functional group could be easily distinguished by their response to cluster I and cluster II agonists in the presence of PTX. This test could advantageously be used to stratify borderline subjects (which may not be identified as belonging to the FG1 or FG2 functional group with sufficient confidence (high specificity) using other known methods or other GiPCR ligands.

Whether this signaling defect is confined in osteoblasts was examined by extending the analysis on myoblasts and PBMCs. It was found that both cell types exhibited a response pattern similar to that obtained with osteoblasts following stimulation with each of the tested compounds (data not shown). These findings are strongly indicative that the defective Gi-mediated signaling is a generalized impairment expressed in AIS.

Example 5

Differential Effects of Gs and Gq Knockdown by siRNA Method on the Biphasic Impedance Signature of GiPCR Agonists Among AIS Groups All $Gi_1$, $Gi_2$, $Gi_3$, Gs and scrambled siRNA were obtained from Ambion (Ambion USA). The sequences used for gene silencing are shown in supplemental Table 3. Osteoblasts from control subjects and AIS patients were transiently transfected in serum-free medium, using Lipofectamine RNAiMAX reagent (Invitrogen) according to the manufacturer's instructions and functional experiments were performed 48 h post transfection. The gene knockdown was evaluated by quantitative real-time PCR (qPCR).

Figure 13:
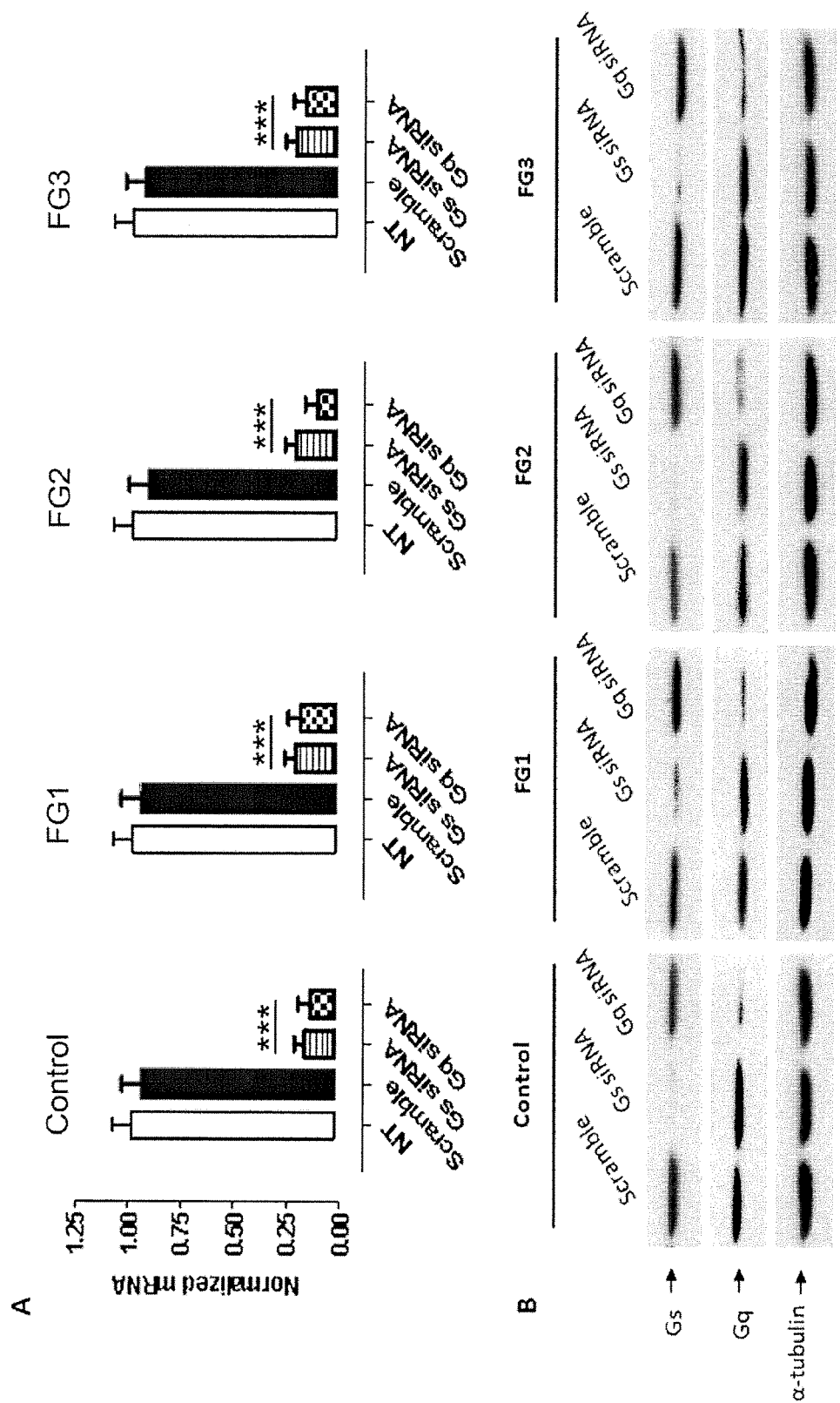
FIG. 13 shows the validation of the Gs and Gq siRNA effectiveness in AIS osteoblasts. (A) Total RNA extracted from control and AIS osteoblasts transfected with scramble, Gs or Gq siRNA and nontranfected (NT) cells, were subjected to qPCR analysis, using β-actin as internal control. Data are expressed as mean±SEM of n=12 patients for each group. *$P<0.05$, $P<0.01$, *$P<0.001$, versus NT cells based on one-way ANOVA followed by in post-doc test of Dunnett. (B) Total cell lysates from cells transfected with scramble, Gs or Gq siRNA, were subjected to western blot analysis, using antibody to α-tubulin as control. Bands shown are representative of results obtained with osteoblasts from 12 different patients for each AIS group.
Figure 14:
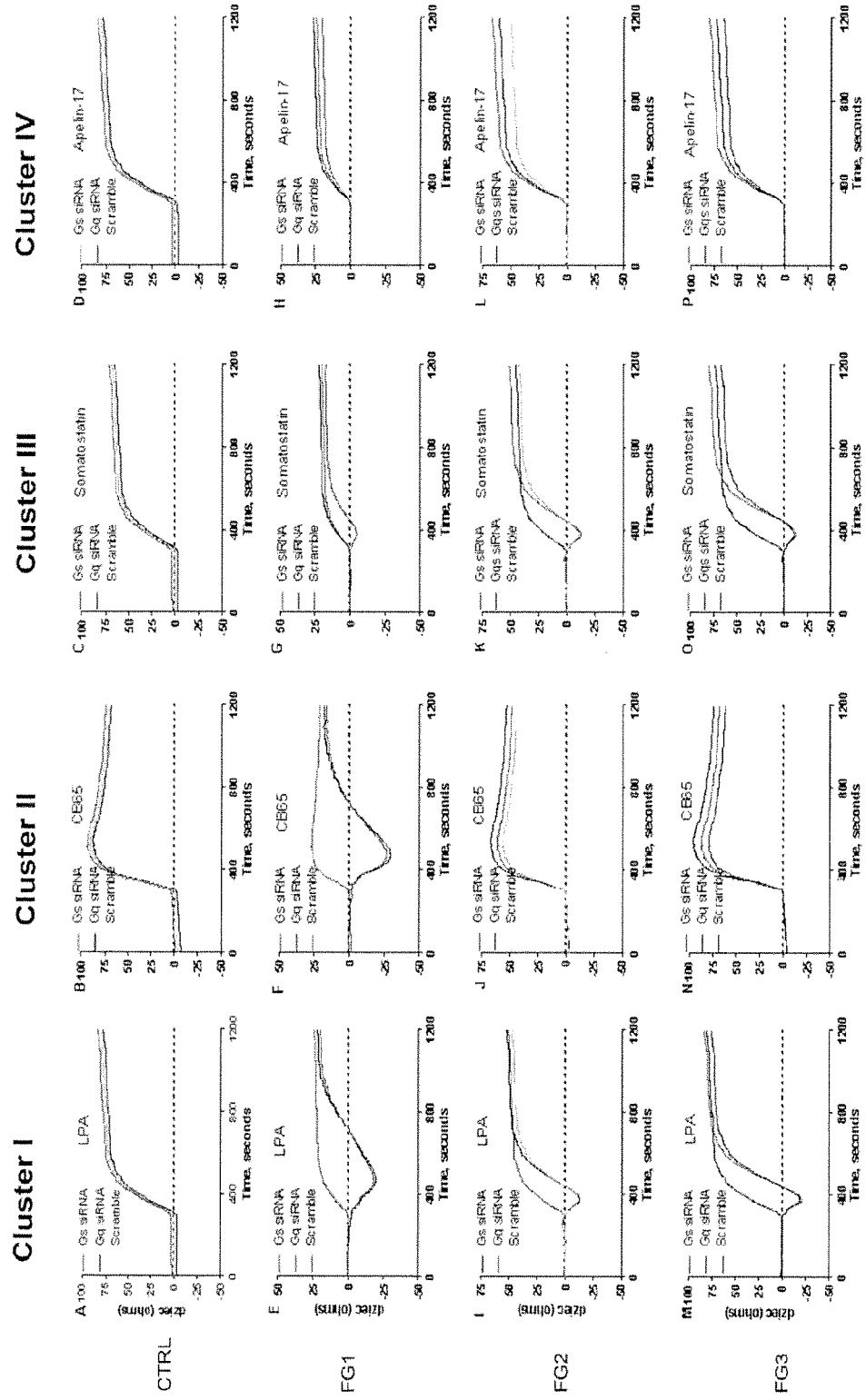
FIG. 14 shows the differential effects of Gs and Gq knockdown by siRNA method on the biphasic impedance signature of GiPCR agonists among AIS groups. Osteoblasts from control subjects and AIS patients of each functional group were transfected with scramble siRNA, Gs siRNA, or Gq siRNA. Efficiency of siRNA in control and AIS groups was verified with qPCR and Western blot analyses 48 hours after transfection, and response to stimulation with GiPCR agonist of cluster I, cluster II, cluster III and cluster IV was evaluated by challenging cells with 10 μM of (A, E, I, M) LPA, (B, F, J, N) CB65, (C, G, K, O) Somatostatin and (D, H, L, P) Apelin-17, respectively. The impedance represented in y-axis as dziec was measured every 2 sec. Data are representative of impedance signatures generated by CellKey™ system in osteoblasts from 12 individuals tested three times in duplicate for each group.

The possibility that the disparity in the shape of impedance among AIS groups in response to GiPCR activation implicates a component of Gs or Gq proteins-dependent response was then examined. For this purpose, the small interference RNA (siRNA) approach to knockdown Gs or Gq examined. For this purpose, the small interference RNA (siRNA) approach was used to knockdown Gs or Gq proteins prior to stimulate cells. Efficiency of siRNA was confirmed by qPCR (FIG. 13A) and western blot analyses (FIG. 13B). Results illustrated in FIG. 14 show that Gs or Gq protein deletion has no effect on the impedance signature of GiPCR agonists in control group (FIG. 14, A-D) for any agonist cluster. In contrast, in FG1 (FIGS. 14, E-H), the negative phase was completely abrogated by the deletion of Gs protein for clusters I and II and by the deletion of Gq protein for cluster III, while the positive phase remained unaffected by these deletions in all clusters. In FG2 subgroup (FIG. 14, I-L), the deletion of Gs protein was without effect on the negative phase in any clusters, while deletion of Gq protein led to the loss of negative phase without affecting the positive phase. Similar observations were noticed in FG3 (FIG. 14, M-P). These results suggest that Gs and Gq protein-dependent responses are integrated in the biphasic impedance signature of GiPCR in AIS. It appears that reduced Gi proteins associated with this disease favours the functional duality of these receptors and that the dual coupling to Gi and Gs protein is exclusively favoured in FG1.

The scope of the claims should not be limited by the preferred embodiments set forth in the examples, but should be given the broadest interpretation consistent with the description as a whole.

REFERENCES

1. Kane, W. J. Prevalence: a call for a statement of terms. Clin Orthop. Relat Res. 126, 43-46 (1977).
2. Bunnell, W. P. Selective screening for scoliosis. Clin Orthop Relat Res. 434, 40-45 (2005).
3. Asher, M. A. & Burton, D. C. Adolescent idiopathic scoliosis: natural history and long term treatment effects. Scoliosis. 1(1), 2 (2006).
4. Fong, D. Y., Lee, C. F., Cheung, K. M., Cheng, J. C., Ng, B. K., Lam, T. P., Mak, K. H., Yip, P. S. & Luk, K. D. A meta-analysis of the clinical effectiveness of school scoliosis screening. Spine (Phila Pa. 1976). 35(10), 1061-1071 (2010)
5. Chowanska, J., Kotwicki, T., Rosadzinski, K. & Sliwinski, Z. School screening for scoliosis: can surface topography replace examination with scoliometer? Scoliosis. 7(9), 1748-7161 (2012).
6. Kim, H., Kim, H. S., Moon, E. S., Yoon, C. S., Chung, T. S, Song, H. T., Suh, J. S., Lee, Y. H. & Kim, S. Scoliosis imaging: what radiologists should know. Radiographics. 30(7), 1823-1842 (2010)
7. Wong, H. K., Hui, J. H., Rajan, U. & Chia, H. P. Idiopathic scoliosis in Singapore schoolchildren: a prevalence study 15 years into the screening program. Spine (Phila Pa. 1976). 30(10), 1188-1196 (2005).
8. Nachemson, A. A long term follow-up study of non-treated scoliosis. Acta Orthop Scand. 39 (4), 466-476 (1968).
9. Enneking, W. F., & Harrington, P. Pathological changes in scoliosis. J Bone Joint Surg Am. 51 (1), 165-84 (1969).
10. Miller, N. H. Cause and natural history of adolescent idiopathic scoliosis. Orthop Clin North Am. 30(3), 343-52 (1999).
11. Nash, C. L. Jr., Gregg, E. C., Brown, R. H., & Pillai, K. Risks of exposure to X-rays in patients undergoing long-term treatment for scoliosis. J Bone Joint Surg Am. 61 (3), 371-400 (1979).
12. Akoume, M. Y., Azeddine, B., Turgeon, I., Franco, A., Labelle, H., Poitras, B., Rivard, C H., Grimard, G., Ouellet, J., Parent, S., & Moreau, A. Cell-based screening test for idiopathic scoliosis using cellular dielectric spectroscopy. Spine (Phila Pa. 1976). 35 (13), 601-608 (2010).
13. Akoume, M. Y., Veillette, M., Elbakry, M., Julien, C., Franco, A., Labelle, H., Poitras, B., Rivard, C H., Grimard, G., Ouellet, J., Parent, S., Lombardi, G., Colombini, A., Banfi, G., Brayda-Bruno, M., & Moreau, A. Disrupted Gi-coupled receptor signaling occurs in adolescent idiopathic scoliosis. J. clin. Invest. (2013) (submitted)
14. Verdonk, E, Johnson, K, McGuinness, R., Leung G., Chen, Y. W., Tang, H. R., Michelotti, J. M. & Liu, V. F. Cellular dielectric spectroscopy: a label-free comprehensive platform for functional evaluation of endogenous receptors. Assay Drug Dev Technol. 4(5), 609-6019 (2006).
15. Moreau, A., S. Forget, et al. (2004). "Melatonin signaling dysfunction in adolescent idiopathic scoliosis." *Spine* 29(16): 1772-1781.
16. Azeddine, B., K. Letellier, et al. (2007). "Molecular determinants of melatonin signaling dysfunction in adolescent idiopathic scoliosis." *Clin Orthop Relat Res* 462: 45-52.
17. Letellier, K., B. Azeddine, et al. (2008). "Estrogen cross-talk with the melatonin signaling pathway in human osteoblasts derived from adolescent idiopathic scoliosis patients." *J Pineal Res* 45(4): 383-393.
18. PCT/CA2014/050562

The invention claimed is:

1. A kit for classifying a subject having idiopathic scoliosis (IS) or at risk of developing IS comprising:
    (a) a purified recombinant osteopontin (rOPN) preparation; and
    (b) a ligand for Gi stimulation;
    wherein said kit optionally further comprises in addition to (a) and (b),
    (c) a ligand for Gs stimulation; and/or
    (d) one or more antibodies for detecting Giα phosphorylation.

2. The kit of claim 1, wherein said ligand for Gi stimulation is selected from the group consisting of: (a) melatonin for the MT2 receptor; (b) 1-[3-(3,4-Methylenedioxyphenoxy)propyl]-4-phenyl-piperazine (BP554) maleate for the 5-HT1A receptor; (c) 5-bromo-N-(4,5-dihydro-IH-imidazol-2-yl)-6-quinoxalinamine (UK14304 ) for the a2-AD receptor; (d) 1-Deoxy-1-[6-[[3-iodophenyl)methyl]amino]-9H-purin-9-yl]-N-methyl-β-D-ribofuranuronamide (IB-MECA) for the A3 receptor; (e) Lysophosphatidic acid (LPA) for the LPA receptor; (f) (2S)-2-[[2-[[(2R)-2-[[(2S)-2-amino-3-(4-hydroxyphenyl)propanoyl]amino]propanoyl]amino]acetyl]-methylamino]-N-(2-hydroxyethyl)-3-phenyl-propanamide (DMAGO) for the mu-opioid receptor; (g) 1-(6-Amino-9H-purin-9-yl)-1-deoxy-N-ethyl-β-D-ribofuranuronamide (NECA) for the adenosine receptors; (h) somatostatin for the SSTR receptor; (i) peptide MMK-1 for the FPR2 receptor; (j) Apelin-17 for the APJR receptor; (k) quinpirole for the D2 and D3 receptors; and (l) N-Cyclohexyl-7-chloro-1-[2-(4-morpholinyl)ethyl]quinolin-4(1H)-one-3-carboxamide (CB65) for the CB2 receptor.

3. The kit of claim 2, comprising a ligand for Gs stimulation, wherein said ligand for Gs stimulation is a ligand for a GsPCR selected from the group consisting of: 5-HT4, 5-HT7, ACTH receptor, Adenosine receptor types A2a and A2b, Arginine vasopressin receptor 2, Calcitonin receptor, Calcitonin gene-related peptide receptor, corticotropin-releasing hormone receptor, Dopamine receptors D1-like family (D1 and D5), FSH-receptor, Gastric inhibitory polypeptide receptor, Glucagon receptor, Histamine H2 receptor, Luteinizing hormone/choriogonadotropin receptor, melanocortin receptor, MC1R, MC3R, MC4R, MC5R, Parathyroid hormone receptor 1, Prostaglandin receptor types D2 and I2, secretin receptor and thyrotropin receptor.

4. The kit of claim 3, further comprising a reagent for measuring cellular cAMP concentration.

5. The kit of claim 2, comprising a ligand for Gs stimulation, wherein said ligand for Gs stimulation is a ligand for a GsPCR selected from the group consisting of: β-adrenergic receptors types β1, β2 and β3.

6. The kit of claim 1, wherein the ligand is a synthetic ligand.

7. The kit of claim 1, comprising melatonin, iodomelatonin or phenylmelatonin as a ligand for Gi stimulation.

8. A composition for classifying a subject having idiopathic scoliosis (IS) comprising:
   (a) a peripheral blood mononuclear cell (PBMC) sample from the subject;
   (b) osteopontin (OPN); and
   (c) a ligand for Gi stimulation;
   wherein said composition optionally further comprises in addition to (a), (b) and (c),
   (d) a ligand for Gs stimulation.

9. The composition of claim 8, wherein (i) the subject is a subject pre-diagnosed with IS; (ii) the subject is asymptomatic; and/or (iii) the subject has at least one family member suffering from IS.

10. The composition of claim 8, wherein the PBMC sample comprises fresh PBMCs.

11. The composition of claim 8, wherein the ligand is a synthetic ligand.

12. The composition of claim 8, wherein said ligand for Gi stimulation is selected from the group consisting of: (a) 1-[3-(3,4-Methylenedioxyphenoxy)propyl]-4-phenyl-piperazine (BP554) maleate for the 5-HT1A receptor; (b) 5-bromo-N-(4,5-dihydro-IH-imidazol-2-yl)-6-quinoxalin-amine (UK14304) for the a2-AD receptor; (c) 1-Deoxy-1-[6-[[3-iodophenyl)methyl]amino]-9H-purin-9-yl]-N-methyl-β-D-ribofuranuronamide (IB-MECA) for the A3 receptor; (d) Lysophosphatidic acid (LPA) for the LPA receptor; (e) (2S)-2-[[2-[[(2R)-2-[[(2S)-2-amino-3-(4-hydroxyphenyl)propanoyl]amino]propanoyl]amino]acetyl]methylamino]-N-(2-hydroxyethyl)-3-phenylpropanamide (DMAGO) for the mu-opioid receptor; (f) 1-(6-Amino-9H-purin-9-yl)-1-deoxy-N-ethyl-β-D-ribofuranuronamide (NECA) for the adenosine receptors; (g) somatostatin for the SSTR receptor; (h) peptide MMK-1 for the FPR2 receptor; (i) Apelin-17 for the APJR receptor; (j) quinpirole for the D2 and D3 receptors; and (k) N-Cyclohexyl-7-chloro-1-[2-(4-morpholinyl)ethyl]quinolin-4(1H)-one-3-carboxamide (CB65) for the CB2 receptor.

13. The composition of claim 8, wherein said ligand for Gi stimulation is melatonin, iodomelatonin or phenylmelatonin.

14. The composition of claim 8, wherein said ligand for Gi stimulation is somatostatin.

15. The composition of claim 8, further comprising a reagent for measuring cellular cAMP concentration.

16. A kit for classifying a subject having idiopathic scoliosis (IS) or at risk of developing IS comprising:
   (a) recombinant osteopontin (rOPN); and
   (b) somatostatin;
   wherein said kit optionally further comprises in addition to (a) and (b),
   (c) a ligand for Gs stimulation; and/or
   (d) one or more antibodies for detecting Giα phosphorylation.

17. A composition for classifying a subject having idiopathic scoliosis (IS) comprising:
   (a) an isolated peripheral blood mononuclear cell (PBMC) sample from the subject;
   (b) osteopontin (OPN); and
   (c) a ligand for Gi stimulation;
   wherein said composition optionally further comprises in addition to (a), (b) and (c),
   (d) a ligand for Gs stimulation;
   wherein said OPN is recombinant OPN (rOPN) or is present at a concentration of 0.5 μg/ml.

18. The kit of claim 17, wherein said ligand for Gs stimulation is isoproterenol.

* * * * *